(12) United States Patent
Minke et al.

(10) Patent No.: US 7,455,844 B2
(45) Date of Patent: Nov. 25, 2008

(54) VACCINE AGAINST STREPTOCOCCI

(75) Inventors: Jules Maarten Minke, Corbas (FR); Jean-Christophe Francis Audonnet, Lyons (FR)

(73) Assignee: Merial Limited, Duluth, GA (US)

( * ) Notice: Subject to any disclaimer, the term of this patent is extended or adjusted under 35 U.S.C. 154(b) by 0 days.

(21) Appl. No.: 11/692,968

(22) Filed: Mar. 29, 2007

(65) Prior Publication Data

US 2007/0243195 A1   Oct. 18, 2007

Related U.S. Application Data

(60) Provisional application No. 60/786,936, filed on Mar. 29, 2006.

(51) Int. Cl.
  *G01N 33/53* (2006.01)
  *A61K 39/00* (2006.01)
  *A61K 39/09* (2006.01)
(52) U.S. Cl. .................. 424/244.1; 424/185.1; 435/7.1
(58) Field of Classification Search ........................ None
  See application file for complete search history.

(56) References Cited

U.S. PATENT DOCUMENTS 6,120,775 A * 9/2000 Jacobs ..................... 424/244.1
7,138,125 B2 * 11/2006 Emery et al. ............. 424/234.1

OTHER PUBLICATIONS

Waller et al. The Veterinary Journal 173 (2007):492-501.*
Abbas et al. Cellular and Molecular Immunology 2000 Chapter 15 p. 360-362).*
Ellis, R.W. (Chapter 29 of "Vaccines" [Plotkin, S.A. et al. (eds) published by W. B. Saunders company (Philadelphia) in 1988.*
Harrington et al. Microbes and Infection 2002, 4:501-510.*
Bork et al Genome Research 10: 398-400, 2000.*
Sequence Q8GLF7-Immunoreactive protein Se68.9 fragment (UNIProtKB/TrEMBL) database Mar. 1, 2003 (Qin et al).*
N. Chanter et al., Equine strangles modelled in mice, Veterinary Microbiology 43 (1995) 209-218.
Flock et al., Recombinant *Streptococcus equi* Proteins Protect Mice in Challenge Experiments and Induce Immune Response in Horses, Infection and Immunity, Jun. 2004, p. 3228-3236 vol. 72, No. 6.

* cited by examiner

*Primary Examiner*—Robert A. Zeman
*Assistant Examiner*—Oluwatosin Ogunbiyi
(74) *Attorney, Agent, or Firm*—Judy Jarecki-Black; Thomas Kowalski, Esq.

(57) ABSTRACT

The invention relates to subunit immunogenic or vaccine compositions which may comprise at least one polypeptide of *Streptococcus equi* and methods for preparing and/or formulating such compositions. The invention also relates to the use of such subunit compositions, such as a method for eliciting an immunogenic response or a protective immune response, which may comprise administering the composition to a mammal susceptible to streptococcal infection.

4 Claims, 7 Drawing Sheets

VACCINE AGAINST STREPTOCOCCI

INCORPORATION BY REFERENCE

This application claims benefit of U.S. provisional patent application Ser. No. 60/786,936 filed Mar. 29, 2006.

The foregoing applications, and all documents cited therein or during their prosecution ("appln cited documents") and all documents cited or referenced in the appln cited documents, and all documents cited or referenced herein ("herein cited documents"), and all documents cited or referenced in herein cited documents, together with any manufacturer's instructions, descriptions, product specifications, and product sheets for any products mentioned herein or in any document incorporated by reference herein, are hereby incorporated herein by reference, and may be employed in the practice of the invention.

FIELD OF THE INVENTION

The present invention relates to polypeptides of streptococcal bacteria, more particularly of *Streptococcus equi*, which may be used to prevent, diagnose and/or treat streptococcal infection.

BACKGROUND OF THE INVENTION

*Streptococcus equi* (*S. equi* subsp. *equi*) is a gram-positive coccus that has a large capsule. *S. equi* is the causative agent of strangles in equine, canine and Camelids, notably in horses, donkeys, mules, dogs, camels and dromedaries. Strangles is a highly contagious infection of the upper respiratory tract and associated lymph nodes. In equine, the disease is characterized by fever, thick mucopurulent nasal discharge, swelling and abscessation of the submandibular, submaxillary, and retropharyngeal lymph nodes. In severe cases, the infection may become disseminated with internal and external abscess formation and may ultimately result in death. It can occur in susceptible horses of any age. Transmission occurs through direct contact or indirectly through fomites that have been contaminated by respiratory tract secretions or saliva. Although rare, *S. equi* is a very serious zoonotic pathogen of Camelids (Sechi L A et al., New Microbiol, 1999, 22(4): 383-387), of humans infected by contact with horses (Elsayed S et al., Clin Microbiol Infect, 2003, 9(8): 869-872). In human, mortality was high (25%), especially among older patients and patients with endocarditis, meningitis and disseminated infection (Bradley S F et al., Rev Infect Dis, 1991, 13(2): 270-280; Popescu G A et al., South Med J, 2006, 99(2): 190-191).

After infection, *S. equi* generally has an incubation period 3 to 14 days before the onset of clinical signs. The organism rapidly translocates the mucosa into the lymphatic channels and from there moves to one or more of the regional lymph nodes leading to inflammation and swelling.

The enlarging lymph nodes soon develop purulent centers with fluctuant liquefaction. Submandibular lymph nodes typically rupture externally through the skin, whilst abscesses formed in the retropharyngeal lymph nodes typically rupture into the guttural pouch. This may take up to 2 weeks to occur after the onset of signs.

The majority (70%) of animals are immune to further attacks of strangles after recovery from a first infection. However, a substantial proportion of animals (30%) can contract the disease a second time, and of these a small proportion can contract the disease more than twice (Todd A. G., J. Comp. Pathol. Ther., 1910, 23, 212-229). Up to 10% of affected animals continue to shed *S. equi* intermittently for prolonged periods after clinical signs have resolved. This carrier state is probably caused by incomplete drainage of exudate from the guttural pouches (empyaema) and/or sinuses following rupture of abscesses formed in the retropharyngeal lymph nodes (Newton J R et al., Vet Record, 1997, 140: 84-90). Drying and hardening of exudate leads to the formation of discrete bodies called chondroids that can remain in the guttural pouch for several years. It is becoming increasingly recognised around the world that sub-clinical persistent carriage of *S. equi* is fundamental to the persistence of this infection between outbreaks (Fintl C et al., Vet Record, 2000, 147: 480-484; Newton J R et al., Vet Record, 1997, 140: 84-90; Newton J R et al., Equine Vet J, 2000, 32: 515-526; Timoney J F et al., Vet Record, 1998, 142: 648) and this remains true despite the advent of modern vaccines (Newton R et al., Vet Record, 2005, 156: 291-292).

Protection against the disease is primarily mediated by antibodies of the IgA and IgG subclasses locally produced in the nasopharynx.

Serum antibodies to *Streptococcus equi* (*S. equi*) can be measured by a variety of assays including ELISA (Reif et al., Proc. Am. Assoc. Equine Practitioners, 1982, 27, 33-40), the mouse protection test (Bazely P. L., Aust. Vet. J., 1943, 19, 62-85), and the gel diffusion precipitin test.

Commercially available vaccines consisting of heat-inactivated bacterin or M-protein-rich extracts have been widely used in the field. Although effective in stimulating serum bactericidal antibodies, these vaccines apparently do not stimulate a useful level of nasopharyngeal antibody and so the level of protection stimulated in a horse population is disappointing. An avirulent, genetically modified strain of *S. equi* administered intranasally has recently been shown to stimulate local nasopharyngeal antibodies similar to those found in convalescent immune horses. Vaccinated horses were immune to subsequent experimental challenge with virulent *S. equi* (Timoney and Galan, 1985, The protective response of the horse to an avirulent strain of Streptococcal equi. In Y. Kimura, S. Kotami and Y. Shokawa, eds., Recent Advances in Streptococci and Streptococcal disease. Reedbooks, Surrey, England, p. 294-295). It therefore appears that an effective strangles vaccine must be able to stimulate a nasopharyngeal immune response.

Bacterin-type vaccines aften cause undesirable local and systemic reactions consisting of edema, induration, stiffness, transient fever, and neutrophilia, effects that are probably due to cell wall peptidoglycan. Furthermore, purpura hemorrhagica can develop after vaccination of horses previously sensitised to streptococcal antigens.

*Streptococcus zooepidemicus* (*S. equi* subsp. *zooepidemicus*) is an important cause of respiratory disease and metritis in equine. *S. zooepidemicus* is an opportunist pathogen that causes purulent respiratory infections of weanling and yearling horses and uterine infections in elderly mares. In the situation of concurrent influenza infection high temperature or transport stress, it can be a devasting and rapid fatal pathogen in the respiratory tract. Although rare, *S. zooepidemicus* is a very serious zoonotic pathogen of Camelids (Younan M et al., J Vet Med B Infect Dis Vet Public Health, 2005, 52(3): 142-146), of humans infected by contact with horses (Downar J et al., J Clin Microbiol, 2001, 39(6): 2358-2359; Ural O et al., Scand J Infect Dis, 2003, 35(3): 206-207) and of canine animals having respiratory disease, notably already infected by *Bordetella bronchiseptica* (Chalker V J et al., Vet Microbiol, 2003, 95(1-2): 149-156).

*S. equi* affected mammals may harbor the bacteria for several months in, among other places, the guttoral pouches and, thus, shed and act as reservoirs of *S. equi*. Although *S. equi* is quite sensitive to penicillin and other antibiotics, antibiotic treatment is for various reasons mostly ineffective. In order to combat the disease and mitigate serious clinical complications, research has mainly been aimed at developing efficient vaccines.

The development of vaccines has been slow, possibly in part, because vaccines must be able to control infection without inducing a marked inflammatory response.

It is therefore desirable to develop vaccines having a high degree of immunogenicity and which exhibit a good safety profile with limited or no side effects.

Citation or identification of any document in this application is not an admission that such document is available as prior art to the present invention.

SUMMARY OF THE INVENTION

The invention relates to subunit immunogenic or vaccine compositions which may comprise at least one polypeptide of the invention; e.g., polypeptides of *Streptococcus equi*. The invention therefore further relates to methods for preparing and/or formulating such compositions; e.g., admixing the polypeptides with a suitable veterinary or pharmaceutically acceptable carrier, excipient, diluent or vehicle and/or an adjuvant and/or stabilizer. The invention also relates to the use of such subunit compositions; e.g., a method for eliciting an immunogenic response or a protective immune response, which may comprise administering the composition to a mammal susceptible to streptococcal infection.

The invention relates to recombinant immunogenic or vaccine compositions which may comprise at least one recombinant expression vector encoding at least one polypeptide of the invention, able to express in vivo this polypeptide in a mammal susceptible to streptococcal infection. Herein such a immunogenic or vaccine composition which may comprise at least one recombinant expression vector is named a recombinant immunogenic or vaccine composition. The invention therefore further relates to methods for preparing such vectors, e.g., inserting at least one polynucleotide encoding a polypeptide according to the invention into a plasmid vector or viral vector so that the vector contains and expresses the polynucleotide in the host. The invention therefore further relates to methods for formulating such recombinant immunogenic or vaccine compositions; e.g., admixing the vectors with a suitable veterinary or pharmaceutically acceptable carrier, excipient, diluent or vehicle and/or an adjuvant and/or stabilizer. The invention also relates to the use of such recombinant immunogenic or vaccine compositions; e.g., a method for eliciting an immunogenic response or a protective immune response, which may comprise administering the composition to a mammal susceptible to streptococcal infection.

By definition, mammals susceptible to streptococcal infection encompasse equine (i.e. horses, mares, foals, donkeys and mules), camelids (i.e. camels, dromedaries), canine (i.e. dogs, bitchs, puppies), bovine (i.e. cattle, cows, calves), ovine (i.e sheeps, ewes, lambs), caprine (i.e. goats), porcine (i.e. pigs, sows, piglets) and human. Mammals susceptible to *Streptococcus equi* infection encompass equine (i.e. horses, mares, foals, donkeys and mules), camelids (i.e. camels, dromedaries), canine (i.e. dogs, bitchs, puppies) and human. Mammals susceptible to *Streptococcus zooepidemicus* infection encompasse equine (i.e. horses, mares, foals, donkeys and mules), canine (i.e. dogs, bitchs, puppies), Camelids (i.e. camels, dromedaries) and human.

The invention also relates to uses recombinant expression vectors; e.g., a method for producing a polypeptide of the invention, which may comprise culturing, growing or propagating prokaryotic or eucaryotic cells transformed to contain the recombinant expression vectors and to express a polynucleotide encoding the polypeptide under conditions suitable for expression, and harvesting or isolating or separating the polypeptide from cells transformed to express it.

The invention further relates to methods for inducing in an equine, i.e. a horse, a donkey and a mule, an immunogenic or protective immune response against streptococcal bacteria, such as *Streptococcus equi* or *Streptococcus zooepidemicus*, which may comprise administering to the equine a subunit immunogenic or vaccine composition of the invention or a recombinant immunogenic or vaccine composition of the invention.

The invention further relates to methods for inducing in a canine, i.e. a dog, a bitch, a puppy, an immunogenic or protective immune response against streptococcal bacteria, such as *Streptococcus equi* or *Streptococcus zooepidemicus*, which may comprise administering to the canine a subunit immunogenic or vaccine composition of the invention or a recombinant immunogenic or vaccine composition of the invention.

The invention further relates to methods for inducing in a Camelid, i.e. a camel, a dromedary, an immunogenic or protective immune response against streptococcal bacteria, such as *Streptococcus equi* or *Streptococcus zooepidemicus*, which may comprise administering to the Camelid a subunit immunogenic or vaccine composition of the invention or a recombinant immunogenic or vaccine composition of the invention.

The invention further relates to methods for inducing in a human an immunogenic or protective immune response against streptococcal bacteria, such as *Streptococcus equi* or *Streptococcus zooepidemicus*, which may comprise administering to the human a subunit immunogenic or vaccine composition of the invention or a recombinant immunogenic or vaccine composition of the invention.

The invention relates to a polypeptide having an amino acid sequence coded by a polynucleotide selected from the group consisting of polynucleotides identified SEQ ID NOS: 17, 19, 21, 23 and 25. The invention further relates to a polypeptide having an identity which is equal or more than about 70%, 75%, 80%, 85%, 90%, 91%, 92%, 93%, 94%, 95%, 96%, 97%, 98%, or 99% with an amino acid sequence coded by a polynucleotide selected from the group consisting of polynucleotides identified SEQ ID NOS: 17, 19, 21, 23 and 25. The invention relates to a polypeptide selected from the group consisting of polypeptides identified SEQ ID NOS: 18, 20, 22, 24, 26, 48, 50 and 52. The invention further relates to a polypeptide analog having an identity which is equal or more than about 70%, 75%, 80%, 85%, 90%, 91%, 92%, 93%, 94%, 95%, 96%, 97%, 98%, or 99% with a polypeptide selected from the group consisting of polypeptides identified SEQ ID NOS: 18, 20, 22, 24, 26, 48, 50 and 52. The invention further relates to a polypeptide fragment, containing at least one epitope, which is a part of a polypeptide selected from the group consisting of polypeptides identified SEQ ID NOS: 18, 20, 22, 24, 26, 48, 50 and 52 or analogs thereof, and notably a fragment containing at least one epitope selected from the group consisting of polypeptides identified SEQ ID NOS: 32, 34, 36, 38, 40, 54, 56 and 58. And, the invention relates to uses, compositions and methods involving such polypeptides, analogs thereof or fragments thereof as herein described.

Thus, the invention relates to a recombinant expression vector, wherein said vector contains at least one polynucleotide which codes for a polypeptide selected from the group consisting of polypeptides identified SEQ ID NOS: 18, 20, 22, 24, 26, 48, 50 and 52, and combinations thereof. The invention further relates to a recombinant expression vector, wherein said vector has at least one polynucleotide which codes for a polypeptide analog having an identity which is equal or more than about 70%, 75%, 80%, 85%, 90%, 91%, 92%, 93%, 94%, 95%, 96%, 97%, 98%, or 99% with a polypeptide selected from the group consisting of polypeptides identified SEQ ID NOS: 18, 20, 22, 24, 26, 48, 50 and 52, and combinations thereof. The invention further relates to a recombinant expression vector, wherein said vector has at least one polynucleotide which codes for a polypeptide fragment, containing at least one epitope which is a part of a polypeptide selected from the group consisting of polypeptides identified SEQ ID NOS: 18, 20, 22, 24, 26, 48, 50 and 52 or analogs thereof, and notably a fragment selected from the group consisting of polypeptides identified SEQ ID NOS: 32, 34, 36, 38, 40, 54, 56 and 58. The invention relates to a recombinant expression vector, wherein said vector has at least one polynucleotide selected from the group consisting of polynucleotides identified SEQ ID NOS: 17, 19, 21, 23, 25, 31, 33, 35, 37, 39, 47, 49, 51, 53, 55 and 57, and combinations thereof. The invention further relates to a recombinant expression vector, wherein said vector has at least one polynucleotide having an identity which is equal or more than about 70%, 75%, 80%, 85%, 90%, 91%, 92%, 93%, 94%, 95%, 96%, 97%, 98%, or 99% with a polynucleotide selected from the group consisting of polynucleotides identified SEQ ID NOS: 17, 19, 21, 23, 25, 31, 33, 35, 37, 39, 47, 49, 51, 53, 55 and 57, and combinations thereof. And, the invention relates to uses, compositions and methods involving such vectors as herein described.

Polynucleotides of the invention may be used in hybridization reactions (e.g. Northern or Southern blots, or in nucleic acid microarrays or "gene chips") or in amplification reactions (e.g. polymerase chain reaction or PCR).

It should be appreciated that the invention provides polynucleotides which may comprise sequences complementary to those described above.

Polynucleotides according to the invention may be prepared in many ways (e.g. by chemical synthesis, from genomic or cDNA libraries, from the *streptococcus* itself etc.) and may take various forms (e.g. single stranded, double stranded, primers, probes etc.).

Polynucleotides according to the invention may be labeled e.g. with a radioactive or fluorescent label. This is particularly useful as a primer or as a probe.

In addition, the term "polynucleotide" includes DNA and RNA, and also their analogues, such as those containing modified backbones.

Further still, the invention envisions an antibody preparation which may comprise at least one antibody specific to a polypeptide of the invention. This antibody may be polyclonal or monoclonal. The antibody preparation may also comprise a fragment of said antibody.

The invention also involves a diagnostic kit for detecting infection by streptococcal bacteria, including at least one polypeptide according to the invention or an antibody preparation which may comprise at least one antibody specific to a polypeptide of the invention. The invention also involves a diagnostic method for detecting infection by streptococcal bacteria in mammals, which may comprise using a diagnostic kit of the invention and detecting in a sample the polypeptide or an antibody specific to that polypeptide.

The invention further concerns a passive immunization method which may comprise administering the antibody preparation to a mammal susceptible to infection by streptococcal bacteria or infected by streptococcal bacteria. In particular, the passive immunization method comprises administering the antibody preparation to an equine susceptible to infection by the streptococcal bacterium or infected by the streptococcal bacterium, notably susceptible to infection by *Streptococcus equi* or infected by *Streptococcus equi*.

It is noted that in this disclosure and particularly in the claims, terms such as "comprises", "comprised", "comprising" and the like can have the meaning attributed to it in U.S. Patent law; e.g., they can mean "includes", "included", "including", and the like; and that terms such as "consisting essentially of" and "consists essentially of" have the meaning ascribed to them in U.S. Patent law, e.g., they allow for elements not explicitly recited, but exclude elements that are found in the prior art or that affect a basic or novel characteristic of the invention.

These and other embodiments are disclosed or are obvious from and encompassed by, the following Detailed Description.

BRIEF DESCRIPTION OF THE DRAWINGS

The following detailed description, given by way of example, but not intended to limit the invention solely to the specific embodiments described, may best be understood in conjunction with the accompanying drawings, in which.

DETAILED DESCRIPTION

Figure 1:
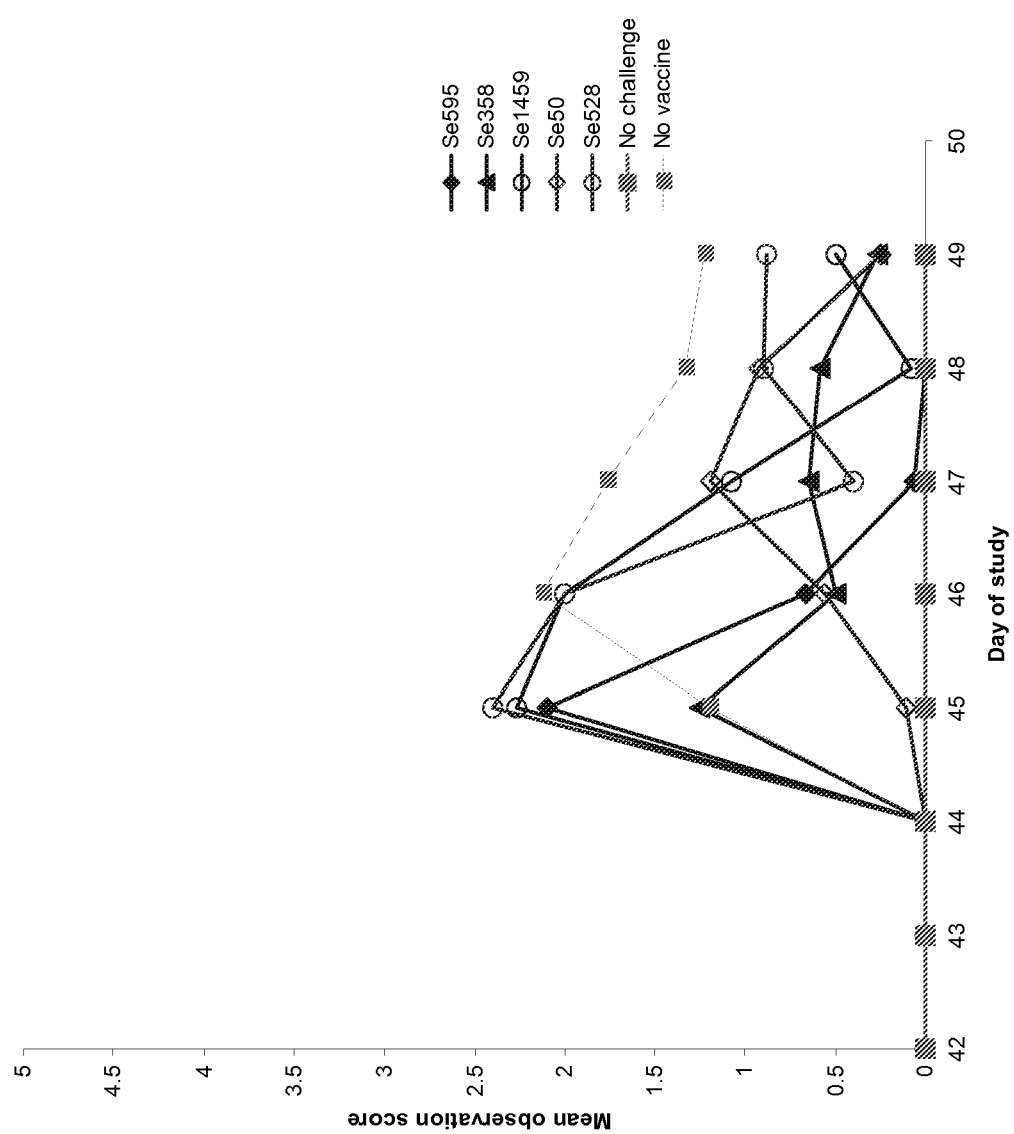
FIG. 1 shows the mean clinical scores of vaccinated and control mice following challenge with *Streptococcus equi*.

The present invention relates to the identification of polypeptides of *Streptococcus equi* able, when administered to a mammal, to elicit an immunogenic or immune response, and to the identification of polynucleotides encoding these polypeptides. These polypeptides are useful for the production of subunit immunogenic compositions or subunit vaccines. These polynucleotides are useful for the production of DNA immunogenic compositions, DNA vaccines, recombinant viral vector immunogenic compositions or recombinant viral vector vaccines.

The invention concerns compositions, uses and methods against infections caused by bacteria of the *Streptococcal* family, notably caused by *Streptococcus equi*, e.g. strangles disease in equine, camelid, canine and human, and against infections caused by *Streptococcus zooepidemicus* in equine, camelid, canine and human.

The invention concerns polypeptides, polynucleotides and genes obtained or derived from *Streptococcus equi*. The present invention may relate also to polypeptides, polynucleotides and genes obtained or derived from other streptococci, notably from *Streptococcus zooepidemicus, Streptococcus suis, Streptococcus uberis, Streptococcus dysgalactiae, Streptococcus agalactiae, Streptococcus pneumoniae, Streptococcus pyogenes*.

A particular aspect of the invention is a polypeptide selected from the amino acid sequences SEQ ID NOS: 18, 20, 22, 24, 26, 48, 50 and 52.

The whole genome of *Streptococcus equi* is available in the Sanger database (http://www.sanger.ac.uk/Projects/S_equi/).

The polypeptides are identified as SEQ ID NOS: 18, 20, 22, 24, 26, 48, 50 and 52 for Se50, Se1459, Se595, Se528, Se358, Se1631, Se1681 and S1a, respectively.

A particular aspect of the invention is a polynucleotide selected from the nucleotide sequences SEQ ID NOS: 17, 19, 21, 23 and 25.

The polynucleotides are identified as SEQ ID NOS: 17, 19, 21, 23 and 25 for Se50, Se1459, Se595, Se528 and Se358, respectively.

The practice of the present invention will employ, unless otherwise indicated, conventional techniques of molecular biology, microbiology, recombinant DNA technology, and immunology, which are within the skill of the art. Such techniques are explained fully in the literature. See, e.g., Sambrook et al. (2001) Molecular Cloning: A Laboratory Manual, 3rd ed., Cold Spring Harbor Press; DNA Cloning, Vols. I and II (D. N. Glover ed. 1985); Oligonucleotide Synthesis (M. J. Gait ed. 1984); Nucleic Acid Hybridization (B. D. Hames & S. J. Higgins eds. 1984); Animal Cell Culture (R. K. Freshney ed. 1986); Immobilized Cells and Enzymes (IRL press, 1986); Perbal, B., A Practical Guide to Molecular Cloning (1984); the series, Methods In Enzymology (S. Colowick and N. Kaplan eds., Academic Press, Inc.); and Handbook of Experimental Immunology, Vols. I-IV (D. M. Weir and C. C. Blackwell eds., 1986, Blackwell Scientific Publications).

Before describing the present invention in detail, it is to be understood that this invention is not limited to particular DNA, polypeptide sequences or process parameters as such may, of course, vary. It is also to be understood that the terminology used herein is for the purpose of describing particular embodiments of the invention only, and is not intended to be limiting.

Unless defined otherwise, all technical and scientific terms used herein have the same meaning as commonly understood by one of ordinary skill in the art to which the invention pertains. Although a number of methods and materials similar or equivalent to those described herein can be used in the practice of the present invention, the preferred materials and methods are described herein.

By the term "complementarity" or "complementary" is meant, for the purposes of the specification or claims, a sufficient number in the oligonucleotide of complementary base pairs in its sequence to interact specifically (hybridize) with a target nucleic acid sequence of the gene polymorphism to be amplified or detected. As known to those skilled in the art, a very high degree of complementarity is needed for specificity and sensitivity involving hybridization, although it need not be 100%. Thus, for example, an oligonucleotide that is identical in nucleotide sequence to an oligonucleotide disclosed herein, except for one base change or substitution, may function equivalently to the disclosed oligonucleotides. A "complementary DNA" or "cDNA" gene includes recombinant genes synthesized by reverse transcription of messenger RNA ("mRNA").

A "cyclic polymerase-mediated reaction" refers to a biochemical reaction in which a template molecule or a population of template molecules is periodically and repeatedly copied to create a complementary template molecule or complementary template molecules, thereby increasing the number of the template molecules over time.

By the term "detectable moiety" is meant, for the purposes of the specification or claims, a label molecule (isotopic or non-isotopic) which is incorporated indirectly or directly into an oligonucleotide, wherein the label molecule facilitates the detection of the oligonucleotide in which it is incorporated, for example when the oligonucleotide is hybridized to amplified gene polymorphic sequences. Thus, "detectable moiety" is used synonymously with "label molecule". Synthesis of oligonucleotides can be accomplished by any one of several methods known to those skilled in the art. Label molecules, known to those skilled in the art as being useful for detection, include chemiluminescent, fluorescent or luminescent molecules. Various fluorescent molecules are known in the art which are suitable for use to label a nucleic acid for the method of the present invention. The protocol for such incorporation may vary depending upon the fluorescent molecule used. Such protocols are known in the art for the respective fluorescent molecule.

"DNA amplification" as used herein refers to any process that increases the number of copies of a specific DNA sequence by enzymatically amplifying the nucleic acid sequence. A variety of processes are known. One of the most commonly used is the polymerase chain reaction (PCR) process of Mullis as described in U.S. Pat. Nos. 4,683,195 and 4,683,202. Methods, devices and reagents as described in U.S. Pat. Nos. 6,951,726; 6,927,024; 6,924,127; 6,893,863; 6,887,664; 6,881,559; 6,855,522; 6,855,521; 6,849,430; 6,849,404; 6,846,631; 6,844,158; 6,844,155; 6,818,437; 6,818,402; 6,794,177; 6,794,133; 6,790,952; 6,783,940; 6,773,901; 6,770,440; 6,767,724; 6,750,022; 6,744,789; 6,733,999; 6,733,972; 6,703,236; 6,699,713; 6,696,277; 6,664,080; 6,664,064; 6,664,044; RE38,352; 6,650,719; 6,645,758; 6,645,720; 6,642,000; 6,638,716; 6,632,653; 6,617,107; 6,613,560; 6,610,487; 6,596,492; 6,586,250; 6,586,233; 6,569,678; 6,569,627; 6,566,103; 6,566,067; 6,566,052; 6,558,929; 6,558,909; 6,551,783; 6,544,782; 6,537,752; 6,524,830; 6,518,020; 6,514,750; 6,514,706; 6,503,750; 6,503,705; 6,493,640; 6,492,114; 6,485,907; 6,485,903; 6,482,588; 6,475,729; 6,468,743; 6,465,638; 6,465,637; 6,465,171; 6,448,014; 6,432,646; 6,428,987; 6,426,215; 6,423,499; 6,410,223; 6,403,341; 6,399,320; 6,395,518; 6,391,559; 6,383,755; 6,379,932; 6,372,484; 6,368,834; 6,365,375; 6,358,680; 6,355,422; 6,348,336; 6,346,384; 6,319,673; 6,316,195; 6,316,192; 6,312,930; 6,309,840; 6,309,837; 6,303,343; 6,300,073; 6,300,072; 6,287,781; 6,284,455; 6,277,605; 6,270,977; 6,270,966; 6,268,153; 6,268,143; D445,907; 6,261,431; 6,258,570; 6,258,567; 6,258,537; 6,258,529; 6,251,607; 6,248,567; 6,235,468; 6,232,079; 6,225,093; 6,221,595; D441,091; 6,218,153; 6,207,425; 6,183,999; 6,183,963; 6,180,372; 6,180,349; 6,174,670; 6,153,412; 6,146,834; 6,143,496; 6,140,613; 6,140,110; 6,103,468; 6,087,097; 6,072,369; 6,068,974; 6,063,563; 6,048,688; 6,046,039; 6,037,129; 6,033,854; 6,031,960; 6,017,699; 6,015,664; 6,015,534; 6,004,747; 6,001,612; 6,001,572; 5,985,619; 5,976,842; 5,972,602; 5,968,730; 5,958,686; 5,955,274; 5,952,200; 5,936,968; 5,909,468; 5,905,732; 5,888,740; 5,883,924; 5,876,978; 5,876,977; 5,874,221; 5,869,318; 5,863,772; 5,863,731; 5,861,251; 5,861,245; 5,858,725; 5,858,718; 5,856,086; 5,853,991; 5,849,497; 5,837,468; 5,830,663; 5,827,695; 5,827,661; 5,827,657; 5,824,516; 5,824,479;

5,817,797; 5,814,489; 5,814,453; 5,811,296; 5,804,383; 5,800,997; 5,780,271; 5,780,222; 5,776,686; 5,774,497; 5,766,889; 5,759,822; 5,750,347; 5,747,251; 5,741,656; 5,716,784; 5,712,125; 5,712,090; 5,710,381; 5,705,627; 5,702,884; 5,693,467; 5,691,146; 5,681,741; 5,674,717; 5,665,572; 5,665,539; 5,656,493; 5,656,461; 5,654,144; 5,652,102; 5,650,268; 5,643,765; 5,639,871; 5,639,611; 5,639,606; 5,631,128; 5,629,178; 5,627,054; 5,618,703; 5,618,702; 5,614,388; 5,610,017; 5,602,756; 5,599,674; 5,589,333; 5,585,238; 5,576,197; 5,565,340; 5,565,339; 5,556,774; 5,556,773; 5,538,871; 5,527,898; 5,527,510; 5,514,568; 5,512,463; 5,512,462; 5,501,947; 5,494,795; 5,491,225; 5,487,993; 5,487,985; 5,484,699; 5,476,774; 5,475,610; 5,447,839; 5,437,975; 5,436,144; 5,426,026; 5,420,009; 5,411,876; 5,393,657; 5,389,512; 5,364,790; 5,364,758; 5,340,728; 5,283,171; 5,279,952; 5,254,469; 5,241,363; 5,232,829; 5,231,015; 5,229,297; 5,224,778; 5,219,727; 5,213,961; 5,198,337; 5,187,060; 5,142,033; 5,091,310; 5,082,780; 5,066,584; 5,023,171 and 5,008,182 may also be employed in the practice of the present invention. PCR involves the use of a thermostable DNA polymerase, known sequences as primers, and heating cycles, which separate the replicating deoxyribonucleic acid (DNA), strands and exponentially amplify a gene of interest. Any type of PCR, such as quantitative PCR, RT-PCR, hot start PCR, LAPCR, multiplex PCR, touchdown PCR, etc., may be used. Advantageously, real-time PCR is used. In general, the PCR amplification process involves a cyclic enzymatic chain reaction for preparing exponential quantities of a specific nucleic acid sequence. It requires a small amount of a sequence to initiate the chain reaction and oligonucleotide primers that will hybridize to the sequence. In PCR the primers are annealed to denatured nucleic acid followed by extension with an inducing agent (enzyme) and nucleotides. This results in newly synthesized extension products. Since these newly synthesized sequences become templates for the primers, repeated cycles of denaturing, primer annealing, and extension results in exponential accumulation of the specific sequence being amplified. The extension product of the chain reaction will be a discrete nucleic acid duplex with a termini corresponding to the ends of the specific primers employed.

By the terms "enzymatically amplify" or "amplify" is meant, for the purposes of the specification or claims, DNA amplification, i.e., a process by which nucleic acid sequences are amplified in number. There are several means for enzymatically amplifying nucleic acid sequences. Currently the most commonly used method is the polymerase chain reaction (PCR). Other amplification methods include LCR (ligase chain reaction) which utilizes DNA ligase, and a probe consisting of two halves of a DNA segment that is complementary to the sequence of the DNA to be amplified, enzyme QB replicase and a ribonucleic acid (RNA) sequence template attached to a probe complementary to the DNA to be copied which is used to make a DNA template for exponential production of complementary RNA; strand displacement amplification (SDA); Qβ replicase amplification (QβRA); self-sustained replication (3SR); and NASBA (nucleic acid sequence-based amplification), which can be performed on RNA or DNA as the nucleic acid sequence to be amplified.

A "fragment" of a molecule such as a protein or nucleic acid is meant to refer to any portion of the amino acid or nucleotide genetic sequence.

As used herein, the term "genome" refers to all the genetic material in the chromosomes of a particular organism. Its size is generally given as its total number of base pairs. Within the genome, the term "gene" refers to an ordered sequence of nucleotides located in a particular position on a particular chromosome that encodes a specific functional product (e.g., a protein or RNA molecule). In general, an animal's genetic characteristics, as defined by the nucleotide sequence of its genome, are known as its "genotype," while the animal's physical traits are described as its "phenotype."

By "hybridization" or "hybridizing," as used herein, is meant the formation of A-T and C-G base pairs between the nucleotide sequence of a fragment of a segment of a polynucleotide and a complementary nucleotide sequence of an oligonucleotide. By complementary is meant that at the locus of each A, C, G or T (or U in a ribonucleotide) in the fragment sequence, the oligonucleotide sequenced has a T, G, C or A, respectively. The hybridized fragment/oligonucleotide is called a "duplex."

A "hybridization complex", such as in a sandwich assay, means a complex of nucleic acid molecules including at least the target nucleic acid and a sensor probe. It may also include an anchor probe.

A "melting temperature" is meant the temperature at which hybridized duplexes dehybridize and return to their single-stranded state. Likewise, hybridization will not occur in the first place between two oligonucleotides, or, herein, an oligonucleotide and a fragment, at temperatures above the melting temperature of the resulting duplex. It is presently advantageous that the difference in melting point temperatures of oligonucleotide-fragment duplexes of this invention be from about 1° C. to about 10° C. so as to be readily detectable.

As used herein, the term "nucleic acid molecule" is intended to include DNA molecules (e.g., cDNA or genomic DNA), RNA molecules (e.g., mRNA), analogs of the DNA or RNA generated using nucleotide analogs, and derivatives, fragments and homologs thereof. The nucleic acid molecule can be single-stranded or double-stranded, but advantageously is double-stranded DNA. "DNA" refers to the polymeric form of deoxyribonucleotides (adenine, guanine, thymine, or cytosine) in its either single stranded form, or a double-stranded helix. This term refers only to the primary and secondary structure of the molecule, and does not limit it to any particular tertiary forms. Thus, this term includes double-stranded DNA found, inter alia, in linear DNA molecules (e.g., restriction fragments), viruses, plasmids, and chromosomes. In discussing the structure of particular double-stranded DNA molecules, sequences may be described herein according to the normal convention of giving only the sequence in the 5' to 3' direction along the nontranscribed strand of DNA (i.e., the strand having a sequence homologous to the mRNA). An "isolated" nucleic acid molecule is one that is separated from other nucleic acid molecules that are present in the natural source of the nucleic acid.

A "nucleoside" refers to a base linked to a sugar. The base may be adenine (A), guanine (G) (or its substitute, inosine (I)), cytosine (C), or thymine (T) (or its substitute, uracil (U)). The sugar may be ribose (the sugar of a natural nucleotide in RNA) or 2-deoxyribose (the sugar of a natural nucleotide in DNA). A "nucleotide" refers to a nucleoside linked to a single phosphate group.

As used herein, the term "oligonucleotide" refers to a series of linked nucleotide residues, which oligonucleotide has a sufficient number of nucleotide bases to be used in a PCR reaction. A short oligonucleotide sequence may be based on, or designed from, a genomic or cDNA sequence and is used to amplify, confirm, or reveal the presence of an identical, similar or complementary DNA or RNA in a particular cell or tissue. Oligonucleotides may be chemically synthesized and may be used as primers or probes. Oligonucleotide means any nucleotide of more than 3 bases in length used to facilitate detection or identification of a target nucleic acid, including probes and primers.

A "polymerase" is an enzyme that catalyzes the sequential addition of monomeric units to a polymeric chain, or links two or more monomeric units to initiate a polymeric chain. The "polymerase" will work by adding monomeric units whose identity is determined by and which is complementary to a template molecule of a specific sequence. For example, DNA polymerases such as DNA pol 1 and Taq polymerase add deoxyribonucleotides to the 3' end of a polynucleotide chain in a template-dependent manner, thereby synthesizing a nucleic acid that is complementary to the template molecule. Polymerases may be used either to extend a primer once or repetitively or to amplify a polynucleotide by repetitive priming of two complementary strands using two primers. A "thermostable polymerase" refers to a DNA or RNA polymerase enzyme that can withstand extremely high temperatures, such as those approaching 100° C. Often, thermostable polymerases are derived from organisms that live in extreme temperatures, such as *Thermus aquaticus*. Examples of thermostable polymerases include Taq, Tth, Pfu, Vent, deep vent, UlTma, and variations and derivatives thereof.

A "polynucleotide" refers to a linear chain of nucleotides connected by a phosphodiester linkage between the 3'-hydroxyl group of one nucleoside and the 5'-hydroxyl group of a second nucleoside which in turn is linked through its 3'-hydroxyl group to the 5'-hydroxyl group of a third nucleoside and so on to form a polymer comprised of nucleosides linked by a phosphodiester backbone. A "modified polynucleotide" refers to a polynucleotide in which one or more natural nucleotides have been partially, substantially, or completely replaced with modified nucleotides.

A "primer" is an oligonucleotide, the sequence of at least of portion of which is complementary to a segment of a template DNA which is to be amplified or replicated. Typically primers are used in performing the polymerase chain reaction (PCR). A primer hybridizes with (or "anneals" to) the template DNA and is used by the polymerase enzyme uses as the starting point for the replication/amplification process. The primers herein are selected to be "substantially" complementary to different strands of a particular target DNA sequence. This means that the primers must be sufficiently complementary to hybridize with their respective strands. Therefore, the primer sequence need not reflect the exact sequence of the template. For example, a non-complementary nucleotide fragment may be attached to the 5' end of the primer, with the remainder of the primer sequence being complementary to the strand. Alternatively, non-complementary bases or longer sequences can be interspersed into the primer, provided that the primer sequence has sufficient complementarity with the sequence of the strand to hybridize therewith and thereby form the template for the synthesis of the extension product.

"Probes" refer to oligonucleotides nucleic acid sequences of variable length, used in the detection of identical, similar, or complementary nucleic acid sequences by hybridization. An oligonucleotide sequence used as a detection probe may be labeled with a detectable moiety.

The following are non-limiting examples of polynucleotides: a gene or gene fragment, exons, introns, mRNA, tRNA, rRNA, ribozymes, cDNA, recombinant polynucleotides, branched polynucleotides, plasmids, vectors, isolated DNA of any sequence, isolated RNA of any sequence, nucleic acid probes and primers. A polynucleotide may comprise modified nucleotides, such as methylated nucleotides and nucleotide analogs, uracil, other sugars and linking groups such as fluororibose and thiolate, and nucleotide branches. The sequence of nucleotides may be further modified after polymerization, such as by conjugation, with a labeling component. Other types of modifications included in this definition are caps, substitution of one or more of the naturally occurring nucleotides with an analog, and introduction of means for attaching the polynucleotide to proteins, metal ions, labeling components, other polynucleotides or solid support.

An "isolated" polynucleotide or polypeptide is one that is substantially pure of the materials with which it is associated in its native environment. By substantially free, is meant at least 50%, at least 55%, at least 60%, at least 65%, at advantageously at least 70%, at least 75%, more advantageously at least 80%, at least 85%, even more advantageously at least 90%, at least 91%, at least 92%, at least 93%, at least 94%, at least 95%, at least 96%, at least 97%, most advantageously at least 98%, at least 99%, at least 99.5%, at least 99.9% free of these materials.

An "isolated" nucleic acid molecule is a nucleic acid molecule separate and discrete from the whole organism with which the molecule is found in nature; or a nucleic acid molecule devoid, in whole or part, of sequences normally associated with it in nature; or a sequence, as it exists in nature, but having heterologous sequences (as defined below) in association therewith.

The term "polynucleotide encoding a protein" as used herein refers to a DNA fragment or isolated DNA molecule encoding a protein, or the complementary strand thereto; but, RNA is not excluded, as it is understood in the art that thymidine (T) in a DNA sequence is considered equal to uracil (U) in an RNA sequence. Thus, RNA sequences for use in the invention, e.g., for use in RNA vectors, can be derived from DNA sequences, by thymidine (T) in the DNA sequence being considered equal to uracil (U) in RNA sequences.

A DNA "coding sequence" or a "nucleotide sequence encoding" a particular protein, is a DNA sequence which is transcribed and translated into a polypeptide in vitro or in vivo when placed under the control of appropriate regulatory elements. The boundaries of the coding sequence are determined by a start codon at the 5' (amino) terminus and a translation stop codon at the 3' (carboxy) terminus. A coding sequence can include, but is not limited to, prokaryotic sequences, cDNA from eukaryotic mRNA, genomic DNA sequences from eukaryotic (e.g., mammalian) DNA, and even synthetic DNA sequences. A transcription termination sequence will usually be located 3' to the coding sequence.

"Homology" refers to the percent identity between two polynucleotide or two polypeptide moieties. Two DNA, or two polypeptide sequences are "substantially homologous" to each other when the sequences exhibit at least about 80%, 81%, 82%, 83%, 84%, 85%, 86%, 87%, 88%, 89%, preferably at least about 90%, 91%, 92%, 93%, 94% and most preferably at least about 95%, 96%, 97%, 98%, 99%, 99.5%, 99.9% sequence identity over a defined length of the molecules. As used herein, substantially homologous also refers to sequences showing complete identity (100% sequence identity) to the specified DNA or polypeptide sequence.

Homology can be determined by hybridization of polynucleotides under conditions that form stable duplexes between homologous regions, followed by digestion with single-stranded-specific nuclease(s), and size determination of the digested fragments. DNA sequences that are substantially homologous can be identified in a Southern hybridization experiment under, for example, stringent conditions, as defined for that particular system. Defining appropriate hybridization conditions is within the skill of the art. See, e.g., Sambrook et al. supra; DNA Cloning, supra; Nucleic Acid Hybridization, supra.

Two nucleic acid fragments are considered to be "selectively hybridizable" to a polynucleotide if they are capable of specifically hybridizing to a nucleic acid or a variant thereof or specifically priming a polymerase chain reaction: (i) under typical hybridization and wash conditions, as described, for example, in Sambrook et al. supra and Nucleic Acid Hybridization, supra, (ii) using reduced stringency wash conditions that allow at most about 25-30% basepair mismatches, for example: 2×SSC, 0.1% SDS, room temperature twice, 30 minutes each; then 2×SSC, 0.1% SDS, 37° C. once, 30 minutes; then 2×SSC room temperature twice, 10 minutes each, or (iii) selecting primers for use in typical polymerase chain reactions (PCR) under standard conditions (described for example, in Saiki, et al. (1988) Science 239:487-491).

The term "capable of hybridizing under stringent conditions" as used herein refers to annealing a first nucleic acid to a second nucleic acid under stringent conditions as defined below. Stringent hybridization conditions typically permit the hybridization of nucleic acid molecules having at least 70% nucleic acid sequence identity with the nucleic acid molecule being used as a probe in the hybridization reaction. For example, the first nucleic acid may be a test sample or probe, and the second nucleic acid may be the sense or antisense strand of a nucleic acid or a fragment thereof. Hybridization of the first and second nucleic acids may be conducted under stringent conditions, e.g., high temperature and/or low salt content that tend to disfavor hybridization of dissimilar nucleotide sequences. Alternatively, hybridization of the first and second nucleic acid may be conducted under reduced stringency conditions, e.g. low temperature and/or high salt content that tend to favor hybridization of dissimilar nucleotide sequences. Low stringency hybridization conditions may be followed by high stringency conditions or intermediate medium stringency conditions to increase the selectivity of the binding of the first and second nucleic acids. The hybridization conditions may further include reagents such as, but not limited to, dimethyl sulfoxide (DMSO) or formamide to disfavor still further the hybridization of dissimilar nucleotide sequences. A suitable hybridization protocol may, for example, involve hybridization in 6×SSC (wherein 1×SSC comprises 0.015 M sodium citrate and 0.15 M sodium chloride), at 65° Celsius in an aqueous solution, followed by washing with 1×SSC at 65° C. Formulae to calculate appropriate hybridization and wash conditions to achieve hybridization permitting 30% or less mismatch between two nucleic acid molecules are disclosed, for example, in Meinkoth et al. (1984) Anal. Biochem. 138: 267-284; the content of which is herein incorporated by reference in its entirety. Protocols for hybridization techniques are well known to those of skill in the art and standard molecular biology manuals may be consulted to select a suitable hybridization protocol without undue experimentation. See, for example, Sambrook et al. (2001) Molecular Cloning: A Laboratory Manual, 3rd ed., Cold Spring Harbor Press, the contents of which are herein incorporated by reference in their entirety.

Typically, stringent conditions will be those in which the salt concentration is less than about 1.5 M sodium ion, typically about 0.01 to 1.0 M Na ion concentration (or other salts) from about pH 7.0 to about pH 8.3 and the temperature is at least about 30° Celsius for short probes (e.g., 10 to 50 nucleotides) and at least about 60° C. for long probes (e.g., greater than 50 nucleotides). Stringent conditions may also be achieved with the addition of destabilizing agents such as formamide. Exemplary low stringency conditions include hybridization with a buffer solution of 30 to 35% formamide, 1 M NaCl, 1% SDS (sodium dodecyl sulphate) at 37° Celsius, and a wash in 1-2×SSC at 50 to 55° Celsius. Exemplary moderate stringency conditions include hybridization in 40 to 45% formamide, 1 M NaCl, 1% SDS at 37° Celsius, and a wash in 0.5-1×SSC at 55 to 60° Celsius. Exemplary high stringency conditions include hybridization in 50% formamide, 1 M NaCl, 1% SDS at 37° Celsius, and a wash in 0.1×SSC at 60 to 65° Celsius.

Also encompasses by the present invention is fragments of polypeptide selected from the sequences SEQ ID NOS: 18, 20, 22, 24, 26, 48, 50 and 52. Fragments of polypeptide and epitope determination procedures, such as, generating overlapping peptide libraries (Hemmer B. et al., Immunology Today, 1998, 19 (4), 163-168), Pepscan (Geysen H. M. et al., Proc. Nat. Acad. Sci. USA, 1984, 81 (13), 3998-4002; Geysen H. M. et al., Proc. Nat. Acad. Sci. USA, 1985, 82 (1), 178-182; Van der Zee R. et al., Eur. J. Immunol., 1989, 19 (1), 43-47; Geysen H. M., Southeast Asian J. Trop. Med. Public Health, 1990, 21 (4), 523-533; Multipin® Peptide Synthesis Kits de Chiron) and algorithms (De Groot A. et al., Nature Biotechnology, 1999, 17, 533-561), can be used in the practice of the invention, without undue experimentation.

The polypeptides or fragments thereof are produced advantageously by in vitro expression. Another aspect of the invention is the use of the polynucleotides according to the invention, for the expression and the production of peptides, polypeptides or proteins, or more generally, expression products, e.g., immunogens, antigens or epitopes. In an embodiment, the polypeptides or peptides or proteins encoded by these polynucleotides may be used as subunit immunogens or antigens or epitopes in immunogenic compositions or vaccines. The invention also embraces the immunogenic fragments of these polypeptides, having at least a chain of 8 amino acids of the polypeptide, at least 10, at least 20, such as at least 30, advantageously at least 50 and more advantageously at least 70, e.g., fragments of the polypeptides containing at least 8 contiguous amino acids of the polypeptide, at least 10 contiguous amino acids of the polypeptide, advantageously at least 20, such as at least 30 and more advantageously at least 50 contiguous amino acids of the polypeptide, and even more advantageously at least 70 contiguous amino acids of the polypeptide. Of course, a fragment is less than the entire polypeptide. A fragment can be combined with other polypeptides, e.g., in fusion polypeptides; for instance, a polypeptide of the invention or fragment thereof can be a portion of a fusion polypeptide which includes another portion (another polypeptide) (i.e. fused to glutathione S-transferase gene (GST) (Chanter N et al., Microb. Pathog., 1999, 27(3): 133-143), or to cholera toxin (Sheoran A S et al., Vaccine, 2002, 20(11-12): 1653-1659)), e.g., an immunogenicity-enhancing portion and/or a secretion-enhancing portion such as a lipoprotein portion that enhances immunogenicity, such as a T-cell epitope peptide or a signal or leader sequence portion. Accordingly, the invention envisions the expression of polypeptides, proteins, antigens, immunogens or epitopes—whether herein identified sequences or fragments thereof or those that are heterologous to the vectors of the invention—as fusions, e.g., as a portion of a fusion polypeptide, e.g., a fusion polypeptide that advantageously includes an immuogenicity enhancing portion such as a lipoprotein portion and/or a secretion-enhancing portion such as a signal or leader sequence portion.

As used herein, the term "antigen" or "immunogen" means a substance that induces a specific immune response in a host animal. The antigen may comprise a whole organism, killed, attenuated or live; a subunit or portion of an organism; a recombinant vector containing an insert with immunogenic properties; a piece or fragment of DNA capable of inducing an immune response upon presentation to a host animal; a protein, a polypeptide, a peptide, an epitope, a hapten, or any combination thereof. Alternately, the immunogen or antigen may comprise a toxin or antitoxin.

The term "immunogenic protein or peptide" as used herein also refers includes peptides and polypeptides that are immunologically active in the sense that once administered to the host, it is able to evoke an immune response of the humoral and/or cellular type directed against the protein. Preferably the protein fragment is such that it has substantially the same immunological activity as the total protein. Thus, a protein fragment according to the invention comprises or consists essentially of or consists of at least one epitope or antigenic determinant. The term epitope relates to a protein site able to induce an immune reaction of the humoral type (B cells) and/or cellular type (T cells).

The term "immunogenic protein or peptide" further contemplates deletions, additions and substitutions to the sequence, so long as the polypeptide functions to produce an immunological response as defined herein. In this regard, particularly preferred substitutions will generally be conservative in nature, i.e., those substitutions that take place within a family of amino acids. For example, amino acids are generally divided into four families: (1) acidic—aspartate and glutamate; (2) basic—lysine, arginine, histidine; (3) non-polar—alanine, valine, leucine, isoleucine, proline, phenylalanine, methionine, tryptophan; and (4) uncharged polar—glycine, asparagine, glutamine, cystine, serine threonine, tyrosine. Phenylalanine, tryptophan, and tyrosine are sometimes classified as aromatic amino acids. It is reasonably predictable that an isolated replacement of leucine with isoleucine or valine, or vice versa; an aspartate with a glutamate or vice versa; a threonine with a serine or vice versa; or a similar conservative replacement of an amino acid with a structurally related amino acid, will not have a major effect on the biological activity. Proteins having substantially the same amino acid sequence as the reference molecule but possessing minor amino acid substitutions that do not substantially affect the immunogenicity of the protein are, therefore, within the definition of the reference polypeptide.

The term "epitope" refers to the site on an antigen or hapten to which specific B cells and/or T cells respond. The term is also used interchangeably with "antigenic determinant" or "antigenic determinant site". Antibodies that recognize the same epitope can be identified in a simple immunoassay showing the ability of one antibody to block the binding of another antibody to a target antigen.

An "immunological response" to a composition or vaccine is the development in the host of a cellular and/or antibody-mediated immune response to a composition or vaccine of interest. Usually, an "immunological response" includes but is not limited to one or more of the following effects: the production of antibodies, B cells, helper T cells, and/or cytotoxic T cells, directed specifically to an antigen or antigens included in the composition or vaccine of interest. Preferably, the host will display either a therapeutic or protective immunological response such that resistance to new infection will be enhanced and/or the clinical severity of the disease reduced. Such protection will be demonstrated by either a reduction or lack of symptoms normally displayed by an infected host, a quicker recovery time and/or a lowered viral titer in the infected host.

The terms "immunogenic" protein or polypeptide as used herein also refers to an amino acid sequence which elicits an immunological response as described above. An "immunogenic" protein or polypeptide, as used herein, includes the full-length sequence of the protein, analogs thereof, or immunogenic fragments thereof. By "immunogenic fragment" is meant a fragment of a protein which includes one or more epitopes and thus elicits the immunological response described above. Such fragments can be identified using any number of epitope mapping techniques, well known in the art. See, e.g., *Epitope Mapping Protocols* in Methods in Molecular Biology, Vol. 66 (Glenn E. Morris, Ed., 1996) Humana Press, Totowa, N.J. For example, linear epitopes may be determined by e.g., concurrently synthesizing large numbers of peptides on solid supports, the peptides corresponding to portions of the protein molecule, and reacting the peptides with antibodies while the peptides are still attached to the supports. Such techniques are known in the art and described in, e.g., U.S. Pat. No. 4,708,871; Geysen et al. (1984) Proc. Natl. Acad. Sci. USA 81:3998-4002; Geysen et al. (1986) Molec. Immunol. 23:709-715, all incorporated herein by reference in their entireties. Similarly, conformational epitopes are readily identified by determining spatial conformation of amino acids such as by, e.g., x-ray crystallography and 2-dimensional nuclear magnetic resonance. See, e.g., Epitope Mapping Protocols, supra.

Synthetic antigens are also included within the definition, for example, polyepitopes, flanking epitopes, and other recombinant antigens. See, e.g., Bergmann et al. (1993) Eur. J. Immunol. 23:2777-2781; Bergmann et al. (1996) J. Immunol. 157:3242-3249; Suhrbier, A. (1997) Immunol. and Cell Biol. 75:402-408; Gardner et al. (1998) 12th World AIDS Conference, Geneva, Switzerland, Jun. 28-Jul. 3, 1998. Immunogenic fragments, for purposes of the present invention, will usually include at least about 3 amino acids, preferably at least about 5 amino acids, more preferably at least about 10-15 amino acids, and most preferably 25 or more amino acids, of the molecule. There is no critical upper limit to the length of the fragment, which could comprise nearly the full-length of the protein sequence, or even a fusion protein comprising at least one epitope of the protein.

Accordingly, a minimum structure of a polynucleotide expressing an epitope is that it comprises or consists essentially of or consists of nucleotides to encode an epitope or antigenic determinant of the protein or polyprotein of interest. A polynucleotide encoding a fragment of the total protein or polyprotein, more advantageously, comprises or consists essentially of or consists of a minimum of 21 nucleotides, advantageously at least 42 nucleotides, and preferably at least 57, 87 or 150 consecutive or contiguous nucleotides of the sequence encoding the total protein or polyprotein. Epitope determination procedures, such as, generating overlapping peptide libraries (Hemmer B. et al., Immunology Today, 1998, 19 (4), 163-168), Pepscan (Geysen et al., (1984) Proc. Nat. Acad. Sci. USA, 81, 3998-4002; Geysen et al., (1985) Proc. Nat. Acad. Sci. USA, 82, 178-182; Van der Zee R. et al., (1989) Eur. J. Immunol., 19, 43-47; Geysen H. M., (1990) Southeast Asian J. Trop. Med. Public Health, 21, 523-533; Multipin®. Peptide Synthesis Kits de Chiron) and algorithms (De Groot A. et al., (1999) Nature Biotechnology, 17, 533-561), and in PCT Application Serial No. PCT/US2004/022605 all of which are incorporated herein by reference in their entireties, can be used in the practice of the invention, without undue experimentation. Other documents cited and incorporated herein may also be consulted for methods for determining epitopes of an immunogen or antigen and thus nucleic acid molecules that encode such epitopes.

In one embodiment, the fragments of polypeptide are selected from the sequences SEQ ID NOS: 32, 34, 36, 38, 40, 54, 56 and 58, which are respectively encoded by the nucleotide sequences SEQ ID NOS: 31, 33, 35, 37, 39, 53, 55 and 57. The fragments of polypeptides SEQ ID NOS: 32, 34, 36, 38, 40, 54, 56 and 58 are part of Se50, Se1459, Se595, Se528, Se358, Se1631, Se1681 and Sla, respectively.

The polynucleotides encoding polypeptides according to the present invention, analogs thereof or fragments thereof are inserted into a vector, linked to regulatory elements such as promoter, ribosome binding region and terminator, and start codon and stop codon.

The polypeptides, analogs thereof and fragments thereof can be produced by in vitro expression in host cells. The in vitro expression vectors are expression vectors used for the in vitro expression of proteins in an appropriate cell system. This can be produced in prokaryotic host cells, i.e. in *Escherichia coli* (Mahona F et al., Biochimie 1994, 46(1): 9-14; Watt M A et al., Cell Stress Chaperones 1997, 2(3): 180-90; Frey J Res. Microbiol. 1992, 143(3): 263-9) or in *Lactobacillus* (Seegers J F, Trends Biotechnol. 2002, 20(12): 508-515; Pouwels P H et al, Methods Enzymol. 2001, 336: 369-389), or in eukaryotic host cells, i.e. in yeast (Gerngross T U, Nat. Biotechnol. 2004, 22(11): 1409-1414; Malissard M et al., Glycoconj J. 1999, 16(2): 125-139), in insect cells (Oker-Blom C et al., Brief Funct Genomic Proteomic. 2003, 2(3), 244-253), mammal cells or avian cells.

For *Escherichia coli*, different strains can be used, notably BL21 (DE3) strain (Novagen or Invitrogen; see Hedayati M A et al., Protein Expr Purif, 2005, 43(2): 133-139) Origami2 (DE3) strain (Novagen or Invitrogen), Y1089 (Galan J E et al., Infect Immun, 1987, 55(12): 3181-3187). Vectors are advantageously plasmids, i.e. pGEX plasmids (GE Healthcare), pET plasmids (Novagen or Invitrogen) (Jiang X Y et al., J Biochem Mol. Biol. 2006, 39(1): 22-25; Hedayati M A et al., Protein Expr Purif, 2005, 43(2): 133-139; Jedrzejas M J et al., Protein Expr Purif, 1998, 13(1): 83-89). Vectors can also be a virus, notably a bacteriophage, i.e. lambda-gt11 phage (Galan J E et al., Infect Immun, 1987, 55(12): 3181-3187). Another approach is to use fused genes for the production of chimeric proteins between a *Streptococcus* protein and a *Escherichia coli* protein, notably lipoprotein (Cullen P A et al., Plasmid, 2003, 49(1): 18-29), or with GST (Zhao G et al., Protein Expr Purif, 1999, 16(2): 331-339). The Streptococcal insert can be linked to promoter, i.e. bacteriophage T7 promoter (Yamamoto M et al., FEMS Microbiol Lett, 1995, 132(3): 209-213), signal peptide sequence, i.e. Borrelia burgdorferi outer surface protein A signal peptide (De B K et al., Vaccine, 2000, 18(17): 1811-1821), an *Escherichia coli* major outer membrane lipoprotein signal sequence (Cullen P A et al., Plasmid, 2003, 49(1): 18-29).

For *Lactobacillus*, different strains can be used, notably *Lactobacillus brevis, Lactobacillus plantarum, Lactobacillus casei* (Seegers J F, Trends Biotechnol., 2002, 20(12): 508-515). Promoters and regulatory genes involved in production of sakacin P are suitable for establishing inducible high-level gene expression in *Lactobacillus* (Mathiesen G et al., Lett Appl Microbiol., 2004, 39(2): 137-143), or lactose operon promoter (Oliveira M L et al., FEMS Microbiol Lett., 2003, 227(1): 25-31). Another approach is to use fused genes for the production of chimeric proteins between a *Lactobacillus* protein and a *Streptococcus* protein (Hung J et al., FEMS Microbiol Lett., 2002, 211(1): 71-75).

For in vitro expression in insect cells, vectors are advantageously viruses, i.e. baculoviruses (see, e.g., U.S. Pat. No. 4,745,051; Vialard J. et al., J. Virol., 1990 64 (1), 37-50; Verne A., Virology, 1988, 167, 56-71; Oker-Blom C et al., Brief Funct Genomic Proteomic. 2003, 2(3), 244-253), e.g. *Autographa californica* Nuclear Polyhedrosis Virus AcNPV, and insect cells are Sf9 Spodoptera frugiperda cells (ATCC CRL 1711; see also U.S. Pat. Nos. 6,228,846, 6,103,526). Protein production can take place by the transfection of mammalian cells by plasmids, by replication or expression without productive replication of viral vectors on mammal cells or avian cells. Mammalian cells which can be used are advantageously hamster cells (e.g. CHO or BHK-21) or monkey cells (e.g. COS or VERO) or bovine cells (e.g. MDBK), i.e. culture of EHV-1 vectors in MDBK cells (Ibrahim el S M et al., Microbiol. Immunol., 2004, 48(11): 831-842) or in Vero cells (U.S. Pat. No. 4,110,433), or culture of VEEV replicons in BHK cells (Lee J S et al., Infect. Immun., 2001, 69(9): 5709-5715).

It is understood to one of skill in the art that conditions for culturing in vitro a host cell varies according to the particular gene and that routine experimentation is necessary at times to determine the optimal conditions for culturing a protein depending on the host cell. A "host cell" denotes a prokaryotic or eukaryotic cell that has been genetically altered, or is capable of being genetically altered by administration of an exogenous polynucleotide, such as a recombinant plasmid or vector. When referring to genetically altered cells, the term refers both to the originally altered cell and to the progeny thereof.

The in vitro expression vectors can be introduced into a suitable host cell for replication and amplification. The vectors containing the polynucleotides of interest can be introduced into the host cell by any of a number of appropriate means, including direct uptake, endocytosis, transfection, f-mating, electroporation, transfection employing calcium chloride, rubidium chloride, calcium phosphate, DEAE-dextran, or other substances; microprojectile bombardment; lipofection; and infection (where the vector is infectious, for instance, a retroviral vector). The choice of introducing vectors or polynucleotides will often depend on features of the host cell.

The expressed proteins can be harvested in or from the culture supernatant after, or not after secretion (if there is no secretion a cell lysis typically occurs or is performed), optionally concentrated by concentration methods such as ultrafiltration and/or purified by purification means, such as affinity, ion exchange or gel filtration-type chromatography methods, notably by affinity chromatography, i.e. using Ni NTA Superflow (Qiagen) or Ni Sepharose fastflow (Amersham), or by gel-filtration, i.e. using Sephacryl® or Superdex® (Amersham GE Healthcare).

The polypeptides and fragments thereof can also be obtained by extraction, notably acid extraction or mutanolysin extraction (Boschwitz J S et al., Cornell Vet., 1991, 81(1): 25-36), and purification, notably immunoprecipitation (Erickson E D et al., Can J Comp Med., 1975, 39(2): 110-115), from crude culture of streptococcal bacteria, notably of *Streptococcus equi*.

The polypeptides and fragments thereof can also be synthesised chemically (Luo Y et al., Vaccine 1999, 17(7-8): 821-31).

By "subunit vaccine composition" is meant a composition containing at least one immunogenic polypeptide or a polynucleotide able to express at least one, but not all, antigen derived from or homologous to an antigen from a pathogen of interest. Such a composition is substantially free of intact pathogen cells or particles, or the lysate of such cells or particles. Thus, a "subunit vaccine composition" is prepared from at least partially purified (preferably substantially purified) immunogenic polypeptides from the pathogen, or recombinant analogs thereof. A subunit vaccine composition can comprise the subunit antigen or antigens of interest substantially free of other antigens or polypeptides from the pathogen.

An object of the invention is a subunit immunogenic composition or subunit vaccine comprising at least one polypeptide, analog thereof or fragment thereof according to the invention, and a pharmaceutically acceptable excipient, diluent or vehicle, and optionally an adjuvant and/or a stabilizer.

The subunit immunogenic or vaccine composition can comprise at least one polypeptide selected from the group consisting of sequences SEQ ID NOS: 18, 20, 22, 24, 26, 48, 50 and 52, or analogs thereof, or fragments thereof. The subunit immunogenic or vaccine composition can advantageously comprise two or three or four or five polypeptides selected from the group consisting of sequences SEQ ID NOS: 18, 20, 22, 24, 26, 48, 50 and 52, or analogs thereof, or fragments thereof.

The subunit immunogenic or vaccine composition can comprise at least one polypeptide selected from the group consisting of sequences SEQ ID NOS: 32, 34, 36, 38, 40, 54, 56 and 58, or analogs thereof.

The subunit immunogenic or vaccine composition can advantageously comprise two or three or four or five polypeptides selected from the group consisting of sequences SEQ ID NOS: 32, 34, 36, 38, 40, 54, 56 and 58, or analogs thereof.

Another object of the invention is a recombinant immunogenic composition or vaccine comprising at least one recombinant in vivo expression vector, and a pharmaceutically acceptable excipient, diluent or vehicle, and optionally an adjuvant and/or a stabilizer. The recombinant in vivo expression vectors are vectors comprising polynucleotides or their fragments inserted hereinto and able to express in vivo in the targeted mammal the polypeptide encoded by this polynucleotide or fragment thereof. The vectors can be a polynucleotide vectors or plasmids (EP-A2-1001025; Chaudhuri P Res. Vet. Sci. 2001, 70(3), 255-6) for DNA immunogenic compositions and DNA vaccines, or can be viruses (e.g. herpesvirus such as equine herpesvirus type 1 (Trapp S et al., J. Virol. 2005, 79(9): 5445-5454), equine herpesvirus type 2, equine herpesvirus type 4; poxvirus virus such as vaccinia virus or avipox virus, like fowlpox (U.S. Pat. No. 5,174,993 U.S. Pat. No. 5,505,941 and U.S. Pat. No. 5,766,599) or canarypox (U.S. Pat. No. 5,756,103); adenovirus such as human adenovirus (Chroboczek J et al., Virol. 1992, 186: 280-285); encephalitis virus such as venezuelean equine encephalitis virus (Pushko P et al. Virol. 1997, 239: 389-401; Davis N L et al. J. Virol. 2000, 74: 371-378)) for recombinant viral vector immunogenic compositions and recombinant viral vector vaccines. In a further embodiment, the polynucleotides or their fragments may be inserted into recombinant in vivo expression bacterial vectors, notably into *Salmonella*, to produce live recombinant bacterial immunogenic compositions or vaccines.

The term plasmid covers any DNA transcription unit comprising a polynucleotide according to the invention and the elements necessary for its in vivo expression in a cell or cells of the desired host or target; and, in this regard, it is noted that a supercoiled or non-supercoiled, circular plasmid, as well as a linear form, are intended to be within the scope of the invention. In a specific, non-limiting example, the pVR1020 or 1012 plasmid (VICAL Inc.; Luke C. et al., Journal of Infectious Diseases, 1997, 175, 91-97; Hartikka J. et al., Human Gene Therapy, 1996, 7, 1205-1217) can be utilized as a vector for the insertion of a polynucleotide sequence. The pVR1020 plasmid is derived from pVR1012 and contains the human tPA signal sequence. Each plasmid comprises or contains or consists essentially of, in addition to the polynucleotide or analog thereof or fragment thereof, operably linked to a promoter or under the control of a promoter or dependent upon a promoter. In general, it is advantageous to employ a strong promoter functional in eukaryotic cells. The preferred strong promoter is the immediate early cytomegalovirus promoter (CMV-IE) of human or murine origin, or optionally having another origin such as the rat or guinea pig. The CMV-IE promoter can comprise the actual promoter part, which may or may not be associated with the enhancer part. Reference can be made to EP-A-260 148, EP-A-323 597, U.S. Pat. Nos. 5,168,062, 5,385,839, and 4,968,615, as well as to PCT Application No WO-A-87/03905. The CMV-IE promoter is advantageously a human CMV-IE (Boshart M. et al., Cell, 1985, 41, 521-530) or murine CMV-IE. In more general terms, the promoter has either a viral or a cellular origin. A strong viral promoter other than CMV-IE that may be usefully employed in the practice of the invention is the early/late promoter of the SV40 virus or the LTR promoter of the Rous sarcoma virus. A strong cellular promoter that may be usefully employed in the practice of the invention is the promoter of a gene of the cytoskeleton, such as e.g. the desmin promoter (Kwissa M. et al., Vaccine, 2000, 18, 2337-2344), or the actin promoter (Miyazaki J. et al., Gene, 1989, 79, 269-277). Functional sub fragments of these promoters, i.e., portions of these promoters that maintain an adequate promoting activity, are included within the present invention, e.g. truncated CMV-IE promoters according to PCT Application No. WO-A-98/00166 or U.S. Pat. No. 6,156,567 can be used in the practice of the invention. A promoter in the practice of the invention consequently includes derivatives and sub fragments of a full-length promoter that maintain an adequate promoting activity and hence function as a promoter, preferably promoting activity substantially similar to that of the actual or full-length promoter from which the derivative or sub fragment is derived, e.g., akin to the activity of the truncated CMV-IE promoters of U.S. Pat. No. 6,156, 567 to the activity of full-length CMV-IE promoters. Thus, a CMV-IE promoter in the practice of the invention can comprise or consist essentially of or consist of the promoter portion of the full-length promoter and/or the enhancer portion of the full-length promoter, as well as derivatives and sub fragments. Advantageously, the plasmids comprise or consist essentially of other expression control elements. It is particularly advantageous to incorporate stabilizing sequence(s), e.g., intron sequence(s), preferably the first intron of the hCMV-IE (PCT Application No. WO-A-89/01036), the intron II of the rabbit β-globin gene (van Ooyen et al., Science, 1979, 206, 337-344). As to the polyadenylation signal (polyA) for the plasmids and viral vectors other than poxviruses, use can more be made of the poly(A) signal of the bovine growth hormone (bGH) gene (see U.S. Pat. No. 5,122, 458), or the poly(A) signal of the rabbit β-globin gene or the poly(A) signal of the SV40 virus.

For recombinant vectors based on equine herpesvirus, in particular attenuated strains (i.e. EHV-1 KyA strains (Zhang Y et al., Virology, 2000, 268(2): 482-492)) or attenuated by mutation or deletion of genes involve in pathogenicity (Kirisawa R et al., Vet. Microbiol., 2003, 95(3): 159-174) or by serial culture passages (U.S. Pat. No. 4,110,433) can be used. For EHV-1, the insertion can be made in the intergenic region between ORF 62 and ORF 63 (Ibrahim el S M et al., Microbiol. Immunol., 2004, 48(11): 831-842; Csellner H et al., Arch. Virol., 1998, 143(11): 2215-2231), or in the genes, eventually after a partial or complete deletion of the genes, i.e. in thymidine kinase (TK) gene, in genes 1 or 71 (Kirisawa R et al., Vet. Microbiol., 2003, 95(3): 159-174), in glycoprotein I gene and glycoprotein E gene (Matsumura T. et al., Virology, 1998, 242(1): 68-79), in IR6 protein gene (Osterrieder N et al., Virology, 1996, 217(2): 442-451), in gene 15 (EP-B1-0, 668,355). For EHV-4, the insertion can be made in glycoprotein I gene and glycoprotein E gene (Damiani A M et al., Virus Res., 2000, 67(2): 189-202), in US2 or TK or glycoprotein E gene (U.S. Pat. Nos. 5,741,696; 5,731,188), eventually after a partial or complete deletion of the genes. In one embodiment the polynucleotide to be expressed is inserted under the control of a promoter functional in eukaryotic cells, advantageously a CMV-IE promoter (murine or human). A poly(A) sequence and terminator sequence can be inserted downstream the polynucleotide to be expressed, e.g. bovine growth hormone or a rabbit β-globin gene polyadenylation signal.

For recombinant vector based on poxvirus vector, a vaccinia virus or an attenuated vaccinia virus, (for instance, MVA, a modified Ankara strain obtained after more than 570 passages of the Ankara vaccine strain on chicken embryo fibroblasts; see Stickl & Hochstein-Mintzel, Munch. Med. Wschr., 1971, 113, 1149-1153; Sutter et al., Proc. Natl. Acad. Sci. U.S.A., 1992, 89, 10847-10851; available as ATCC VR-1508; or NYVAC, see U.S. Pat. No. 5,494,807, for instance, Examples 1 to 6 and et seq of U.S. Pat. No. 5,494,807 which discuss the construction of NYVAC, as well as variations of NYVAC with additional ORFs deleted from the Copenhagen strain vaccinia virus genome, as well as the insertion of heterologous coding nucleic acid molecules into sites of this recombinant, and also, the use of matched promoters; see also WO-A-96/40241), an avipox virus or an attenuated avipox virus (e.g., canarypox, fowlpox, dovepox, pigeonpox, quailpox, ALVAC or TROVAC; see, e.g., U.S. Pat. Nos. 5,505,941, 5,494,807) can be used. Attenuated canarypox viruses are described in U.S. Pat. No. 5,756,103 (AL-VAC) and WO-A-01/05934. Reference is also made to U.S. Pat. No. 5,766,599 which pertains to the attenuated fowlpox strain TROVAC. Reference is made to the canarypox available from the ATCC under access number VR-111. Numerous fowlpox virus vaccination strains are also available, e.g. the DIFTOSEC CT strain marketed by MERIAL and the NOBILIS VARIOLE vaccine marketed by INTERVET. For information on the method to generate recombinants thereof and how to administer recombinants thereof, the skilled artisan can refer documents cited herein and to WO-A-90/12882, e.g., as to vaccinia virus mention is made of U.S. Pat. Nos. 4,769,330, 4,722,848, 4,603,112, 5,110,587, 5,494,807, and 5,762,938 inter alia; as to fowlpox, mention is made of U.S. Pat. Nos. 5,174,993, 5,505,941 and 5,766,599 inter alia; as to canarypox mention is made of U.S. Pat. No. 5,756,103 inter alia. When the expression vector is a vaccinia virus, insertion site or sites for the polynucleotide or polynucleotides to be expressed are advantageously at the thymidine kinase (TK) gene or insertion site, the hemagglutinin (HA) gene or insertion site, the region encoding the inclusion body of the A type (ATI); see also documents cited herein, especially those pertaining to vaccinia virus. In the case of canarypox, advantageously the insertion site or sites are ORF(s) C3, C5 and/or C6; see also documents cited herein, especially those pertaining to canarypox virus. In the case of fowlpox, advantageously the insertion site or sites are ORFs F7 and/or F8; see also documents cited herein, especially those pertaining to fowlpox virus. The insertion site or sites for MVA virus area advantageously as in various publications, including Carroll M. W. et al., Vaccine, 1997, 15 (4), 387-394; Stittelaar K. J. et al., J. Virol., 2000, 74 (9), 4236-4243; Sutter G. et al., 1994, Vaccine, 12 (11), 1032-1040; and, in this regard it is also noted that the complete MVA genome is described in Antoine G., Virology, 1998, 244, 365-396, which enables the skilled artisan to use other insertion sites or other promoters. Advantageously, the polynucleotide to be expressed is inserted under the control of a specific poxvirus promoter, e.g., the vaccinia promoter 7.5 kDa (Cochran et al., J. Virology, 1985, 54, 30-35), the vaccinia promoter I3L (Riviere et al., J. Virology, 1992, 66, 3424-3434), the vaccinia promoter HA (Shida, Virology, 1986, 150, 451-457), the cowpox promoter ATI (Funahashi et al., J. Gen. Virol., 1988, 69, 35-47), the vaccinia promoter H6 (Taylor J. et al., Vaccine, 1988, 6, 504-508; Guo P. et al. J. Virol., 1989, 63, 4189-4198; Perkus M. et al., J. Virol., 1989, 63, 3829-3836), inter alia.

For recombinant vector based on adenovirus vector, a human adenovirus (HAV), advantageously, a human adenovirus serotype 5 (Ad5) vector, an E1-deleted and/or disrupted adenovirus, an E3-deleted and/or disrupted adenovirus or an E1- and E3-deleted and/or disrupted adenovirus can be used. Optionally, E4 may be deleted and/or disrupted from any of the adenoviruses described above. For example, the human Ad5 vectors described in Yarosh et al. and Lutze-Wallace et al. can be used (see, e.g., Yarosh et al., Vaccine. 1996 September; 14(13):1257-64 and Lutze-Wallace et al., Biologicals. 1995 December; 23(4):271-7). In one embodiment the viral vector is a human adenovirus, in particular a serotype 5 adenovirus, rendered incompetent for replication by a deletion in the E1 region of the viral genome. The deleted adenovirus is propagated in E1-expressing 293 cells or PER cells, in particular PER.C6 (F. Falloux et al Human Gene Therapy 1998, 9, 1909-1917). The human adenovirus can be deleted in the E3 region eventually in combination with a deletion in the E1 region (see, e.g. J. Shriver et al. Nature, 2002, 415, 331-335, F. Graham et al Methods in Molecular Biology Vol 0.7: Gene Transfer and Expression Protocols Edited by E. Murray, The Human Press Inc, 1991, p 109-128; Y. Ilan et al Proc. Natl. Acad. Sci. 1997, 94, 2587-2592; S. Tripathy et al Proc. Natl. Acad. Sci. 1994, 91, 11557-11561; B. Tapnell Adv. Drug Deliv. Rev. 1993, 12, 185-199; X. Danthinne et al Gene Therapy 2000, 7, 1707-1714; K. Berkner Bio Techniques 1988, 6, 616-629; K. Berkner et al Nucl. Acid Res. 1983, 11, 6003-6020; C. Chavier et al J. Virol. 1996, 70, 4805-4810). The insertion sites can be the E1 and/or E3 loci eventually after a partial or complete deletion of the E1 and/or E3 regions. Advantageously, when the expression vector is an adenovirus, the polynucleotide to be expressed is inserted under the control of a promoter functional in eukaryotic cells, such as a strong promoter, preferably a cytomegalovirus immediate-early gene promoter (CMV-IE promoter). The CMV-IE promoter is advantageously of murine or human origin. The promoter of the elongation factor 1α can also be used. A muscle specific promoter can also be used (X. Li et al Nat. Biotechnol. 1999, 17, 241-245). Strong promoters are also discussed herein in relation to plasmid vectors. A poly (A) sequence and terminator sequence can be inserted downstream of the polynucleotide to be expressed, e.g. a bovine growth hormone gene or a rabbit β-globin gene polyadenylation signal.

For recombinant vector based on Encephalitis virus, a venezuelean equine encephalitis virus (VEEV) can be used (Nelson E L et al., Breast Cancer Res. Treat., 2003, 82(3): 169-183), in particular as a replicon, that is to say as a self-replicating RNA containing all of the VEEV non-structural genes and a multiple-cloning site in place of the VEEV structural genes (Lee J S et al., Infect. Immun., 2003, 71(3): 1491-1496; Velders M P et al., Cancer Res., 2001, 61(21): 7861-7867). The polynucleotides to be expressed are inserted into this multiple-cloning site, optionally linked to the nucleotide sequence encoding a secretory sequence or a tissue plasminogen activator secretory sequence. The polynucleotides to be expressed can also be inserted downstream of the subgenomic 26S promoter in place of the viral VEEV structural genes (Lee J S et al., Infect. Immun., 2001, 69(9): 5709-5715; Pushko P et al., Vaccine, 2000, 19(1): 142-153).

For recombinant vectors based on bacteria, *Salmonella*, notably *Salmonella typhimurium* (Yang X L et al., Biomed. Environ. Sci., 2005, 18(6): 411-418; Dunstan S J et al., FEMS Immunol. Med. Microbiol., 2003, 37(2-3): 111-119), *Salmonella typhi* (Santiago-Machuca A E et al., Plasmid., 2002, 47(2): 108-119) can be used. The polynucleotides to be expressed can be inserted into the flagellin gene of *Salmonella* (Chauhan N et al., Mol Cell Biochem., 2005, 276(1-2): 1-6), or into the aroC gene (Santiago-Machuca A E et al., Plasmid., 2002, 47(2): 108-119). The polynucleotides to be expressed can also be inserted under the control of the anaerobically inducible nirB promoter (Santiago-Machuca A E et al., Plasmid., 2002, 47(2): 108-119).

The recombinant immunogenic or vaccine composition can contain at least one recombinant expression vector comprising at least one polynucleotide encoding a polypeptide selected from the group consisting of sequences SEQ ID NOS: 18, 20, 22, 24, 26, 48, 50 and 52, or analogs thereof or fragments thereof. The recombinant immunogenic or vaccine composition can contain at least one recombinant expression vector comprising at least one polynucleotide encoding a polypeptide selected from the group consisting of sequences SEQ ID NOS: 32, 34, 36, 38, 40, 54, 56 and 58, or analogs thereof. The recombinant immunogenic or vaccine composition can advantageously contain at least one recombinant expression vector comprising at least one polynucleotide encoding two or three or four or five polypeptides selected from the group consisting of sequences SEQ ID NOS: 32, 34, 36, 38, 40, 54, 56 and 58, or analogs thereof.

The vectors of the invention may further comprise at least one heterologous polynucleotide. This is useful for reproducing or replicating heterologous polynucleotides and/or for expression of heterologous polynucleotides, either in vivo or in vitro. Such vectors are also useful for preparing multivalent immunogenic or vaccine compositions, notably multivalent DNA immunogenic compositions or vaccines and multivalent recombinant viral vector immunogenic compositions or vaccines. The heterologous nucleic acid sequence advantageously codes for an immunogen, antigen or epitope from a pathogenic viral, parasitic or bacterial agent, such bacterial agent is different from the streptococcal bacteria at the origin of the polynucleotides encoding the polypeptides according to the invention. This heterologous sequence may encode an immunogen, antigen or epitope from western equine encephalitis virus (WEEV), eastern equine encephalitis virus (EEEV), venezuelean equine encephalitis virus (VEEV), equine influenza virus, equine herpesvirus type 1 (EHV-1), equine herpesvirus type 2 (EHV-2), equine herpesvirus type 4 (EHV-4), Equine Artheritis virus (EAV), West Nile virus (WNV), tetanus, rhodococcus. In a particular embodiment, the heterologous sequence may encode an immunogen, antigen or epitope from equine influenza virus and from EHV-1 and/or EHV-4. An immunogen or antigen is a protein or polypeptide able to induce an immune response against the pathogenic agent or a secreted antigen of the pathogenic agent, and contains one or more epitopes; an epitope is a peptide or polypeptide which is able to induce an immune response against the pathogenic agent or a secreted antigen of the pathogenic agent.

Optionally, the subunit immunogenic composition or vaccine of the invention can be combined with one or more immunogens, antigens or epitopes selected from other pathogenic micro-organisms or viruses to form a multivalent subunit immunogenic composition or vaccine. For the equine, such a multivalent subunit immunogenic composition or vaccine may comprises at least one polypeptide according to the present invention and at least one immunogen, antigen or epitope from WEEV, EEEV, VEEV, equine influenza virus, EHV-1, EHV-4, EAV, WNV, tetanus, *rhodococcus*. In a particular embodiment, such a multivalent subunit immunogenic composition or vaccine may comprises at least one polypeptide according to the present invention and at least one immunogen, antigen or epitope from equine influenza virus and from EHV-1 and/or EHV-4.

The pharmaceutically or veterinary acceptable excipient, diluent or vehicle may be water or saline, buffer but it may, for example, also comprise *Streptococcus* culture medium.

The pharmaceutically or veterinarily acceptable carriers or vehicles or excipients are well known to the one skilled in the art. For example, a pharmaceutically or veterinarily acceptable carrier or vehicle or excipient can be a 0.9% NaCl (e.g., saline) solution or a phosphate buffer. Other pharmaceutically or veterinarily acceptable carrier or vehicle or excipients that can be used for methods of this invention include, but are not limited to, poly-(L-glutamate) or polyvinylpyrrolidone. The pharmaceutically or veterinarily acceptable carrier or vehicle or excipients may be any compound or combination of compounds facilitating the administration of the vector (or protein expressed from an inventive vector in vitro); advantageously, the carrier, vehicle or excipient may facilitate transfection and/or improve preservation of the vector (or protein). Doses and dose volumes are herein discussed in the general description and can also be determined by the skilled artisan from this disclosure read in conjunction with the knowledge in the art, without any undue experimentation.

The cationic lipids containing a quaternary ammonium salt which are advantageously but not exclusively suitable for plasmids, are advantageously those having the following formula:

$$R_1-O-CH_2-CH(OR_1)-CH_2-N^+(CH_3)(CH_3)-R_2-X$$

in which $R_1$ is a saturated or unsaturated straight-chain aliphatic radical having 12 to 18 carbon atoms, $R_2$ is another aliphatic radical containing 2 or 3 carbon atoms and X is an amine or hydroxyl group, e.g. the DMRIE. In another embodiment the cationic lipid can be associated with a neutral lipid, e.g. the DOPE.

Among these cationic lipids, preference is given to DMRIE (N-(2-hydroxyethyl)-N,N-dimethyl-2,3-bis(tetradecyloxy)-1-propane ammonium; WO96/34109), advantageously associated with a neutral lipid, advantageously DOPE (dioleoyl-phosphatidyl-ethanol amine; Behr J. P., 1994, Bioconjugate Chemistry, 5, 382-389), to form DMRIE-DOPE.

Advantageously, the plasmid mixture with the adjuvant is formed extemporaneously and advantageously contemporaneously with administration of the preparation or shortly before administration of the preparation; for instance, shortly before or prior to administration, the plasmid-adjuvant mixture is formed, advantageously so as to give enough time prior to administration for the mixture to form a complex, e.g. between about 10 and about 60 minutes prior to administration, such as approximately 30 minutes prior to administration.

When DOPE is present, the DMRIE:DOPE molar ratio is advantageously about 95:about 5 to about 5:about 95, more advantageously about 1:about 1, e.g., 1:1.

The DMRIE or DMRIE-DOPE adjuvant:plasmid weight ratio can be between about 50:about 1 and about 1:about 10, such as about 10:about 1 and about 1:about 5, and advantageously about 1:about 1 and about 1:about 2, e.g., 1:1 and 1:2.

The immunogenic compositions and vaccines according to the invention may comprise or consist essentially of one or more adjuvants. Suitable adjuvants for use in the practice of the present invention are (1) polymers of acrylic or methacrylic acid, maleic anhydride and alkenyl derivative polymers, (2) immunostimulating sequences (ISS), such as oligodeoxyribonucleotide sequences having one or more non-methylated CpG units (Klinman et al., Proc. Natl. Acad. Sci., USA, 1996, 93, 2879-2883; WO98/16247), (3) an oil in water emulsion, such as the SPT emulsion described on p 147 of "Vaccine Design, The Subunit and Adjuvant Approach" published by M. Powell, M. Newman, Plenum Press 1995, and the emulsion MF59 described on p 183 of the same work, (4) cation lipids containing a quaternary ammonium salt, e.g., DDA (5) cytokines, (6) aluminum hydroxide or aluminum phosphate, (7) saponin or (8) other adjuvants discussed in any document cited and incorporated by reference into the instant application, or (9) any combinations or mixtures thereof.

The oil in water emulsion (3), which is especially appropriate for viral vectors, can be based on: light liquid paraffin oil (European pharmacopoeia type), isoprenoid oil such as squalane, squalene, oil resulting from the oligomerization of alkenes, e.g. isobutene or decene, esters of acids or alcohols having a straight-chain alkyl group, such as vegetable oils, ethyl oleate, propylene glycol, di(caprylate/caprate), glycerol tri(caprylate/caprate) and propylene glycol dioleate, or esters of branched, fatty alcohols or acids, especially isostearic acid esters.

The oil is used in combination with emulsifiers to form an emulsion. The emulsifiers may be nonionic surfactants, such as: esters of on the one hand sorbitan, mannide (e.g. anhydromannitol oleate), glycerol, polyglycerol or propylene glycol and on the other hand oleic, isostearic, ricinoleic or hydroxystearic acids, said esters being optionally ethoxylated, or polyoxypropylene-polyoxyethylene copolymer blocks, such as Pluronic, e.g., L121. Among the type (1) adjuvant polymers, preference is given to polymers of crosslinked acrylic or methacrylic acid, especially crosslinked by polyalkenyl ethers of sugars or polyalcohols. These compounds are known under the name carbomer (Pharmeuropa, vol. 8, no. 2, June 1996). One skilled in the art can also refer to U.S. Pat. No. 2,909,462, which provides such acrylic polymers crosslinked by a polyhydroxyl compound having at least three hydroxyl groups, preferably no more than eight such groups, the hydrogen atoms of at least three hydroxyl groups being replaced by unsaturated, aliphatic radicals having at least two carbon atoms. The preferred radicals are those containing 2 to 4 carbon atoms, e.g. vinyls, allyls and other ethylenically unsaturated groups. The unsaturated radicals can also contain other substituents, such as methyl. Products sold under the name Carbopol (BF Goodrich, Ohio, USA) are especially suitable. They are crosslinked by allyl saccharose or by allyl pentaerythritol. Among them, reference is made to Carbopol 974P, 934P and 971P. As to the maleic anhydride-alkenyl derivative copolymers, preference is given to EMA (Monsanto), which are straight-chain or crosslinked ethylene-maleic anhydride copolymers and they are, for example, crosslinked by divinyl ether. Reference is also made to J. Fields et al., Nature 186: 778-780, Jun. 4, 1960.

With regard to structure, the acrylic or methacrylic acid polymers and EMA are preferably formed by basic units having the following formula:

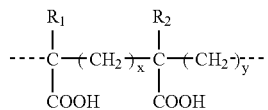

in which:
$R_1$ and $R_2$, which can be the same or different, represent H or $CH_3$
x=0 or 1, preferably x=1
y=1 or 2, with x+y=2.
For EMA, x=0 and y=2 and for carbomers x=y=1.

These polymers are soluble in water or physiological salt solution (20 g/l NaCl) and the pH can be adjusted to 7.3 to 7.4, e.g., by soda (NaOH), to provide the adjuvant solution in which the expression vector(s) can be incorporated. The polymer concentration in the final vaccine composition can range between 0.01 and 1.5% w/v, advantageously 0.05 to 1% w/v and preferably 0.1 to 0.4% w/v.

The cytokine or cytokines (5) can be in protein form in the immunogenic or vaccine composition, or can be co-expressed in the host with the immunogen or immunogens or epitope(s) thereof. Preference is given to the co-expression of the cytokine or cytokines, either by the same vector as that expressing the immunogen or immunogens or epitope(s) thereof, or by a separate vector therefor.

The invention comprehends preparing such combination compositions; for instance by admixing the active components, advantageously together and with an adjuvant, carrier, cytokine, and/or diluent.

Cytokines that may be used in the present invention include, but are not limited to, granulocyte colony stimulating factor (G-CSF), granulocyte/macrophage colony stimulating factor (GM-CSF), interferon α (IFN α), interferon β (IFN β), interferon γ, (IFN γ), interleukin-1α (IL-1 α), interleukin-1 β (IL-1 β), interleukin-2 (IL-2), interleukin-3 (IL-3), interleukin-4 (IL-4), interleukin-5 (IL-5), interleukin-6 (IL-6), interleukin-7 (IL-7), interleukin-8 (IL-8), interleukin-9 (IL-9), interleukin-10 (IL-10), interleukin-11 (IL-11), interleukin-12 (IL-12), tumor necrosis factor α (TNF α), tumor necrosis factor β (TNF β), and transforming growth factor β (TGF β). It is understood that cytokines can be co-administered and/or sequentially administered with the immunogenic or vaccine composition of the present invention. Thus, for instance, the vaccine of the instant invention can also contain an exogenous nucleic acid molecule that expresses in vivo a suitable cytokine, e.g., a cytokine matched to this host to be vaccinated or in which an immunological response is to be elicited (for instance, a canine cytokine for preparations to be administered to dogs).

Advantageously, the pharmaceutical and/or therapeutic compositions and/or formulations according to the invention comprise or consist essentially of or consist of an effective quantity to elicit a therapeutic response of one or more expression vectors and/or polypeptides as discussed herein; and, an effective quantity can be determined from this disclosure, including the documents incorporated herein, and the knowledge in the art, without undue experimentation.

The recombinant viral vector immunogenic compositions and the recombinant viral vector vaccines according to the invention may be freeze-dried advantageously with a stabiliser. Freeze-drying can be done according to well-known standard freeze-drying procedures. The pharmaceutically or veterinary acceptable stabilisers may be carbohydrates (e.g. sorbitol, mannitol, lactose, sucrose, glucose, dextran, trehalose), sodium glutamate (Tsvetkov T et al., Cryobiology 1983, 20(3): 318-23; Israeli E et al., Cryobiology 1993, 30(5): 519-23), proteins such as peptone, albumin, lactalbumin or casein, protein containing agents such as skimmed milk (Mills C K et al., Cryobiology 1988, 25(2): 148-52; Wolff E et al., Cryobiology 1990, 27(5): 569-75), and buffers (e.g. phosphate buffer, alkaline metal phosphate buffer). An adjuvant may be used to make soluble the freeze-dried preparations.

Further the present invention concerns the use of at least one polypeptide having an amino acid sequence as shown in SEQ ID NOS: 18, 20, 22, 24, 26, 48, 50 and 52, or analogs thereof or fragments thereof, for the treatment and/or vaccination of mammals against streptococcal infection, notably of equine, canine and human species. In one embodiment, these fragments are selected from the group consisting of sequences SEQ ID NOS: 32, 34, 36, 38, 40, 54, 56 and 58, or analogs thereof. A particular embodiment concerns the use of at least one polypeptide selected from the group consisting of sequences SEQ ID NOS: 18, 20, 22, 24, 26, 32, 34, 36, 38, 40, 48, 50, 52, 54, 56 and 58, or analogs thereof, for the treatment and/or vaccination of equines against strangles disease. A preferred embodiment concerns the use of at least one polypeptide selected from the group consisting of sequences SEQ ID NOS: 32, 34, 36, 38, 40, 54, 56 and 58, or analogs thereof, for the treatment and/or vaccination of equines against strangles disease.

A further embodiment concerns the use of at least one polypeptide having an amino acid sequence as shown in SEQ ID NOS: 18, 20, 22, 24, 26, 48, 50 and 52, or analogs thereof or fragments thereof, for the preparation of a subunit vaccine protecting equine against *Streptococcus equi* infection. This further embodiment preferably the use of at least one polypeptide having an amino acid sequence as shown in SEQ ID NOS: 32, 34, 36, 38, 40, 54, 56 and 58, or analogs thereof, for the preparation of a subunit vaccine protecting equine against *Streptococcus equi* infection.

Another further embodiment concerns the use of at least one recombinant vector and of at least one polynucleotide inserted therein coding for a polypeptide having an amino acid sequence as shown in SEQ ID NOS: 18, 20, 22, 24, 26, 48, 50 and 52, or an analog thereof or a fragment thereof, and said vector is able to express in vivo this polypeptide in a mammal susceptible to streptococcal infection, for the preparation of a recombinant vaccine protecting equine against *Streptococcus equi* infection. This further embodiment concerns preferably the use of at least one recombinant vector and of at least one polynucleotide inserted therein coding for a polypeptide having an amino acid sequence as shown in SEQ ID NOS: 32, 34, 36, 38, 40, 54, 56 and 58, or an analog thereof, and said vector is able to express in vivo this polypeptide in a mammal susceptible to streptococcal infection, for the preparation of a recombinant vaccine protecting equine against *Streptococcus equi* infection.

An additional embodiment concerns the use of at least one recombinant vector and at least one polynucleotide inserted therein, wherein said polynucleotide has a nucleotide sequence as shown in SEQ ID NOS: 17, 19, 21, 23, 25, 31, 33, 35, 37, 39, 47, 49, 51, 53, 55 and 57, or an analog thereof, and said vector is able to express in vivo the polypeptide encoded by said polynucleotide in a mammal susceptible to streptococcal infection, for the preparation of a recombinant vaccine protecting equine against *Streptococcus equi* infection.

In particular, combinations of polypeptides to be used for the treatment and/or vaccination of equine against strangles disease are combination of at least one polypeptide selected from a first group of polypeptides consisting of SEQ ID NOS: 18, 20, 22, 24, 26, 32, 34, 36, 38, 40, 48, 50, 52, 54, 56 and 58, or analogs thereof or combinations thereof, and at least one another *Streptococcus equi* immunogen, which is not present in this first group, notably at least one immunogen selected from a second group of polypeptides consisting of FNZ protein, EAG protein, SFS protein, SEC protein, SFSC1 fragment, FNZN fragment, SEC2.16 fragment, SEC1.18 fragment, SclC1 fragment (WO-A-2004/032957) and SEQ ID NOS: 28, 30 or analogs thereof or fragments thereof, or combinations thereof. In preferred combinations of polypeptides, this first group consists of SEQ ID NOS: 32, 34, 36, 38, 40, 54, 56 and 58, or analogs thereof or combinations thereof. Further the present invention also concerns the use of these combinations of peptides for the preparation of subunit vaccines protecting equines against *Streptococcus equi* infection. In these embodiments, the use of polypeptides may be replaced by the use of recombinant expression vectors according to the present invention comprising at least one polynucleotide encoding said polypeptides. In particular, at least one recombinant expression vector comprising at least one polynucleotide encoding at least one polypeptide selected from a first group of polypeptides consisting of SEQ ID NOS: 18, 20, 22, 24, 26, 32, 34, 36, 38, 40, 48, 50, 52, 54, 56 and 58, or analogs thereof, and at least one polynucleotide encoding at least one another *Streptococcus equi* immunogen, which is not present in this first group, notably at least one immunogen selected from a second group of polypeptides consisting of FNZ protein, EAG protein, SFS protein, SEC protein, SFSC1 fragment, FNZN fragment, SEC2.16 fragment, SEC1.18 fragment, SclC1 fragment (WO-A-2004/032957) and SEQ ID NOS: 28, 30 or analogs thereof or fragments thereof, or combinations thereof, are used for the treatment and/or vaccination of equines against strangles disease. In a preferred embodiment, this first group consists of SEQ ID NOS: 32, 34, 36, 38, 40, 54, 56 and 58, or analogs thereof or combinations thereof. Further the present invention also concerns the use of these recombinant expression vectors for the preparation of recombinant vaccines protecting equines against *Streptococcus equi* infection.

In a particular embodiment, the combinations of polypeptides to be used for the treatment and/or vaccination of equine against strangles disease are combination of polypeptides SEQ ID NOS: 52, 48, 22 and 26, or analogs thereof, or fragments thereof. In a more preferred embodiment, the combinations of polypeptides to be used for the treatment and/or vaccination of equine against strangles disease are combination of polypeptides SEQ ID NOS: 58, 54, 36 and 40, or analogs thereof.

In a particular embodiment, the combinations of polypeptides to be used for the treatment and/or vaccination of equine against strangles disease are combination of polypeptides SEQ ID NOS: 52, 48, 22, 26 and 50, or analogs thereof, or fragments thereof. In a more preferred embodiment, the combinations of polypeptides to be used for the treatment and/or vaccination of equine against strangles disease are combination of polypeptides SEQ ID NOS: 58, 54, 36, 40 and 56, or analogs thereof.

In a particular embodiment, the combinations of polypeptides to be used for the treatment and/or vaccination of equine against strangles disease are combination of polypeptides SEQ ID NOS: 52, 48, 22, 26 and 20, or analogs thereof, or fragments thereof. In a more preferred embodiment, the combinations of polypeptides to be used for the treatment and/or vaccination of equine against strangles disease are combination of polypeptides SEQ ID NOS: 58, 54, 36, 40 and 34, or analogs thereof.

In a particular embodiment, the combinations of polypeptides to be used for the treatment and/or vaccination of equine against strangles disease are combination of polypeptides SEQ ID NOS: 52, 48, 22, 26 and 18, or analogs thereof, or fragments thereof. In a more preferred embodiment, the combinations of polypeptides to be used for the treatment and/or vaccination of equine against strangles disease are combination of polypeptides SEQ ID NOS: 58, 54, 36, 40 and 32, or analogs thereof.

Further the present invention relates to methods to immunise against or to prevent streptococcal infection in mammals, preferably in equine, canine and in human species. According to these methods, (1) a subunit immunogenic composition or vaccine of the present invention, or (2) a recombinant immunogenic composition or vaccine of the present invention, or their combinations, are administered. Of course, embodiments of the invention may be employed with other vaccines or immunogenic compositions that are not of the invention, e.g., in prime-boost processes, such as where a vaccine or immunogenic composition of the invention is administered first and a different vaccine or immunogenic composition is administered thereafter, or vice versa. Particular prime-boost processes may be that a subunit vaccine or immunogenic composition of the invention is administered first and a recombinant vaccine or immunogenic composition of the invention is administered thereafter, or vice versa.

The administration may be notably made by intramuscular (IM), intradermal (ID), subcutaneous (SC) or transdermal injection or via intranasal, intratracheal, oral administration, or through the ears or the lip. The immunogenic composition or the vaccine according to the invention is administered by syringe, a syringe with a microneedle (i.e. BD™ Intradermal Delivery System of Becton, Dickinson and Company, Franklin Lakes, N.J., USA), needleless apparatus (like for example Pigjet, Avijet, Dermojet or Biojector (Bioject, Oreg., USA), see U.S. Pat. No. 2006/0034867) or a spray. The administration is preferably made by IM injection with a syringe, or by transdermal injection with a needleless apparatus or with a syringe with a microneedle (i.e. BD™ Intradermal Delivery System), or by intranasal or oral administration with a spray, i.e. a liquid nebulisation of a vaccine of the invention, or by oral or nasal administration of a micronized powder of a freeze-dried vaccine according to the invention.

The quantity of immunogenic compositions or vaccines can be determined and optimised by the skilled person, without undue experimentation from this disclosure and the knowledge in the art. Generally an animal (including a human) may be administered approximately $10^4$-$10^9$ CFUs, advantageously approximately $10^5$-$10^8$ CFUs and more advantageously approximately $10^6$-$10^8$ CFUs in a single dosage unit of recombinant viral immunogenic compositions or vaccines of the present invention; approximately 10 ng-1 mg, advantageously approximately 100 ng-500 μg and more advantageously approximately 1 μg-250 μg per plasmid type in a single dosage unit of recombinant DNA immunogenic compositions or vaccines of the present invention; approximately 5 μg-1 mg, advantageously approximately 50 μg-500 μg and more advantageously approximately 100 μg-200 μg in a single dosage unit of subunit immunogenic compositions or vaccines of the present invention.

In the case of therapeutic and/or pharmaceutical compositions based on a plasmid vector, a dose can comprise, consist essentially of or consist of, in general terms, about in 1 μg to about 2000 μg, advantageously about 50 μg to about 1000 μg and more advantageously from about 100 μg to about 800 μg of plasmid expressing the antigen, epitope, immunogen, peptide or polypeptide of interest. When the therapeutic and/or pharmaceutical compositions based on a plasmid vector is administered with electroporation the dose of plasmid is generally between about 0.1 μg and 1 mg, advantageously between about 1 μg and 100 μg, advantageously between about 2 μg and 50 μg. The dose volumes can be between about 0.1 and about 2 ml, advantageously between about 0.2 and about 1 ml. These doses and dose volumes are suitable for the treatment mammalian target species.

The volume of one single dosage unit by syringe can be between about 0.2 ml and about 5.0 ml and advantageously between about 0.5 ml and about 2.0 ml and more advantageously about 1.0 ml. The volume of one single dosage unit by needleless apparatus can be between about 0.1 ml and about 1.0 ml and advantageously between about 0.2 ml and about 0.5 ml. The volume of one single dosage unit by liquid spray can be between about 2.0 ml and about 10.0 ml and advantageously about 5.0 ml (for powder spray, the quantities administered are corresponding to the equivalent volumes).

In a particular method, foals, that is to say horses of 2 to 6 months old and preferably 3 to 4 months old, are vaccinated with subunit vaccines of the present invention, adjuvanted with CTB and/or CTA and/or Carbopol®, via the intranasal or oral route.

In another particular method, foals are vaccinated with recombinant viral vaccines of the present invention, adjuvanted or not with Carbopol®, via the oral route with a spray and liquid nebulisation. Preferably, the viral vectors of these recombinant viral vaccines are EHV-4 or EHV-2, or EHV-1.

In another particular method, foals are vaccinated with recombinant viral vaccines of the present invention, via the lips with a syringe. Preferably, the viral vectors of these recombinant viral vaccines are EHV-4 or EHV-2 or EHV-1.

Preferably for the vaccination of horses and mares, two administrations of subunit vaccines of the present invention, adjuvanted with Carbopol® and/or CpG, and or emulsion are made by IM injection with a syringe. Boost administrations may be injected every 6 months or annually. For pregnant mares, a boost administration may be injected 2 to 4 weeks before the expected foaling date.

Polypeptides of the invention and fragments thereof may also be used in therapy.

The polypeptides and fragments may also be used as reagents in antibody-antigen reactions. Accordingly, another aspect of the invention is thus a diagnostic method and/or kit for detecting infection by the streptococcal bacterium. Kits, e.g. ELISA, can include at least one polypeptide or fragment according to the invention (e.g., at least one polypeptide identified by sequence herein or a fragment thereof as herein discussed).

Antibodies against the herein polypeptides or fragments (e.g., polypeptides identified by sequence herein or fragments thereof as herein discussed) can be used as a diagnostic reagent or in passive immunization or vaccination or in therapy. The amounts of antibody administered in passive immunization can be the same as or analogous to amounts used in the art, such that from the knowledge in the art, the skilled artisan can practice passive immunization without undue experimentation.

Proteins encoded by the novel viruses of the present invention, or their fragments, can be used to produce antibodies, both polyclonal and monoclonal. If polyclonal antibodies are desired, a selected mammal, (e.g., mouse, rabbit, goat, horse, etc.) is immunized with an antigen of the present invention, or its fragment, or a mutated antigen. Serum from the immunized animal is collected and treated according to known procedures. See, e.g., Jurgens et al. (1985) J. Chrom. 348: 363-370. If serum containing polyclonal antibodies is used, the polyclonal antibodies can be purified by immunoaffinity chromatography, using known procedures.

Another aspect of the invention is an antibody preparation comprising an antibody specific to a polypeptide or a fragment according to the invention and methods of diagnosis using the same. With respect to an antibody specific to a polypeptide, it is meant that the antibody binds preferentially to the polypeptide, e.g., the antibody binds to the polypeptide and not to other polypeptides or has a specificity to the polypeptide that is acceptably particular to the polypeptide such that the antibody can be used to isolate the polypeptide from a sample or detect its presence in a sample with no more than 5% false positives, using techniques known in the art or discussed in documents cited herein, including Sambrook, infra.

Antibodies can be polyclonal or monoclonal.

If polyclonal antibodies are desired, a selected animal (e.g. mouse, rabbit, goat, horse, etc.) is immunized with a polypeptide or a fragment. Serum from the immunized animal is collected and treated according to known procedures and possibly purified. See, e.g. Jurgens et al. J. Chrom., 1985, 348: 363-370.

Monoclonal antibodies to the proteins and to the fragments thereof, can also be readily produced by one skilled in the art. The general methodology for making monoclonal antibodies by using hybridoma technology is well known. Immortal antibody-producing cell lines can be created by cell fusion, and also by other techniques such as direct transformation of B lymphocytes with oncogenic DNA, or transfection with Epstein-Barr virus. See, e.g., M. Schreier et al., *Hybridoma Techniques* (1980); Hammerling et al., *Monoclonal Antibodies and T-cell Hybridomas* (1981); Kennett et al., *Monoclonal Antibodies* (1980); see also U.S. Pat. Nos. 4,341,761; 4,399,121; 4,427,783; 4,444,887; 4,452,570; 4,466,917; 4,472,500, 4,491,632; and 4,493,890. Panels of monoclonal antibodies produced against the desired protein, or fragment thereof, can be screened for various properties; i.e., for isotype, epitope, affinity, etc. Monoclonal antibodies are useful in purification, using immunoaffinity techniques, of the individual antigens which they are directed against. Both polyclonal and monoclonal antibodies can also be used for passive immunization or can be combined with subunit vaccine preparations to enhance the immune response. Polyclonal and monoclonal antibodies are also useful for diagnostic purposes.

One embodiment of the invention is a method of eliciting an immune response against the antigen, epitope, immunogen, peptide or polypeptide of interest in an animal, comprising administering a formulation for delivery and expression of a recombinant vaccine in an effective amount for eliciting an immune response. Still another embodiment of the invention is a method of inducing an immunological or protective response in an animal, comprising administering to the animal an effective amount of a formulation for delivery and expression of an antigen, epitope, immunogen, peptide or polypeptide of interest wherein the formulation comprises a recombinant vaccine and a pharmaceutically or veterinarily acceptable carrier, vehicle or excipient.

The invention relates to a method to elicit, induce or stimulate the immune response of an animal, advantageously a mammal or a vertebrate.

Another embodiment of the invention is a kit for performing a method of inducing an immunological or protective response against an antigen, epitope, immunogen, peptide or polypeptide of interest in an animal comprising a recombinant vaccine and instructions for performing the method of delivery in an effective amount for eliciting an immune response in the animal.

The invention will now be further described by way of the following non-limiting examples.

EXAMPLES

Example 1

ELISA study of *Streptococcus equi* Polypeptides

The IgG antibody responses directed towards *Streptococcus equi* cell surface proteins in sera taken from ponies intranasally challenged with 4 doses of *Streptococcus equi* strain 4047 were determined by ELISA. These *Streptococcus equi* proteins were obtained by in vitro expression in *Escherichia coli*. The antibody responses in sera from the six ponies receiving the higher doses of $3 \times 10^7$ and $3 \times 10^5$ cfu were averaged and compared to those from ponies challenged with 3000 and 30 cfu of *Streptococcus equi* 4047. Ponies receiving the higher doses developed strangles. Those receiving the low doses remained healthy throughout the study. On the basis of the results of this study, polypeptides of *Streptococcus equi* were selected for expression in *Escherichia coli* and for test of efficacy in mice and in ponies.

Example 2

Expression of Recombinant *Streptococcus equi* Polypeptides in *Escherichia coli*

Polynucleotides encoding fragments of Se50, Se1459 and Se358 were produced using Vent DNA polymerase (New England Biolabs® Inc.) as per the manufacturers recommended conditions with a 5 minute denaturation step followed by 35 cycles using 30 seconds annealing at 50-55° C., 1 minute extension at 72° C., and 30 second denaturing at 95° C. Products were finished off with a 4-minute 72° C. extension. The template in each case was *Streptococcus equi* strain 4047 chromosomal DNA. The fragments of Se50, Se1459 and Se358 are those designated as SEQ ID NOS: 32, 34 and 40, respectively.

Polynucleotides encoding fragments of Se528 and Se595 were produced using the pfu polymerase with same conditions as above apart from the extension time extended to two minutes at 72° C. The fragments of Se528 and Se595 are those designated as SEQ ID NOS: 38 and 36, respectively.

TABLE 1

Primers used to clone and sequence recombinant subunits.

| Primer name | Sequence | Function | SEQ ID NO: |
|---|---|---|---|
| 5'50GST | AAAGGATCCTACAGCCAGCAGCACTAAAA | Se50 cloning | 1 |
| 3'50GST | AAAGAATTCTTGGGCAGCTTCTTCTA | Se50 cloning | 2 |
| 5'1459GST | TTTGGATCCTATCGGAACCCAATCCATAT | Se1459 cloning | 3 |
| 3'1459GST | AAAGAATTCATTTTTAAGTTCAAACTC | Se1459 cloning | 4 |
| 5'595GST | AAAGGATCCTAGCTACCCTCATCACAGGA | Se595 cloning | 5 |
| 3'595GST | TTTGAATTCTTGTTTTTAGGTGTTGC | Se595 cloning | 6 |
| 5'528 LONG | TTTGGATCCTAGAGGTAGTTGAAGTTTGGCCTAATGGG | Se528 cloning | 7 |
| 3'528 LONG | AAAGAATTCTTTTTCTGTCTTGTTGAAGTAATCTGCCC | Se528 cloning | 8 |
| ASW49 | GACGGATCCCCTCTAATGGTGGAAACAAAGGAAGC | Se358 cloning | 9 |
| ASW50* | GACTGAATTCAAACAAAGCACAACACCAG | Se358 cloning | 10 |
| 5'pGEX | GGGCTGCAAGCCACGTTTGGTG | Sequencing | 11 |
| 3'pGEX | CCGGGAGCTGCATGTGTCAGAGG | Sequencing | 12 |
| 595 seq1 | AAAGAGCTAATCTGGCAG | Sequencing Se595 | 13 |
| 595 seq2 | CTCAATTGGAGGCTACAG | Sequencing Se595 | 14 |
| 595 seq3 | TGACGCTTCCAAAGCAAG | Sequencing Se595 | 15 |
| 595 seq4 | CTCCGGAAACACCAAAGG | Sequencing Se595 | 16 |

*The recombinant Se358 ends at the actual stop codon for Se358 as the ASW50 primer site is located down stream from the gene.

All PCR products were purified using the Qiaquick PCR purification kit (Qiagen) with a 32 µl elution volume, then digested with the addition of EcoRI buffer (3.5 µl) (New England Biolabs® Inc.), BamHI (0.75 µl) and EcoRI (0.75 µl) for 2 hours at 37° C. 1 g of pGEX-3X plasmid (GE Healthcare) was also digested with EcoRI and BamHI as described above. The pGEX-3X plasmids have a multiple cloning site, a tac promoter, glutathione S-transferase gene (GST) and stop codons in all three frames, for the production of GST fusion proteins and their isolation and purification.

All digestion products were run on 0.7% TAE agarose gels, the desired restriction product excised and purified using the Qiaquick gel extraction kit (Qiagen) with a 35 µl final elution.

Ligation reactions were set up using 16.5 µl of purified digested PCR product and 1 µl of pGEX-3X plasmid with 2 µl of ligase buffer and 0.5 µl of ligase, and incubated overnight at room temperature (rtp).

The ligation reactions were transformed into E. coli DH 10B strain and plated onto L-agar plates supplemented with 50 µg/ml ampicillin and incubated overnight at 37° C. Transformants were tested for the presence of insert by colony PCR. A single colony was resuspended in 4 µl of water and 2 µl of this was added to a Taq DNA polymerase PCR reaction containing the appropriate cloning primers for the polynucleotide of interest and a 35 cycle extension was performed as described above (1 minute for Se50, Se1459 and Se358 and 2 minutes for Se595 and Se528). The presence of the desired insert was confirmed by running the PCR reaction on 0.7% TAE agarose gels.

Plasmids of each of the clones were prepared and sequenced using the 5' and 3' pGEX-3X PCR primers for all of the clones (Table 1). Due to its size, Se595 was also sequenced using the additional primers listed above (Table 1). All of the cloned polynucleotides were confirmed to have the same sequence as the assembled Streptococcus equi strain 4047 genome sequence (http://www.sanger.ac.uk/Projects/S_equi/).

Clones of Se1459, Se595, Se528, Se50 and Se358 were induced for expression using the following protocol. A single colony was inoculated into 50 ml 2×YT culture medium containing 50 µg/ml ampicillin and was grown overnight with shaking at 220 rpm at 37° C. This culture was then added to 500 ml of pre-warmed (37° C.) and pre-gassed 2×YT and incubated for 1 hour at 37° C.

For all cultures, after 1 hour, 200 µl was removed and the cells were collected for analysis (this being the pre-induction sample), IPTG (isopropyl-beta-D-thiogalactopyranoside) was added to a final concentration of 0.1 mM, and the temperature was lowered to 28° C. The culture was induced for a further four hours and a 100 µl sample was removed for analysis, after which the cells were harvested by centrifugation and stored at −70° C.

All samples were analysed using 10% SDS-PAGE.

For Se1459, Se595, Se528, Se50 and Se358, the pellets were resuspended in 20 ml of ice cold PBS (Oxoid Limited, catalog #BR0014G), PMSF (Phenylmethyl sulphonyl fluoride) was added to a final concentration of 0.1 mM and the cells were lysed by sonication on ice with 6×10 second pulses with a 10 second rest between each pulse. Triton X-100 was added to 0.1% (v/v) and the insoluble and intact cells were removed by centrifugation (11,000 g, 5 min 4° C.). Samples of the soluble bacterial lysate and insoluble material were analysed by SDS-PAGE. DTT (dithiothreitol; Cleland's reagent) (5 mM) was added and 1.3 ml of glutathione sepharose 4B was added (equates to 1 ml of beads, these were pre-washed three times with 20 ml PBS). The mixture was incubated at room temperature for 1 hour and then the beads were collected by centrifugation (800 g, 2 min, rtp) and washed three times with 50 ml of ice cold PBST (PBS with 0.1% v/v Triton X-100). Samples of each wash (washes 1-3) were taken for analysis by SDS-PAGE as was a sample of the fusion protein attached to the beads. All samples were analysed using 10% SDS-PAGE.

Removal of the GST carrier was done for all fusion proteins by protease cleavage.

For Se1459, Se595, Se528, Se50 and Se358, cleavage reactions were performed with the fusion protein attached to the glutathione sepharose beads. The beads were first equilibrated once with 20 ml of wash buffer (Tris-HCL, 50 mM, pH 7.5, NaCl, 150 mM) and then twice with 20 ml cleavage buffer (wash buffer with $CaCl_2$, 1.0 mM) and finally resuspended in 1 ml of cleavage buffer. Factor Xa (New England Biolabs® Inc.) (50 units) was added and incubated on a rotary mixer for 16 hours at room temperature. The released protein was recovered by pelleting the glutathione beads (800 g, 2 min, rtp) and retaining the supernatant. The beads were washed twice with 1 ml of wash buffer and the supernatant was retained each time. Aliquots of each supernatant and the remaining glutathione beads were analysed by SDS-PAGE. The beads were washed three times with wash buffer 2 (Tris-HCL, 50 mM, pH8.0) and eluted with 3 ml of wash buffer 2 containing 5.0 mM reduced glutathione for 2 min at room temperature followed by pelleting the beads (800 g, 2 min, rtp) and retaining the supernatant. This elution was repeated twice and the purity of each fraction was analysed by SDS-PAGE.

All the proteins were dialysed twice in 5 liters of 20 mM sodium phosphate buffer pH7.4 at 4° C. overnight.

After dialysis, any insoluble material was removed by centrifugation (10000 g, 2 min, 4° C.), and then it was stored at −70° C.

Example 3

Protection in Mice after Subunit Vaccine Administration and *Streptococcus equi* Challenge The objective of this study was to determine if vaccination with *Streptococcus equi* subunit vaccine protected mice from subsequent intranasal *Streptococcus equi* challenge.

Five *Streptococcus equi* subunit vaccines were used, Se595, Se358, Se1459, Se50 and Se528. All these vaccines used the *Streptococcus equi* proteins obtained in Example 2. The Se595, Se358, Se1459, Se50 and Se528 recombinant *Streptococcus equi* proteins were purified by buffer exchanged into 20 mM Sodium Phosphate pH7.4 and concentrated to give a concentration equivalent to the molar concentration of Se358 at 10 µg/ml where possible. Proteins, Se595 and Se528 were insoluble at the desired concentration. The actual protein concentrations used are shown in Table 2.

TABLE 2

Actual doses of recombinant subunits administered

| Protein | Dose administered | Dose equivalent to Se358 |
| --- | --- | --- |
| Se595 | 11.2 µg | 5.3 µg |
| Se358 | 10 µg | 10 µg |
| Se1459 | 1.7 µg | 10 µg |
| Se50 | 1.9 µg | 9.6 µg |
| Se528 | 4.2 µg | 3.4 µg |

Purified proteins in 20 mM Sodium Phosphate pH 7.4, were diluted 1:3 in TS6 adjuvant (example 1 of US-A-2005/0079185) prior to administration.

Groups of 20 3-4 week old female BalbC mice were vaccinated on day 0 (D0) with each of five *Streptococcus equi* subunit vaccines. Vaccinations were given by intramuscular injection in the thigh and intranasally. These mice were given a booster vaccination after 4 weeks (D28) and challenged with *Streptococcus equi* after a further 2 weeks (D42). An additional control group receiving no vaccination was also included, and was challenged on D42. A group of 5 control mice was not vaccinated or challenged with *Streptococcus equi* (see Table 3).

The group size is sufficient to detect 50% protection of vaccinated mice with 80% infection of controls. Blood was taken before vaccination, before boost, before challenge and on euthanasia to determine the level of antibody response to vaccination and challenge.

*Streptococcus equi* strain 4047 was grown for challenge in Todd Hewitt broth (THB) supplemented with 10% foetal calf serum (FCS). An overnight culture was diluted 1:20 to inoculate fresh pre-warmed and gassed THB+10% FCS and the culture grown until an $OD_{600\ nm}$ of 0.3 was reached. At this point, dilutions of the culture were made. Following preparation of the required dose of *Streptococcus equi* strain 4047, mice were sedated with 100 mg/kg of Ketaset by intramuscular injection and challenged by intranasal administration of 10 µl of challenge inocula containing approximately $1 \times 10^4$ cfu *S. equi*.

Immediately after challenge, the dose administered was quantified by back titration and was found to contain $0.9 \times 10^4$ cfu.

All the mice were carefully monitored to ensure complete recovery from sedation and checked regularly for the onset of clinical signs of disease. These included malaise, shivering or staring coat and were taken as a sign of moderate effect with the onset of more severe effects possible. Mice were finally euthanased.

Clinical observations were recorded daily throughout the study and mice were weighed pre vaccination, pre boost, pre challenge and then daily post challenge. Nasal dabs were taken from mice post challenge to quantify the level of *Streptococcus equi* shedding. A post mortem examination was carried out on all mice.

TABLE 3

Summary of study protocol

| # of mice | Age of mice | Vaccine Subunit | Dose | Booster | Challenge dose (cfu) | Route |
|---|---|---|---|---|---|---|
| 20 | 3-4 weeks | Se595 + adjuvant | 20 µl IN + IM | Yes | 1 × 10$^4$ | 10 µl IN |
| 20 | 3-4 weeks | Se358 + adjuvant | 20 µl IN + IM | Yes | 1 × 10$^4$ | 10 µl IN |
| 20 | 3-4 weeks | Se1459 + Adjuvant | 20 µl IN + IM | Yes | 1 × 10$^4$ | 10 µl IN |
| 20 | 3-4 weeks | Se50 + adjuvant | 20 µl IN + IM | Yes | 1 × 10$^4$ | 10 µl IN |
| 20 | 3-4 weeks | Se528 + adjuvant | 20 µl IN + IM | Yes | 1 × 10$^4$ | 10 µl IN |
| 60 | 3-4 weeks | No vaccine | No vaccine | No | 1 × 10$^4$ | 10 µl IN |
| 5 | 3-4 weeks | None | None | No | none | 10 µl IN |

The vaccination phase proceeded without incident, all groups gained weight in line with controls. No adverse injection site reactions were identified. All mice seroconverted with respect to the vaccination administered.

Following challenge, Groups vaccinated with Se595, Se358, Se1459, Se528 and Se50 generally had reduced clinical signs of disease, reduced weight loss, more weight gain, reduced nasal colonisation and improved survival when compared with controls. Each mouse was examined on the day of challenge and on each of the following 7 days for the occurrence of symptoms associated with *Streptococcus equi* (lethargy, weight loss, sneezing, piloerection, hunched up, inner ear imbalance). Mice were examined at least 4 times a day. The following recording and scoring method was applied (Table 4)

TABLE 4

Strangles scoring method

| Observation | Score |
|---|---|
| Normal | 0 |
| Slight piloerection | 1 |
| Piloerection | 3 |
| Quiet | 3 |
| Marked sneezing | 3 |
| Hunched | 5 |
| Rapid breathing | 5 |
| Ear imbalance | 5 |
| Immobile | 10 |

For example: A mouse with piloerection that is quiet, hunched and immobile would score 3+3+5+10=21.

Weights of mice were analysed on a spreadsheet each day to determine % weight loss relative to the day of challenge.

Following challenge, the nose of each mouse was touched onto a clearly labelled Streptococcal selective agar plate each day (bioMerieux). Plates were streaked to determine if viable *S. equi* bacteria were present. The level of *S. equi* shedding was graded according to the following 4 point scoring system; 0=no growth, 1=1-10 colonies present, 2=11-100 colonies present, 3=greater than 100 colonies and 4=confluent growth.

Blood samples were taken from the thigh vein. Serum was prepared and stored frozen at −20° C. or below until use.

Figure 2:
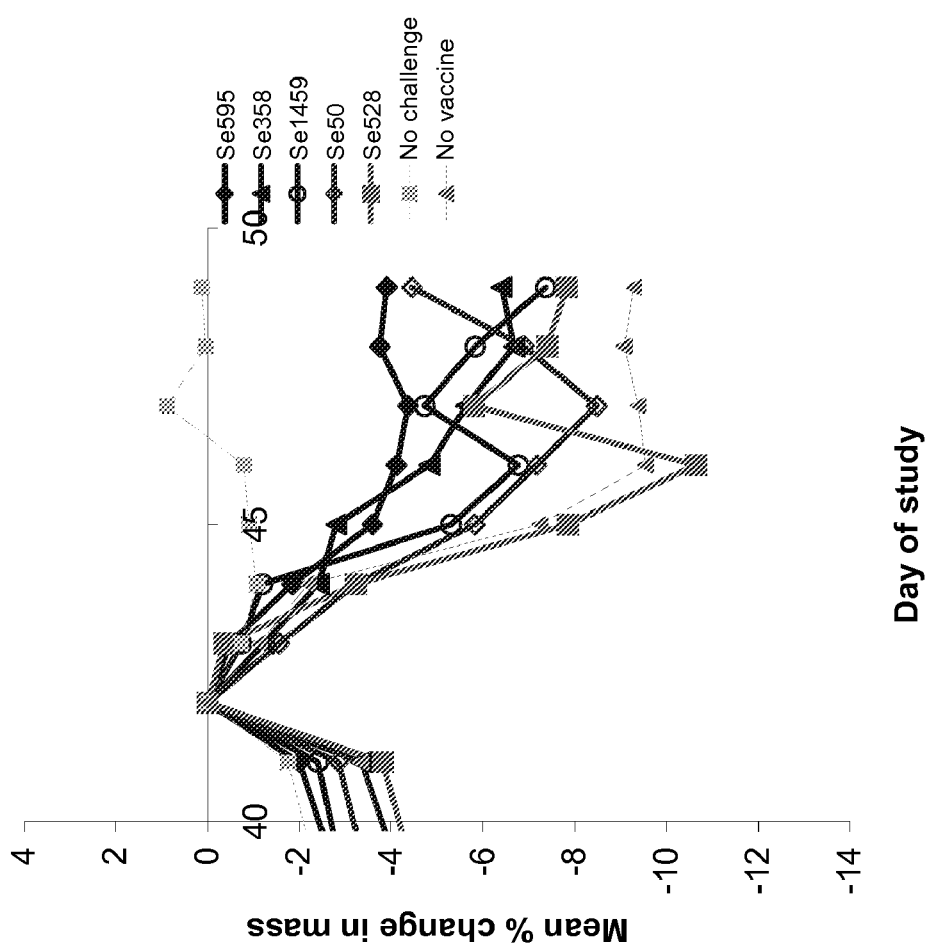
FIG. 2 shows the mean percentage of change in mass of vaccinated and control mice after *Streptococcus equi* challenge.

Clinical signs of disease were observed from D44, 2 days post challenge. The vaccinated groups generally had lower clinical signs than the control groups. Mice vaccinated with Se50 and Se358 had the lowest level of clinical signs of disease. Those vaccinated with Se595 had clinical signs of disease for a reduced period compared with controls (FIG. 1). On examining the mean percentage change in mass following challenge, relative to the day of challenge (D42), it was apparent that Groups vaccinated with Se528, Se1459 and Se50 had a slightly reduced weight loss. However, Se358 and Se595 vaccinated mice appeared best protected (FIG. 2).

Figure 3:
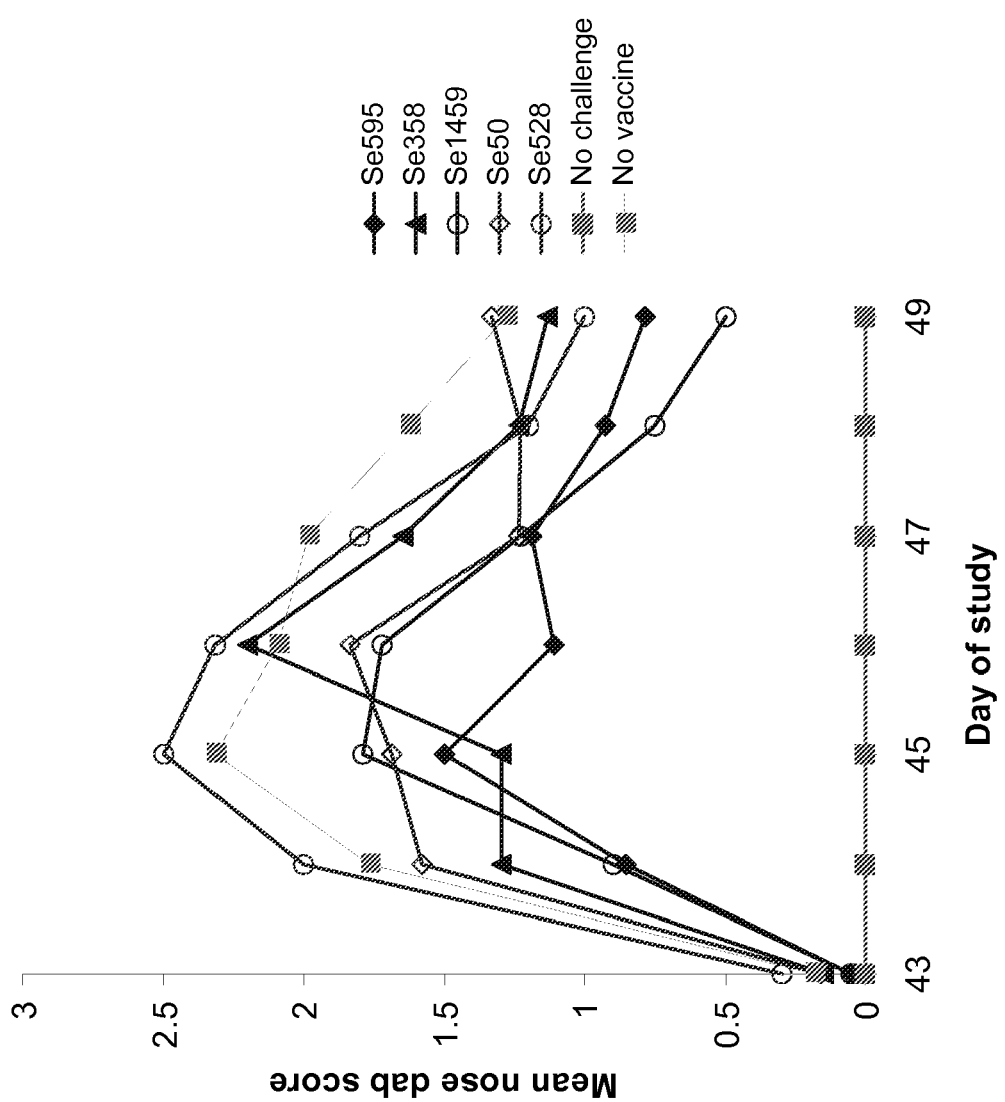
FIG. 3 shows the mean nose dabs score of vaccinated and control mice after *Streptococcus equi* challenge.

As expected, the mean number of β-hemolytic bacteria isolated from nasal dabs increased following challenge, peaking at D45 (3 days post challenge). On D45, the lowest nasal dabs scores were seen in groups vaccinated with Se358, Se595, Se50 and Se1459. The vaccinated groups generally had lower scores than the control groups. The exception being Se358 vaccinated mice, which peaked on D46 (FIG. 3).

TABLE 5

IgG Serological responses

| | Sera dilution in ELISA | Seroconversion |
|---|---|---|
| Se595 | 1:80000* | All mice seroconverted |
| Se358 | 1:160000* | All mice seroconverted |
| Se1459 | 1:100** | All mice seroconverted |
| Se50 | 1:160000* | All mice seroconverted |
| Se528 | 1:3000* | All mice seroconverted |

*Sera dilution to achieve an ELISA reading of around 1.5 in preliminary studies.
**Sera dilution to achieve an ELISA reading of around 0.3 in preliminary studies.

Example 4

Expression of Recombinant *Streptococcus equi* Se1631, Se1681 and Sla Polypeptides in *Escherichia coli*

Polynucleotides encoding fragments of Se1631, Se1681 and Sla were produced using Vent DNA polymerase (New England Biolabs® Inc.) as per the manufacturers recommended conditions with a 5 minute denaturation step followed by 35 cycles using 30 seconds annealing at 50-55° C., 1 minute extension at 72° C., and 30 second denaturing at 95° C. Products were finished off with a 4-minute 72° C. extension. The template in each case was *Streptococcus equi* strain 4047 chromosomal DNA.

The fragments of Se1631, Se1681 and Sla are those designated as SEQ ID NOS: 53, 55 and 57, respectively.

TABLE 6

Primers used to clone and sequence recombinant subunits.

| Primer name | Sequence | Function | SEQ ID NO: |
|---|---|---|---|
| 5'1631GST | AAAGGATCCTGCAGTCTACAAATGACAATAC | Se1631 cloning | 41 |
| 3'1631GST | AAAGAATTCTTATTTTTCTGACTTAGATTTAGAAG | Se1631 cloning | 42 |
| 5'1681GST | AAAGGATCCTGGCGACTACCCTAGCAGGACAAAC | Se1681 cloning | 43 |
| 3'1681GST | AAAGAATTCTTATGTATCTTGACAGTGCTTAAG | Se1681 cloning | 44 |
| 5'SLAGST | CCCGGATCCTAGAAGGGATAAATGATAAAATAG | Sla cloning | 45 |
| 3'SLAGST | TTTGAATTCTTACAAAACATCTACTACTGGCAAC | Sla cloning | 46 |

All PCR products were purified using the Qiaquick PCR purification kit (Qiagen) with a 32 µl elution volume, then digested with the addition of EcoRI buffer (3.5 µl) (New England Biolabs® Inc.), BamHI (0.75 µl) and EcoRI (0.75 µl) for 2 hours at 37° C. 1 g of pGEX-3X plasmid (GE Healthcare) was also digested with EcoRI and BamHI as described above. The pGEX-3X plasmids have a multiple cloning site, a tac promoter, glutathione S-transferase gene (GST) and stop codons in all three frames, for the production of GST fusion proteins and their isolation and purification.

All digestion products were run on 0.7% TAE agarose gels, the desired restriction product excised and purified using the Qiaquick gel extraction kit (Qiagen) with a 35 µl final elution.

Ligation reactions were set up using 16.5 µl of purified digested PCR product and 1 µl of pGEX-3X plasmid with 2 µl of ligase buffer and 0.5 µl of ligase, and incubated overnight at room temperature (rtp).

The ligation reactions were transformed into *E. coli* DH10B strain and plated onto L-agar plates supplemented with 50 µg/ml ampicillin and incubated overnight at 37° C. Transformants were tested for the presence of insert by colony PCR. A single colony was resuspended in 4 µl of water and 2 µl of this was added to a Taq DNA polymerase PCR reaction containing the appropriate cloning primers for the polynucleotide of interest and a 35 cycle extension was performed as described above. The presence of the desired insert was confirmed by running the PCR reaction on 0.7% TAE agarose gels.

Plasmids of each of the clones were prepared and sequenced using the 5' and 3' pGEX-3X PCR primers for all of the clones (Table 6). All of the cloned polynucleotides were confirmed to have the same sequence as the assembled *Streptococcus equi* strain 4047 genome sequence (http://www.sanger.ac.uk/Projects/S_equi/).

All clones were induced for expression using the following protocol. A single colony was inoculated into 50 ml 2×YT culture medium containing 50 µg/ml ampicillin and was grown overnight with shaking at 220 rpm at 37° C. This culture was then added to 500 ml of pre-warmed (37° C.) and pre-gassed 2×YT and incubated for 1 hour at 37° C. After 1 hour, 200 µl was removed and the cells were collected for analysis (this being the pre-induction sample), IPTG (isopropyl-beta-D-thiogalactopyranoside) was added to a final concentration of 0.1 mM, and the temperature was lowered to 28° C. The culture was induced for a further four hours and a 100 µl sample was removed for analysis, after which the cells were harvested by centrifugation and stored at −70° C.

All samples were analysed using 10% SDS-PAGE.

The pellets were resuspended in 20 ml of ice cold PBS (Oxoid Limited, catalog #BR0014G), PMSF (Phenylmethyl sulphonyl fluoride) was added to a final concentration of 0.1 mM and the cells were lysed by sonication on ice with 6×10 second pulses with a 10 second rest between each pulse. Triton X-100 was added to 0.1% (v/v) and the insoluble and intact cells were removed by centrifugation (11,000 g, 5 min 4° C.). Samples of the soluble bacterial lysate and insoluble material were analysed by SDS-PAGE. DTT (dithiothreitol; Cleland's reagent) (5 mM) was added and 1.3 ml of glutathione sepharose 4B was added (equates to 1 ml of beads, these were pre-washed three times with 20 ml PBS). The mixture was incubated at room temperature for 1 hour and then the beads were collected by centrifugation (800 g, 2 min, rtp) and washed three times with 50 ml of ice cold PBST (PBS with 0.1% v/v Triton X-100). Samples of each wash (washes 1-3) were taken for analysis by SDS-PAGE as was a sample of the fusion protein attached to the beads. All samples were analysed using 10% SDS-PAGE.

Removal of the GST carrier was done for all fusion proteins by protease cleavage.

Cleavage reactions were performed with the fusion protein attached to the glutathione sepharose beads. The beads were first equilibriated once with 20 ml of wash buffer (Tris-HCL, 50 mM, pH 7.5, NaCl, 150 mM) and then twice with 20 ml cleavage buffer (wash buffer with CaCl$_2$, 1.0 mM) and finally resuspended in 1 ml of cleavage buffer. Factor Xa (New England Biolabs® Inc.) (50 units) was added and incubated on a rotary mixer for 16 hours at room temperature. The released protein was recovered by pelleting the glutathione beads (800 g, 2 min, rtp) and retaining the supernatant. The beads were washed twice with 1 ml of wash buffer and the supernatant was retained each time. Aliquots of each supernatant and the remaining glutathione beads were analysed by SDS-PAGE. The beads were washed three times with wash buffer 2 (Tris-HCL, 50 mM, pH8.0) and eluted with 3 ml of wash buffer 2 containing 5.0 mM reduced glutathione for 2 min at room temperature followed by pelleting the beads (800 g, 2 min, rtp) and retaining the supernatant. This elution was repeated twice and the purity of each fraction was analysed by SDS-PAGE.

The beads were washed three times with wash buffer 2 (Tris-HCL, 50 mM, pH8.0) and eluted with 3 ml of wash buffer 2 containing 5.0 mM reduced glutathione for 2 min at room temperature followed by pelleting the beads (800 g, 2 min, rtp) and retaining the supernatant. This elution was repeated twice and the purity of each fraction was analysed by SDS-PAGE.

All the proteins were dialysed twice in 5 liters of 20 mM sodium phosphate buffer pH7.4 at 4° C. overnight.

After dialysis, any insoluble material was removed by centrifugation (10000 g, 2 min, 4° C.), and then it was stored at −70° C.

Example 5

Protection in Mice after Se1631, Se1681 or Sla Subunit Vaccine Administration and *Streptococcus equi* Challenge Groups of 20 3/4 week old female BalbC mice were vaccinated with each of Se1631, Se1681 and Sla *S. equi* peptides, and a GST+adjuvant control group. This group size is sufficient to detect 50% protection of mice with 80% infection of controls. An additional control group of 5 mice receiving no vaccination or challenge was included (see Table 7).

Three *Streptococcus equi* subunit vaccines were used, Se1631, Se1681358 and Sla. All these vaccines used the *Streptococcus equi* proteins obtained in Example 4.

Recombinant proteins were prepared for vaccination by centricon concentration in 0.02M phosphate buffer pH 7.4 to 1.5 mg/ml and adding 2 parts of TS6 adjuvant (example 1 of US-A-2005/0079185).

Mice were vaccinated on Day 0 and boosted on Day 28. IM vaccinations were administered into the left hind leg on Day 0 and the right hind leg on Day 28 according to the following table. IN vaccinations will be administered via a pipette onto the nares of mice.

Blood was taken before vaccination, before boost and before challenge to determine the level of antibody response to vaccination.

Mice were challenged with *S. equi* after a further 2 weeks. *S. equi* strain 4047 were prepared as described in example 3. Following dilution to the required dose, 10 μl were administered to sedated mice by the intranasal route in a contained environment. Mice were carefully monitored to ensure complete recovery from sedation and checked regularly for the onset of clinical signs of disease. These include malaise, shivering or staring coat and were taken as a sign of moderate effect with the onset of more severe effects possible.

TABLE 7

Summary of study protocol

| # of mice | Age of mice | Vaccine Subunit | Dose | Booster | Challenge dose (cfu) | Route |
|---|---|---|---|---|---|---|
| 20 | 3-4 weeks | Se1631 + adjuvant | 20 μl IN + IM | Yes | 1 × 10$^4$ | 10 μl IN |
| 20 | 3-4 weeks | Se1681 + adjuvant | 20 μl IN + IM | Yes | 1 × 10$^4$ | 10 μl IN |
| 20 | 3-4 weeks | Sla + adjuvant | 20 μl IN + IM | Yes | 1 × 10$^4$ | 10 μl IN |
| 20 | 3-4 weeks | GST + adjuvant | 20 μl IN + IM | Yes | 1 × 10$^4$ | 10 μl IN |
| 5 | 3-4 weeks | None | None | No | none | 10 μl IN |

Clinical observations were recorded daily throughout the study (for the scoring method see Table 4) and mice were weighed pre vaccination, pre boost, pre challenge and then daily post challenge. Nasal dabs were taken from mice post challenge to quantify the level of *S. equi* shedding.

Figure 4:
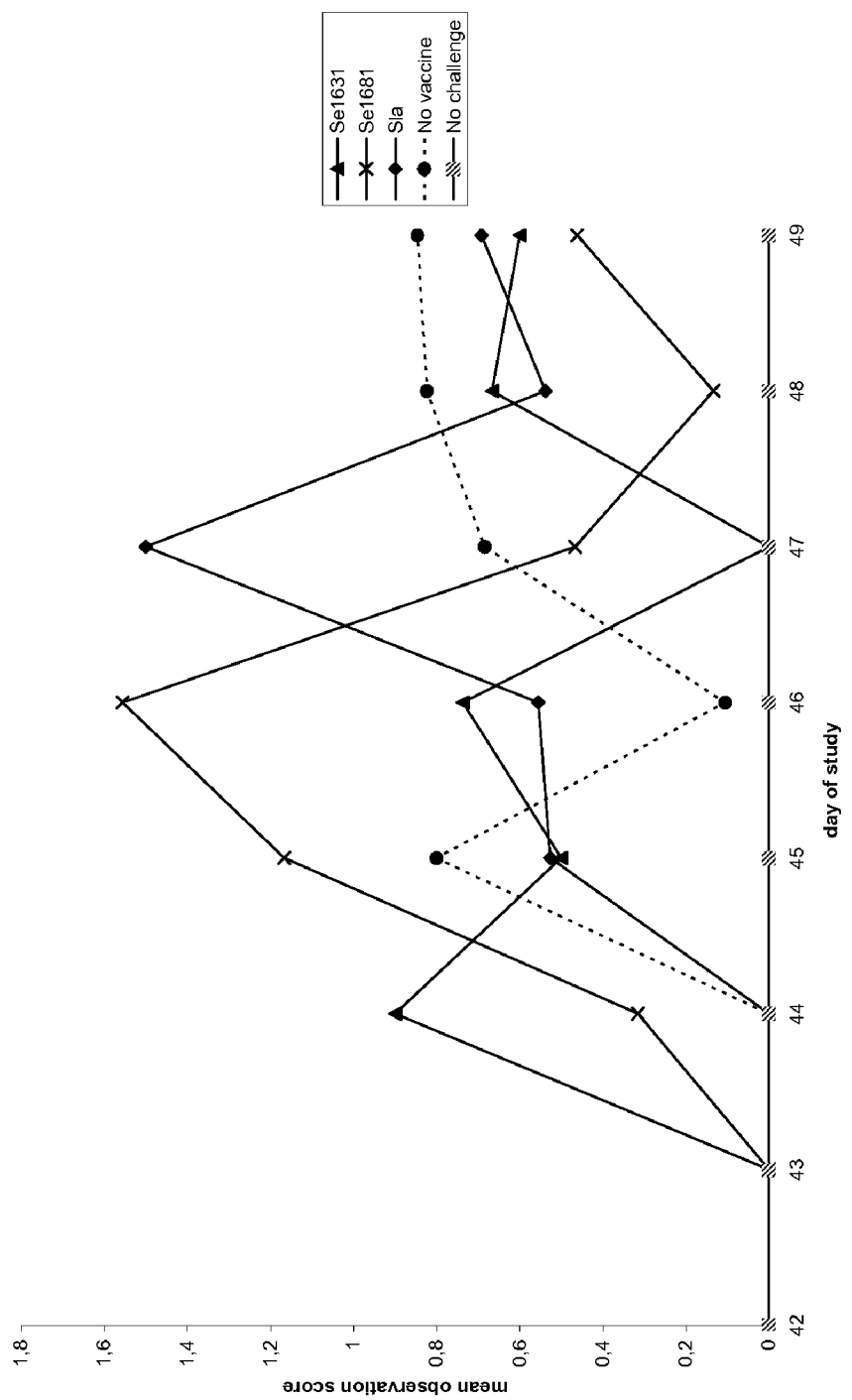
FIG. 4 shows the mean clinical scores of Se1631, Se1681, Sla vaccinated and control mice following challenge with *Streptococcus equi*.

Clinical signs of disease were observed from D44, 2 days post challenge. The vaccinated groups generally had lower clinical signs than the control groups. Mice vaccinated with Se1631 had the lowest level of clinical signs of disease. Those vaccinated with Se1681 and Sla had clinical signs of disease for a reduced period compared with controls (FIG. 4).

Figure 5:
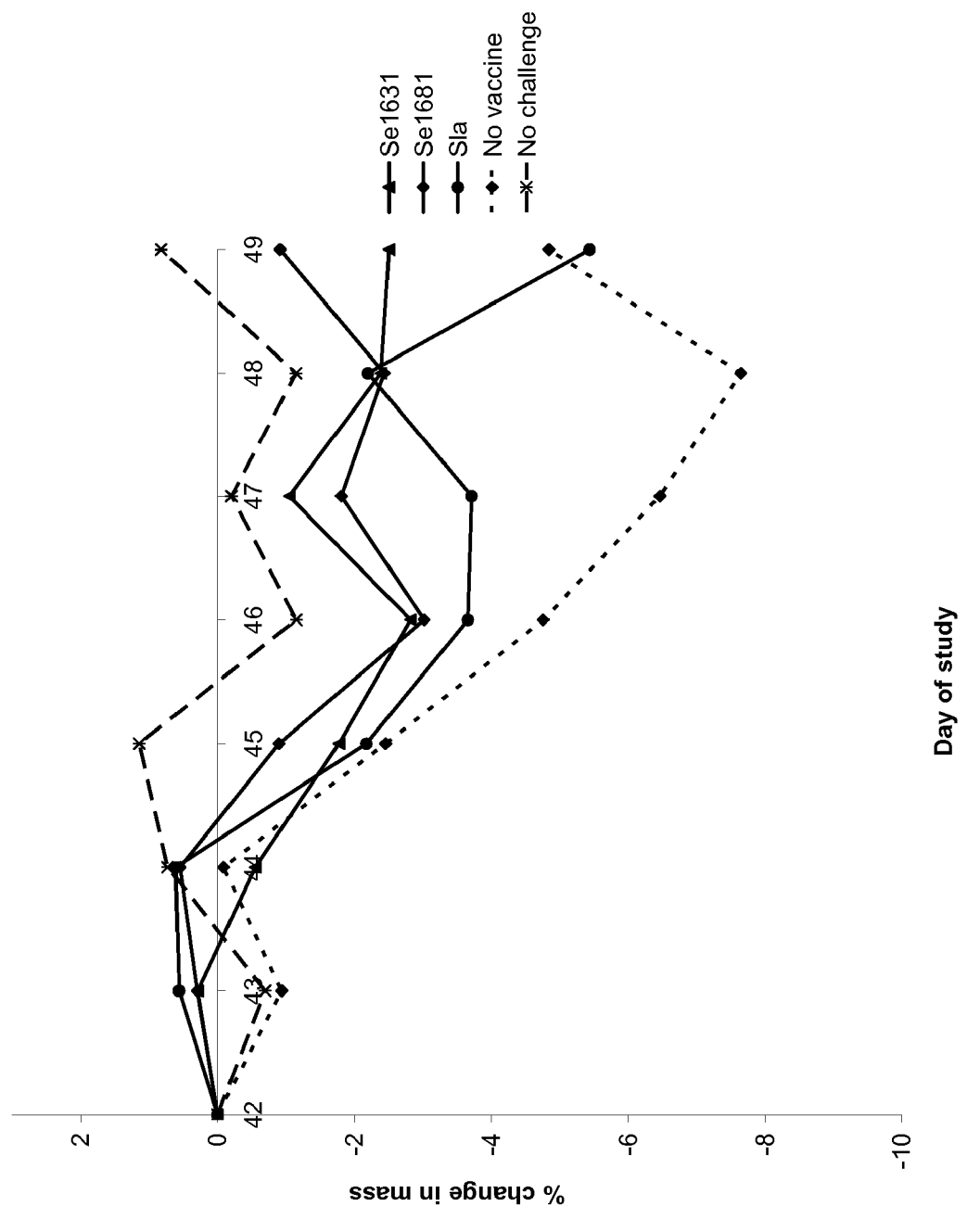
FIG. 5 shows the mean percentage of change in mass of Se1631, Se1681, Sla vaccinated and control mice after *Streptococcus equi* challenge.

On examining the mean percentage change in mass following challenge, relative to the day of challenge (D42), it was apparent that Groups vaccinated with Se1681, Se1631 and Sla had a slightly reduced weight loss. On day D49, Sla vaccinated mice appeared less protected (FIG. 5).

Figure 6:
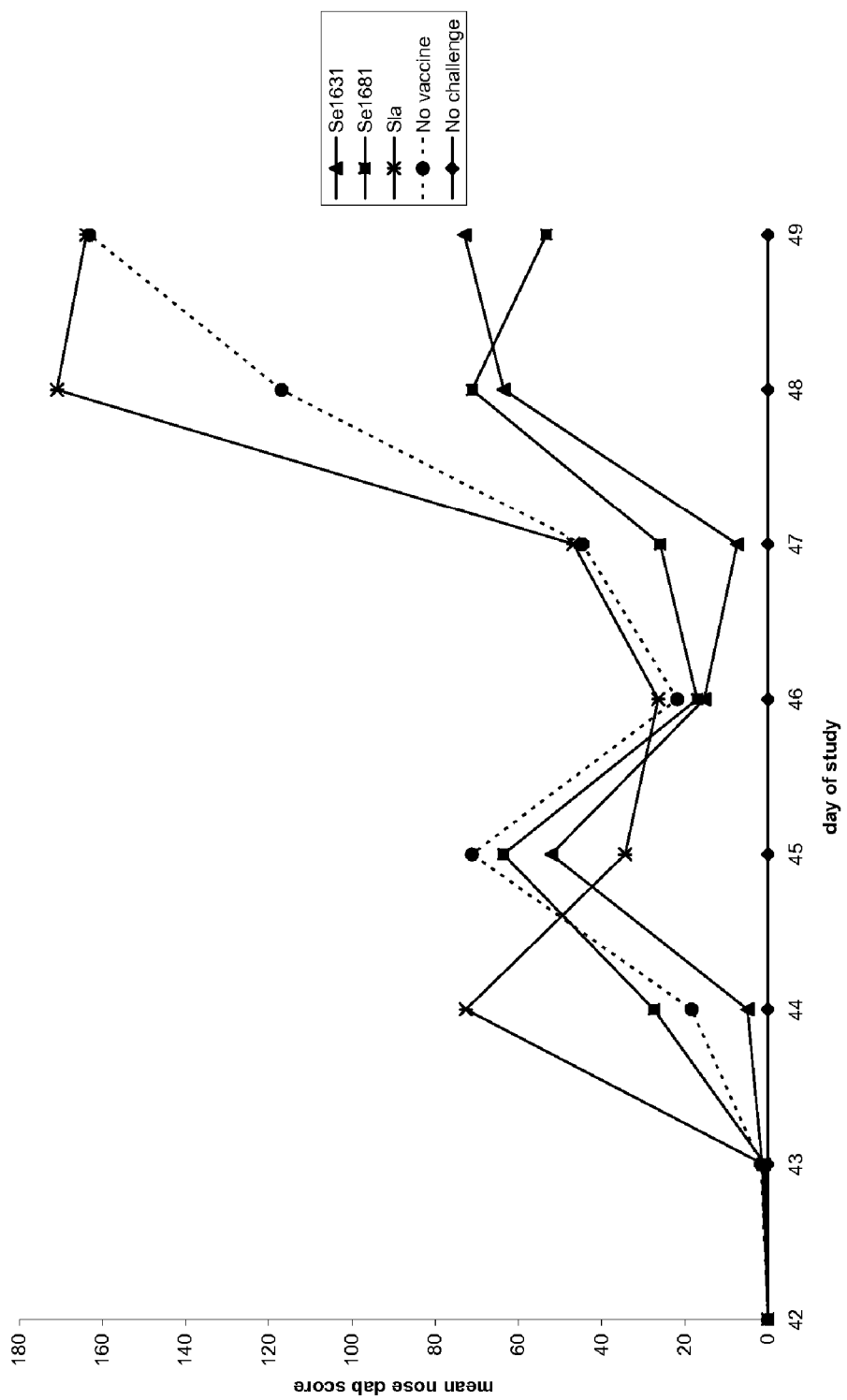
FIG. 6 shows the mean nose dabs score of Se1631, Se1681, Sla vaccinated and control mice after *Streptococcus equi* challenge (expressed in colony forming unit (cfu))
Figure 7:
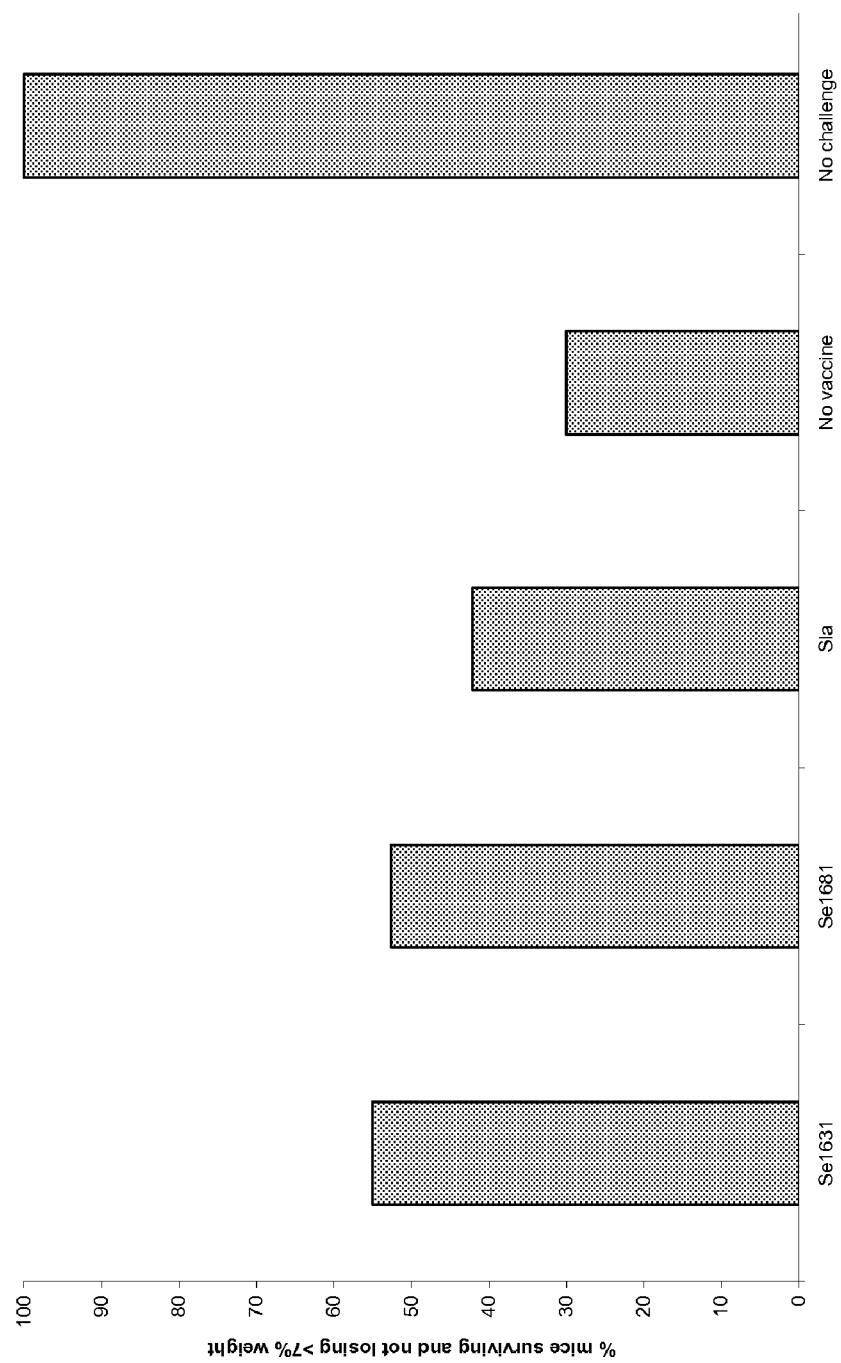
FIG. 7 shows the percentage of mice surviving and not losing more than 7% weight of Se1631, Se1681, Sla vaccinated and control mice after *Streptococcus equi* challenge.

As expected, the mean number of β-hemolytic bacteria isolated from nasal dabs increased following challenge, peaking for the control group at D49 (7 days post challenge). On D49, the lowest nasal dabs scores were seen in groups vaccinated with Se1631 and Se1681. The vaccinated groups generally had lower scores than the control groups. The exception being Sla vaccinated mice, which peaked on D48 (FIG. 6). On examining percentage of mice surviving and not losing more than 7% weight (FIG. 7), it was apparent that Groups vaccinated with Se1631, Se1681 and Sla had a reduced weight loss and a better surviving rate than the control groups.

Having thus described in detail preferred embodiments of the present invention, it is to be understood that the invention defined by the above paragraphs is not to be limited to particular details set forth in the above description as many apparent variations thereof are possible without departing from the spirit or scope of the present invention.

What is claimed is:

1. An immunogenic composition comprising at least one polypeptide comprising the amino acid sequence of SEQ ID NO: 22.

2. An immunogenic composition comprising at least one polypeptide comprising the amino acid sequence of SEQ ID NO: 36.

3. The immunogenic composition of claim 1, wherein the immunogenic composition reduces the severity of strangles in an equine caused by *Streptococcus equi* infection.

4. A diagnostic kit for detecting infection by *Streptococcus equi* comprising at least one polypeptide of claim 1.

* * * * *

SEQUENCE LISTING

<160> NUMBER OF SEQ ID NOS: 58

<210> SEQ ID NO 1
<211> LENGTH: 29
<212> TYPE: DNA
<213> ORGANISM: Artificial
<220> FEATURE:

-continued

<223> OTHER INFORMATION: Oligonucleotides as PCR primer

<400> SEQUENCE: 1
aaaggatcct acagccagca gcactaaaa                                  29

<210> SEQ ID NO 2
<211> LENGTH: 26
<212> TYPE: DNA
<213> ORGANISM: Artificial
<220> FEATURE:
<223> OTHER INFORMATION: Oligonucleotides as PCR primer

<400> SEQUENCE: 2
aaagaattct tgggcagctt cttcta                                    26

<210> SEQ ID NO 3
<211> LENGTH: 29
<212> TYPE: DNA
<213> ORGANISM: Artificial
<220> FEATURE:
<223> OTHER INFORMATION: Oligonucleotides as PCR primer

<400> SEQUENCE: 3
tttggatcct atcggaaccc aatccatat                                 29

<210> SEQ ID NO 4
<211> LENGTH: 27
<212> TYPE: DNA
<213> ORGANISM: Artificial
<220> FEATURE:
<223> OTHER INFORMATION: Oligonucleotides as PCR primer

<400> SEQUENCE: 4
aaagaattca ttttaagtt caaactc                                    27

<210> SEQ ID NO 5
<211> LENGTH: 29
<212> TYPE: DNA
<213> ORGANISM: Artificial
<220> FEATURE:
<223> OTHER INFORMATION: Oligonucleotides as PCR primer

<400> SEQUENCE: 5
aaaggatcct agctaccctc atcacagga                                 29

<210> SEQ ID NO 6
<211> LENGTH: 27
<212> TYPE: DNA
<213> ORGANISM: Artificial
<220> FEATURE:
<223> OTHER INFORMATION: Oligonucleotides as PCR primer

<400> SEQUENCE: 6
tttgaattct tgttttttag gtgttgc                                   27

<210> SEQ ID NO 7
<211> LENGTH: 38
<212> TYPE: DNA
<213> ORGANISM: Artificial
<220> FEATURE:
<223> OTHER INFORMATION: Oligonucleotides as PCR primer

<400> SEQUENCE: 7
tttggatcct agaggtagtt gaagtttggc ctaatggg                       38

```
<210> SEQ ID NO 8
<211> LENGTH: 38
<212> TYPE: DNA
<213> ORGANISM: Artificial
<220> FEATURE:
<223> OTHER INFORMATION: Oligonucleotides as PCR primer

<400> SEQUENCE: 8
aaagaattct ttttctgtct tgttgaagta atctgccc                              38

<210> SEQ ID NO 9
<211> LENGTH: 35
<212> TYPE: DNA
<213> ORGANISM: Artificial
<220> FEATURE:
<223> OTHER INFORMATION: Oligonucleotides as PCR primer

<400> SEQUENCE: 9
gacggatccc ctctaatggt ggaaacaaag gaagc                                 35

<210> SEQ ID NO 10
<211> LENGTH: 29
<212> TYPE: DNA
<213> ORGANISM: Artificial
<220> FEATURE:
<223> OTHER INFORMATION: Oligonucleotides as PCR primer

<400> SEQUENCE: 10
gactgaattc aaacaaagca caacaccag                                        29

<210> SEQ ID NO 11
<211> LENGTH: 22
<212> TYPE: DNA
<213> ORGANISM: Artificial
<220> FEATURE:
<223> OTHER INFORMATION: Oligonucleotides as PCR primer

<400> SEQUENCE: 11
gggctgcaag ccacgtttgg tg                                               22

<210> SEQ ID NO 12
<211> LENGTH: 23
<212> TYPE: DNA
<213> ORGANISM: Artificial
<220> FEATURE:
<223> OTHER INFORMATION: Oligonucleotides as PCR primer

<400> SEQUENCE: 12
ccgggagctg catgtgtcag agg                                              23

<210> SEQ ID NO 13
<211> LENGTH: 18
<212> TYPE: DNA
<213> ORGANISM: Artificial
<220> FEATURE:
<223> OTHER INFORMATION: Oligonucleotides as PCR primer

<400> SEQUENCE: 13
aaagagctaa tctggcag                                                    18

<210> SEQ ID NO 14
<211> LENGTH: 18
<212> TYPE: DNA
<213> ORGANISM: Artificial
<220> FEATURE:
<223> OTHER INFORMATION: Oligonucleotides as PCR primer
```

```
<400> SEQUENCE: 14
ctcaattgga ggctacag                                                     18

<210> SEQ ID NO 15
<211> LENGTH: 18
<212> TYPE: DNA
<213> ORGANISM: Artificial
<220> FEATURE:
<223> OTHER INFORMATION: Oligonucleotides as PCR primer

<400> SEQUENCE: 15
tgacgcttcc aaagcaag                                                     18

<210> SEQ ID NO 16
<211> LENGTH: 18
<212> TYPE: DNA
<213> ORGANISM: Artificial
<220> FEATURE:
<223> OTHER INFORMATION: Oligonucleotides as PCR primer

<400> SEQUENCE: 16
ctccggaaac accaaagg                                                     18

<210> SEQ ID NO 17
<211> LENGTH: 906
<212> TYPE: DNA
<213> ORGANISM: Streptococcus equi

<400> SEQUENCE: 17
atgacaaaca aaacaaagcg tacaggattg gtacgcaagt acggtgcctg ctcagcagct        60
atcgccttag cagctcttgc aagcctggga gcaggtaaag cagtaaaggc agaccagcca       120
gcagcactaa aatatccaga acctagagac tattttcttc atactcgtga aggtgatgtt       180
atttatgatg aggatataaa aagatatttt gaggatttag aagcctattt aacagctaga       240
cttggtggga ttgataaaaa agtagaagaa gctgcccaaa agccaggtat tccaggtcct       300
actggccctc aaggtcctaa gggagacaaa ggagatccag gtgcccctgg tgagcgcggt       360
ccagctggac caagggcga tacgggcgaa gccggaccaa gaggtgagca aggcccagcc       420
ggacaagctg gagaacgtgg accaaaagga gatccaggtg ctccaggtcc taaaggtgaa       480
aagggtgata ctggtgcagt tggtcctaaa ggtgaaaaag gtgataccgg agcaaccgga       540
ccaaagggag acaagggcga acgcggtgaa aaaggcgagc aaggccaacg tggcgaaaaa       600
ggcgagcaag gccaacgcgg tgaaaaaggc gagcaaaaac caaagggtga tcaaggaaaa       660
gatacaaaac catcagctcc aaaagcacct gaaaaggctc ctgcaccaaa agctccaaag       720
gcttcagagc agtcatctaa tcctaaagca ccagctccta gtcagcacc aagcaaatca       780 gcggcaccaa caggtcaaaa agcagcccta ccagcaacag gggaaatcaa ccacccattc       840
ttcacccttg cagctcttag tgtcatcgct agcgtaggcg tcctaactct aaaaggaaaa       900
aaagac                                                                 906

<210> SEQ ID NO 18
<211> LENGTH: 302
<212> TYPE: PRT
<213> ORGANISM: Streptococcus equi

<400> SEQUENCE: 18

Met Thr Asn Lys Thr Lys Arg Thr Gly Leu Val Arg Lys Tyr Gly Ala
  1               5                  10                  15
```

```
Cys Ser Ala Ala Ile Ala Leu Ala Ala Leu Ala Ser Leu Gly Ala Gly
             20                  25                  30
Lys Ala Val Lys Ala Asp Gln Pro Ala Ala Leu Lys Tyr Pro Glu Pro
         35                  40                  45
Arg Asp Tyr Phe Leu His Thr Arg Glu Gly Asp Val Ile Tyr Asp Glu
     50                  55                  60
Asp Ile Lys Arg Tyr Phe Glu Asp Leu Glu Ala Tyr Leu Thr Ala Arg
 65                  70                  75                  80
Leu Gly Gly Ile Asp Lys Lys Val Glu Glu Ala Gln Lys Pro Gly
                 85                  90                  95
Ile Pro Gly Pro Thr Gly Pro Gln Gly Pro Lys Gly Asp Lys Gly Asp
             100                 105                 110
Pro Gly Ala Pro Gly Glu Arg Gly Pro Ala Gly Pro Lys Gly Asp Thr
         115                 120                 125
Gly Glu Ala Gly Pro Arg Gly Glu Gln Gly Pro Ala Gly Gln Ala Gly
     130                 135                 140
Glu Arg Gly Pro Lys Gly Asp Pro Gly Ala Pro Gly Pro Lys Gly Glu
145                 150                 155                 160
Lys Gly Asp Thr Gly Ala Val Gly Pro Lys Gly Lys Gly Asp Thr
             165                 170                 175
Gly Ala Thr Gly Pro Lys Gly Asp Lys Gly Glu Arg Gly Glu Lys Gly
         180                 185                 190
Glu Gln Gly Gln Arg Gly Glu Lys Gly Glu Gln Gly Gln Arg Gly Glu
     195                 200                 205
Lys Gly Glu Gln Lys Pro Lys Gly Asp Gln Gly Lys Asp Thr Lys Pro
210                 215                 220
Ser Ala Pro Lys Ala Pro Glu Lys Ala Pro Ala Pro Lys Ala Pro Lys
225                 230                 235                 240
Ala Ser Glu Gln Ser Ser Asn Pro Lys Ala Pro Ala Pro Lys Ser Ala
             245                 250                 255
Pro Ser Lys Ser Ala Ala Pro Thr Gly Gln Lys Ala Ala Leu Pro Ala
         260                 265                 270
Thr Gly Glu Ile Asn His Pro Phe Phe Thr Leu Ala Ala Leu Ser Val
     275                 280                 285
Ile Ala Ser Val Gly Val Leu Thr Leu Lys Gly Lys Lys Asp
290                 295                 300

<210> SEQ ID NO 19
<211> LENGTH: 1092
<212> TYPE: DNA
<213> ORGANISM: Streptococcus equi

<400> SEQUENCE: 19
atgatgaatc gtaaaaagca taccaaactc attcgtcact acagtatctg ctcagcagtg      60
gctgtcctag cagcagttag cttgggaaca ggtcaggacg tacaggcttc ggaacccaat     120
ccatatccag atgtgaggcg tttccttgat gagaagtacg atggagatgt ggataaatta     180
tctaaacaac ttcaaggtta ttttggtagt ttaagagagt atatagagtt tgaacttaaa     240
aatggcaaac aaggtcctgc tggccctcaa ggcccaaagg gtgataaagg agaccccgga     300
gagccaggtc ctcaaggtcc agtgggcccc gctggtccaa gggtgatcg tggtttagac     360 ggacgacgtg gcccagcagg tcagcaaggg gaagccggcc agttggtcc tcagggtcct     420 caaggcgagc aagggccaaa aggcgaccgt ggcgaacaag gaccaaaggg tgaacgcggt     480
gagcaaggac caaagggtga acgcggtgag caagggccaa aggcgaccg tggcgaacaa     540
```

-continued

```
ggaccaaagg gtgaacgcgg tgagcaagga ccaaagggtg aacgcggtga gcaagggcca      600
aaaggcgatc gtggcgagca aggaccaaag ggtgaacgcg gtgagcaagg ccaaaaggc       660 gatcgtggcg agcaaggacc aaaggtgaa cgcggtgagc aagggccaaa aggcgatcgt       720
ggcgagcaag gaccaaaggg tgatcgtggc gagcaaggac caaaggtga tcgtggcgaa       780 caaggaccaa aggtgatcg tggcgagcaa ggaccaaaag gtgaacgcgg tgagcaagga       840
ccaaaaggcg atcgtggcga gcaaggtcca agaaggagc cagaaaaaga caccaagcca       900
tcagtgccaa aggcaccaga taatatggct gcaccaaagg ctccggagaa gaagaaccct      960
aaagcaccgg ctcctaagtc agctccaaag gcatcattgc catcaacagg agacactagc     1020
caatcatttg ttgcagcagc ccttggcttt atcgctagcg cgggcttgct agtcttcaaa     1080
agaaagaaaa ac                                                         1092
```

<210> SEQ ID NO 20
<211> LENGTH: 364
<212> TYPE: PRT
<213> ORGANISM: Streptococcus equi

<400> SEQUENCE: 20

```
Met Met Asn Arg Lys Lys His Thr Lys Leu Ile Arg His Tyr Ser Ile
1               5                   10                  15

Cys Ser Ala Val Ala Val Leu Ala Ala Val Ser Leu Gly Thr Gly Gln
                20                  25                  30

Asp Val Gln Ala Ser Glu Pro Asn Pro Tyr Pro Asp Val Arg Arg Phe
            35                  40                  45

Leu Asp Glu Lys Tyr Asp Gly Asp Val Asp Lys Leu Ser Lys Gln Leu
        50                  55                  60

Gln Gly Tyr Phe Gly Ser Leu Arg Glu Tyr Ile Glu Phe Glu Leu Lys
65                  70                  75                  80

Asn Gly Lys Gln Gly Pro Ala Gly Pro Gln Gly Pro Lys Gly Asp Lys
                85                  90                  95

Gly Asp Pro Gly Glu Pro Gly Pro Gln Gly Pro Val Gly Pro Ala Gly
            100                 105                 110

Pro Lys Gly Asp Arg Gly Leu Asp Gly Arg Arg Gly Pro Ala Gly Gln
        115                 120                 125

Gln Gly Glu Ala Gly Pro Val Gly Pro Gln Gly Pro Gln Gly Glu Gln
    130                 135                 140

Gly Pro Lys Gly Asp Arg Gly Glu Gln Gly Pro Lys Gly Glu Arg Gly
145                 150                 155                 160

Glu Gln Gly Pro Lys Gly Glu Arg Gly Glu Gln Gly Pro Lys Gly Asp
                165                 170                 175

Arg Gly Glu Gln Gly Pro Lys Gly Glu Arg Gly Glu Gln Gly Pro Lys
            180                 185                 190

Gly Glu Arg Gly Glu Gln Gly Pro Lys Gly Asp Arg Gly Glu Gln Gly
        195                 200                 205

Pro Lys Gly Glu Arg Gly Glu Gln Gly Pro Lys Gly Asp Arg Gly Glu
    210                 215                 220

Gln Gly Pro Lys Gly Glu Arg Gly Glu Gln Gly Pro Lys Gly Asp Arg
225                 230                 235                 240

Gly Glu Gln Gly Pro Lys Gly Asp Arg Gly Glu Gln Gly Pro Lys Gly
                245                 250                 255

Asp Arg Gly Glu Gln Gly Pro Lys Gly Asp Arg Gly Glu Gln Gly Pro
            260                 265                 270
```

Lys Gly Glu Arg Gly Glu Gln Gly Pro Lys Gly Asp Arg Gly Glu Gln
            275                 280                 285

Gly Pro Lys Lys Glu Pro Glu Lys Asp Thr Lys Pro Ser Val Pro Lys
            290                 295                 300

Ala Pro Asp Asn Met Ala Ala Pro Lys Ala Pro Glu Lys Lys Asn Pro
305                 310                 315                 320

Lys Ala Pro Ala Pro Lys Ser Ala Pro Lys Ala Ser Leu Pro Ser Thr
            325                 330                 335

Gly Asp Thr Ser Gln Ser Phe Val Ala Ala Ala Leu Gly Phe Ile Ala
            340                 345                 350

Ser Ala Gly Leu Leu Val Phe Lys Arg Lys Lys Asn
            355                 360

<210> SEQ ID NO 21
<211> LENGTH: 2019
<212> TYPE: DNA
<213> ORGANISM: Streptococcus equi

<400> SEQUENCE: 21

```
atgataacta aaaacagag aaaactaaaa agacacacaa caatcagacg cctgtgtcat      60
caagccctag cagctaccct catcacagga agcctgatgg aacaggact acttggaaat     120 aaagtcgtgt atgggatat gaaaagcgat gccaaaaagg tattagcaac attgcaaaaa    180
ggtaatcata acaagagtt aaaaaaagtt cttagaacta ttggtgatga tagtttgcta    240
ttattatggt tacttgtatc gggtgattcc aatttagatg aaagtaataa agttttgat   300 tatttatcaa tttggaatac tggatctaga gttggtaaag tgatatctcc tactgaatac   360
tttaaacaag aatcaaaaaa cactgaaaat aggcaagctg tttatagtga atttaaacaa   420
cgcgtagaag aacgatctaa aaaagccaag gaagccactg aagcactaaa ccaaaaagct   480
caattggagg ctacagttaa aatataaac gaagaacttg aaaaaactag agaaggtttt    540
aaagttgtga gtgaaaactc aaacaaatta gaaaacaat taatggctga aaaataaaa    600 acacgtacag ctgaagaaac tgccaaacaa gctaaaaccg ataaagaaag agcagaggct   660
gaagctaaaa aagcgaaaga ggaagctaag actgcggaag aaaagttaa acaagcagaa   720 actgagaaaa ggaatgcgga agctaaggct agaaccgctg aagaagaagc taaacaagct   780
acggctgata agaaaaggc agagactgaa gctaaaaaag cgaagaaga agctaagacc    840 gctaagaag ctgctcatca agaacaagaa aaagctaaac aattagaaca agctaatcaa   900
caggctaacc aaagagctaa tctggcagaa aaatctaaaa aagatttaga aactcaaaaa   960 gaaaacttg aacaagagat taagaagct acagaagcta aaacaaagc cgagcaaaaa    1020 ttaaaagacc tacaagattc agctagtcaa ggcagtgaat tgtctaaaca gctgttaaaa   1080 gaaaagaag aattaacaac aaaacttcaa gagcttcaaa acaagctga ggaaaaaaca    1140 actgaaattg aaaagctaaa acaagagctt gaagctaata acaaaacag tggtcagcta   1200 ggtcaacagg aacaaaagct tcaagagcaa ttgaataagg ttcaaaaaga gctgaaacaa   1260
aaggaaatgg agttaaaaca agctcaagaa cagctgaaac aagaacaaaa acctcacgaa   1320
ggtggcggag attctgacgc ttccaaagca agaatcactg agctagaaaa acaagttcaa   1380
acactaacca aggaaaaggc agatctgtca tcaaccttg agtcaacaaa agctcaattg   1440
tcagagactc aagcaagact atcagaagct caaaacaat tgactgctgc tcaagaaaag   1500
ttaacaacac ttgaagccga gaaaacagcg cttcaacatc aagttgagac catttcaaaa   1560
```

-continued

```
cagctatcag aaacacgtga ccttagcgaa aaggaaaaag cagcactcca agagcaaatc    1620
aataagctaa aggctgagat tgagcaaaag accaaggaaa ttgaagcctt aaagcaaggc    1680
atgcaatcac atcaaggtca agaaaaacca aaggatccaa aaactccgga acaccaaag     1740 gatccaaaga ctcctgagaa aaacgatcag ccacaagcgc ctgaaaaacg tagtgtccct    1800
tggactgctc ttacaccagc taagccaatt gacactacca aagctcctaa gagctcagca    1860
ccaagcccac agactggggc agcaacacct aaaaaacaat taccagcaac tggtgataca    1920
gcgacaccta gcttctttac cgctgctgct atggcagtat tggctagtgc ctgtgcccta    1980
accctctcac ctagacgcaa aaagaatcaa aacaaccgt                          2019
```

<210> SEQ ID NO 22
<211> LENGTH: 673
<212> TYPE: PRT
<213> ORGANISM: Streptococcus equi

<400> SEQUENCE: 22

```
Met Ile Thr Lys Lys Gln Arg Lys Leu Lys Arg His Thr Thr Ile Arg
  1               5                  10                  15

Arg Leu Cys His Gln Ala Leu Ala Ala Thr Leu Ile Thr Gly Ser Leu
                 20                  25                  30

Met Gly Thr Gly Leu Leu Gly Asn Lys Val Val Tyr Gly Asp Met Lys
             35                  40                  45

Ser Asp Ala Lys Lys Val Leu Ala Thr Leu Gln Lys Gly Asn His Lys
         50                  55                  60

Gln Glu Leu Lys Lys Val Leu Arg Thr Ile Gly Asp Asp Ser Leu Leu
 65                  70                  75                  80

Leu Leu Trp Leu Leu Val Ser Gly Asp Ser Asn Leu Asp Glu Ser Asn
                 85                  90                  95

Lys Ser Phe Asp Tyr Leu Ser Ile Trp Asn Thr Gly Ser Arg Val Gly
                100                 105                 110

Lys Val Ile Ser Pro Thr Glu Tyr Phe Lys Gln Glu Ser Lys Asn Thr
            115                 120                 125

Glu Asn Arg Gln Ala Val Tyr Ser Glu Phe Lys Gln Arg Val Glu Glu
        130                 135                 140

Arg Ser Lys Lys Ala Lys Glu Ala Thr Glu Ala Leu Asn Gln Lys Ala
145                 150                 155                 160

Gln Leu Glu Ala Thr Val Lys Asn Ile Asn Glu Glu Leu Glu Lys Thr
                165                 170                 175

Arg Glu Gly Phe Lys Val Val Ser Glu Asn Ser Asn Lys Leu Glu Lys
            180                 185                 190

Gln Leu Met Ala Glu Lys Ile Lys Thr Arg Thr Ala Glu Glu Thr Ala
        195                 200                 205

Lys Gln Ala Lys Thr Asp Lys Glu Arg Ala Glu Ala Glu Ala Lys Lys
    210                 215                 220

Ala Lys Glu Glu Ala Lys Thr Ala Glu Gly Lys Val Lys Gln Ala Glu
225                 230                 235                 240

Thr Glu Lys Arg Asn Ala Glu Ala Lys Ala Arg Thr Ala Glu Glu Glu
                245                 250                 255

Ala Lys Gln Ala Thr Ala Asp Lys Glu Lys Ala Glu Thr Glu Ala Lys
            260                 265                 270

Lys Ala Lys Glu Glu Ala Lys Thr Ala Lys Glu Ala Ala His Gln Glu
        275                 280                 285

Gln Glu Lys Ala Lys Gln Leu Glu Gln Ala Asn Gln Gln Ala Asn Gln
```

```
            290                 295                 300
Arg Ala Asn Leu Ala Glu Lys Ser Lys Lys Asp Leu Glu Thr Gln Lys
305                 310                 315                 320

Glu Lys Leu Glu Gln Glu Ile Lys Glu Ala Thr Glu Ala Lys Asn Lys
                325                 330                 335

Ala Glu Gln Lys Leu Lys Asp Leu Gln Asp Ser Ala Ser Gln Gly Ser
            340                 345                 350

Glu Leu Ser Lys Gln Leu Leu Lys Glu Lys Glu Leu Thr Thr Lys
        355                 360                 365

Leu Gln Glu Leu Gln Lys Gln Ala Glu Lys Thr Thr Glu Ile Glu
370                 375                 380

Lys Leu Lys Gln Glu Leu Glu Ala Asn Lys Gln Asn Ser Gly Gln Leu
385                 390                 395                 400

Gly Gln Gln Glu Gln Lys Leu Gln Glu Gln Leu Asn Lys Val Gln Lys
                405                 410                 415

Glu Leu Lys Gln Lys Glu Met Glu Leu Lys Gln Ala Gln Glu Gln Leu
            420                 425                 430

Lys Gln Glu Gln Lys Pro His Glu Gly Gly Gly Asp Ser Asp Ala Ser
        435                 440                 445

Lys Ala Arg Ile Thr Glu Leu Glu Lys Gln Val Gln Thr Leu Thr Lys
450                 455                 460

Glu Lys Ala Asp Leu Ser Ser Thr Leu Glu Ser Thr Lys Ala Gln Leu
465                 470                 475                 480

Ser Glu Thr Gln Ala Arg Leu Ser Glu Ala Gln Lys Gln Leu Thr Ala
                485                 490                 495

Ala Gln Glu Lys Leu Thr Thr Leu Glu Ala Glu Lys Thr Ala Leu Gln
            500                 505                 510

His Gln Val Glu Thr Ile Ser Lys Gln Leu Ser Glu Thr Arg Asp Leu
        515                 520                 525

Ser Glu Lys Glu Lys Ala Ala Leu Gln Glu Gln Ile Asn Lys Leu Lys
530                 535                 540

Ala Glu Ile Glu Gln Lys Thr Lys Glu Ile Glu Ala Leu Lys Gln Gly
545                 550                 555                 560

Met Gln Ser His Gln Gly Gln Glu Lys Pro Lys Asp Pro Lys Thr Pro
                565                 570                 575

Glu Thr Pro Lys Asp Pro Lys Thr Pro Glu Lys Asn Asp Gln Pro Gln
            580                 585                 590

Ala Pro Glu Lys Arg Ser Val Pro Trp Thr Ala Leu Thr Pro Ala Lys
        595                 600                 605

Pro Ile Asp Thr Thr Lys Ala Pro Lys Ser Ser Ala Pro Ser Pro Gln
610                 615                 620

Thr Gly Ala Ala Thr Pro Lys Lys Gln Leu Pro Ala Thr Gly Asp Thr
625                 630                 635                 640

Ala Thr Pro Ser Phe Phe Thr Ala Ala Met Ala Val Leu Ala Ser
                645                 650                 655

Ala Cys Ala Leu Thr Leu Ser Pro Arg Arg Lys Lys Asn Gln Asn Asn
            660                 665                 670

Arg

<210> SEQ ID NO 23
<211> LENGTH: 1155
<212> TYPE: DNA
<213> ORGANISM: Streptococcus equi
```

<400> SEQUENCE: 23

```
atgatgaaaa aacaatcatt cacacactca cgtaaaccta aattcggtat gagaaaatta        60
tctattggcc ttgcctcatg tatgctagga atgatgttcc taacaacagg acatgtttct       120
ggtgaggtag ttgaagtttg gcctaatggg caaaatccta atggtaaaat agaaattcta       180
agtcaaactg agcactctga gcatttacag aaattacgcg atattgaaga tttccaagct       240
caaaagcaag ctgatcatgt tcgttacact aaatggttag atggggtaac tgttgatgag       300
catgaattca gaaaaatcaa ggaatatgac acagaatatt atgtaacacc tcttttaagt       360
ggtaaaggtt actatgatat caataaagat ttcaatcaag atagtgataa atgtgctgcc       420
gctgtagcgg ctaatatgtt ccattattgg tttgatagaa atagagacag tattaatcgt       480
ttcttaagtc aaagtccagg tgaaatggt gttattaaac ttgaaaatga aaaacaata         540
gaagtatcaa aattttagaa aacttaccgt agtgatggtg attatcttga taaaagtccg       600
ttttttgacc ttatcagtaa cagctttaaa ggtcctgttt gggcaaataa gctattggat       660
gcttacatta acggctatgg ttatatccat aaatttgcta aaaatactcc acattctaaa       720
aataataata gtaaatttaa tttctttaaa aaagtatttg atggtaatct cttgacagat       780
attcaccaaa ttttgatta taacactttt tcagataaat taagtgaggc tctctatact        840
ggtaaagcca ttggattggc ctacggacct ggagacttgc gtcgttcact aggtcatatt       900
atttctgtct ggggagctga tcttgacgat cagaatcgcg tggtagctat ttatgtaact       960
gattctgatg ataaaaagtt aactatagga aatgagagag ttggtttgaa gcgatataaa      1020
gtatctagcg atgatcaagg tcgtgctcgt ctgacgactc gtgataaaga taacacaggt      1080
ggtgaaattc gatctattga acattagat atgggtacac aagagtggc agattacttc        1140
aacaagacag aaaaa                                                      1155
```

<210> SEQ ID NO 24
<211> LENGTH: 385
<212> TYPE: PRT
<213> ORGANISM: Streptococcus equi

<400> SEQUENCE: 24

```
Met Met Lys Lys Gln Ser Phe Thr His Ser Arg Lys Pro Lys Phe Gly
1               5                   10                  15

Met Arg Lys Leu Ser Ile Gly Leu Ala Ser Cys Met Leu Gly Met Met
            20                  25                  30

Phe Leu Thr Thr Gly His Val Ser Gly Glu Val Glu Val Trp Pro
        35                  40                  45

Asn Gly Gln Asn Pro Asn Gly Lys Ile Glu Ile Leu Ser Gln Thr Glu
    50                  55                  60

His Ser Glu His Leu Gln Lys Leu Arg Asp Ile Glu Asp Phe Gln Ala
65                  70                  75                  80

Gln Lys Gln Ala Asp His Val Arg Tyr Thr Lys Trp Leu Asp Gly Val
                85                  90                  95

Thr Val Asp Glu His Glu Phe Arg Lys Ile Lys Glu Tyr Asp Thr Glu
            100                 105                 110

Tyr Tyr Val Thr Pro Leu Leu Ser Gly Lys Gly Tyr Tyr Asp Ile Asn
        115                 120                 125

Lys Asp Phe Asn Gln Asp Ser Asp Lys Cys Ala Ala Val Ala Ala
    130                 135                 140

Asn Met Phe His Tyr Trp Phe Asp Arg Asn Arg Asp Ser Ile Asn Arg
145                 150                 155                 160
```

```
Phe Leu Ser Gln Ser Pro Gly Glu Asn Gly Val Ile Lys Leu Glu Asn
                165                 170                 175

Glu Lys Thr Ile Glu Val Ser Lys Phe Leu Glu Thr Tyr Arg Ser Asp
            180                 185                 190

Gly Asp Tyr Leu Asp Lys Ser Pro Phe Asp Leu Ile Ser Asn Ser
        195                 200                 205

Phe Lys Gly Pro Val Trp Ala Asn Lys Leu Leu Asp Ala Tyr Ile Asn
    210                 215                 220

Gly Tyr Gly Tyr Ile His Lys Phe Ala Lys Asn Thr Pro His Ser Lys
225                 230                 235                 240

Asn Asn Asn Ser Lys Phe Asn Phe Phe Lys Lys Val Phe Asp Gly Asn
                245                 250                 255

Leu Leu Thr Asp Ile His Gln Ile Phe Asp Tyr Asn Thr Phe Ser Asp
            260                 265                 270

Lys Leu Ser Glu Ala Leu Tyr Thr Gly Lys Ala Ile Gly Leu Ala Tyr
        275                 280                 285

Gly Pro Gly Asp Leu Arg Arg Ser Leu Gly His Ile Ile Ser Val Trp
    290                 295                 300

Gly Ala Asp Leu Asp Asp Gln Asn Arg Val Val Ala Ile Tyr Val Thr
305                 310                 315                 320

Asp Ser Asp Asp Lys Lys Leu Thr Ile Gly Asn Glu Arg Val Gly Leu
                325                 330                 335

Lys Arg Tyr Lys Val Ser Ser Asp Asp Gln Gly Arg Ala Arg Leu Thr
            340                 345                 350

Thr Arg Asp Lys Asp Asn Thr Gly Gly Glu Ile Arg Ser Ile Glu Thr
        355                 360                 365

Leu Asp Met Gly Thr Gln Glu Trp Ala Asp Tyr Phe Asn Lys Thr Glu
    370                 375                 380

Lys
385

<210> SEQ ID NO 25
<211> LENGTH: 930
<212> TYPE: DNA
<213> ORGANISM: Streptococcus equi

<400> SEQUENCE: 25
atgaaaaaga aacttagcct ggccttgagt gcttttttgg ctgttttcat gctggttgcc      60
tgctctaatg gtggaaacaa ggaagctaag agtgacaagc tcaaggttgt ggttaccaat     120
tccattattg ctgacatgac taaaaatatt gcaggtgaca agattgactt gcacagcatt     180
gtgccgattg tcaagatcc gcatgagtat gagccattgc cagaagacgt tgaagagacc      240
agcaatgccg atcttattct ctataacggt attaaccttg aagacggcgg acaggcttgg     300
tttacaaagc ttgtaaaaaa tgctaagaag gaaaaggaca aggactactt cgctgtatct     360
gatggtattg atgtgattta cctagaaggt gaaagtgaaa aaggcaagga agaccctcat     420
gcttggttga atcttgaaaa tggggttatc tattcaaaaa atattgcaaa gcaattgatc     480
gctaaagacc ctaaaaacaa ggaaacctat gaaacaacc taaaagctta cgttgagaag     540
ctagagaagc ttgataagga agcaaaatca aaatttgatg ctattgctga caataaaaag     600
ctaatcgtca caagtgaagg ctgcttcaaa tacttctcaa agcttacgg tgtcccatca      660 gcctacatct gggaaatcaa cactgaagaa gaaggaactc cggatcaaat tcatcattg      720 atcgaaaaat tgaaagacgt taagccatca gcgctttttg ttgagtcaag tgttgacaga     780
```

```
cgtccaatgg agactgtttc taaggacagt ggtattccga tctatgcaga aatctttact    840
gactctgtag ccaaaaaagg ccaagatgga gacagctact atgccatgat gaaatggaac    900
cttgataaaa tttctgaagg cttagcaaaa                                     930
```

<210> SEQ ID NO 26
<211> LENGTH: 310
<212> TYPE: PRT
<213> ORGANISM: Streptococcus equi

<400> SEQUENCE: 26

```
Met Lys Lys Lys Leu Ser Leu Ala Leu Ser Ala Phe Leu Ala Val Phe
1               5                   10                  15

Met Leu Val Ala Cys Ser Asn Gly Gly Asn Lys Glu Ala Lys Ser Asp
            20                  25                  30

Lys Leu Lys Val Val Thr Asn Ser Ile Ile Ala Asp Met Thr Lys
        35                  40                  45

Asn Ile Ala Gly Asp Lys Ile Asp Leu His Ser Ile Val Pro Ile Gly
50                  55                  60

Gln Asp Pro His Glu Tyr Glu Pro Leu Pro Asp Val Glu Lys Thr
65                  70                  75                  80

Ser Asn Ala Asp Leu Ile Leu Tyr Asn Gly Ile Asn Leu Glu Asp Gly
                85                  90                  95

Gly Gln Ala Trp Phe Thr Lys Leu Val Lys Asn Ala Lys Lys Glu Lys
            100                 105                 110

Asp Lys Asp Tyr Phe Ala Val Ser Asp Gly Ile Asp Val Ile Tyr Leu
        115                 120                 125

Glu Gly Glu Ser Glu Lys Gly Lys Glu Asp Pro His Ala Trp Leu Asn
130                 135                 140

Leu Glu Asn Gly Val Ile Tyr Ser Lys Asn Ile Ala Lys Gln Leu Ile
145                 150                 155                 160

Ala Lys Asp Pro Lys Asn Lys Glu Thr Tyr Glu Asn Asn Leu Lys Ala
                165                 170                 175

Tyr Val Glu Lys Leu Glu Lys Leu Asp Lys Glu Ala Lys Ser Lys Phe
            180                 185                 190

Asp Ala Ile Ala Asp Asn Lys Lys Leu Ile Val Thr Ser Glu Gly Cys
        195                 200                 205

Phe Lys Tyr Phe Ser Lys Ala Tyr Gly Val Pro Ser Ala Tyr Ile Trp
210                 215                 220

Glu Ile Asn Thr Glu Glu Gly Thr Pro Asp Gln Ile Ser Ser Leu
225                 230                 235                 240

Ile Glu Lys Leu Lys Asp Val Lys Pro Ser Ala Leu Phe Val Glu Ser
                245                 250                 255

Ser Val Asp Arg Arg Pro Met Glu Thr Val Ser Lys Asp Ser Gly Ile
            260                 265                 270

Pro Ile Tyr Ala Glu Ile Phe Thr Asp Ser Val Ala Lys Lys Gly Gln
        275                 280                 285

Asp Gly Asp Ser Tyr Tyr Ala Met Met Lys Trp Asn Leu Asp Lys Ile
290                 295                 300

Ser Glu Gly Leu Ala Lys
305                 310
```

<210> SEQ ID NO 27
<211> LENGTH: 1287
<212> TYPE: DNA

<213> ORGANISM: Streptococcus equi

<400> SEQUENCE: 27

```
atggaaaaaa acaaaaaggt atcctacttt ttacgtcaat cagctgttgg tttagcttca      60
gtgtcggcag cctttctggt tggaacgact tcagtgggtg ctttagacgc agcaacagtg     120
ttagagccta acagccttt cattagagaa gctgttaggg aaatcaatca gctgagtgat     180
gactacgctg acaatcaaga gcttcaggct gttcttgcta atgctggagt tgaggcactt     240
gctgcagata ctgttgatca ggctaaagca gctcttgaca agcaaaggc agctgttgct      300
ggtgttcagc ttgatgaagc aagacgtgag gcttacagaa caatcaatgc cttaagtgat     360
cagcacaaaa gcgatcaaaa ggttcagcta gctctagttg ctgcagcagc taaggtggca     420
gatgctgctt cagttgatca agtgaatgca gccattaatg atgctcatac agctattgcg     480
gacattacag gagcagcctt gttggaggct aaagaagctg ctatcaatga actaaagcag     540
tatggcatta gtgattacta tgtgacctta atcaacaaag ccaaaactgt tgaaggtgtc     600
aatgcgctta aggcagagat tttatcagct ctaccgagtt ctgaggtcat tgacgcagca     660
gaactaacac cagccttgac tagctataag cttgtcatca agggagcaac ttttcaggt      720
gaaacagcta ctaaggcagt agacgcagct gtagctgagc agaccttcag agactatgct     780
aataaaaatg gtgtagacgg cgtttgggct tatgatgctg ccacaaagac atttacagtc     840
actgaacagc ctgtagctga gactattgag gcggcagaat taacaccagc tttgaccacc     900
tataggcttg ttattaaggg ggttaccttc tcaggtgaaa cagctaccaa ggcagtagac     960
gcagccacag ccgagcagac cttcaggcaa tatgccaatg acaatggcgt tactggtgaa    1020
tgggcttatg acgctgctac aaagacattt acagtcactg aggctttaga ggagagtcca    1080
gctgatccag aaaagccatc agcttctctt ccgttgacac cgcttacacc agcaactaag    1140
acagcaccag ctaagcaaaa agataagcaa aaggctaaga ctcttccaac gactggtgag    1200
aaggctaatc cattctttac agcagcggct cttgccatta tggcgagtgc aggtgcttta    1260
gcagtgactt caaagcgtca gcaggac                                       1287
```

<210> SEQ ID NO 28
<211> LENGTH: 429
<212> TYPE: PRT
<213> ORGANISM: Streptococcus equi

<400> SEQUENCE: 28

```
Met Glu Lys Asn Lys Lys Val Ser Tyr Phe Leu Arg Gln Ser Ala Val
 1               5                  10                  15

Gly Leu Ala Ser Val Ser Ala Ala Phe Leu Val Gly Thr Thr Ser Val
                20                  25                  30

Gly Ala Leu Asp Ala Ala Thr Val Leu Glu Pro Thr Thr Ala Phe Ile
            35                  40                  45

Arg Glu Ala Val Arg Glu Ile Asn Gln Leu Ser Asp Asp Tyr Ala Asp
        50                  55                  60

Asn Gln Glu Leu Gln Ala Val Leu Ala Asn Ala Gly Val Glu Ala Leu
    65                  70                  75                  80

Ala Ala Asp Thr Val Asp Gln Ala Lys Ala Ala Leu Asp Lys Ala Lys
                85                  90                  95

Ala Ala Val Ala Gly Val Gln Leu Asp Glu Ala Arg Arg Glu Ala Tyr
            100                 105                 110

Arg Thr Ile Asn Ala Leu Ser Asp Gln His Lys Ser Asp Gln Lys Val
        115                 120                 125
```

Gln Leu Ala Leu Val Ala Ala Ala Lys Val Ala Asp Ala Ala Ser
    130                 135                 140

Val Asp Gln Val Asn Ala Ala Ile Asn Asp Ala His Thr Ala Ile Ala
145                 150                 155                 160

Asp Ile Thr Gly Ala Ala Leu Leu Glu Ala Lys Glu Ala Ala Ile Asn
                165                 170                 175

Glu Leu Lys Gln Tyr Gly Ile Ser Asp Tyr Tyr Val Thr Leu Ile Asn
            180                 185                 190

Lys Ala Lys Thr Val Glu Gly Val Asn Ala Leu Lys Ala Glu Ile Leu
        195                 200                 205

Ser Ala Leu Pro Ser Ser Glu Val Ile Asp Ala Ala Glu Leu Thr Pro
    210                 215                 220

Ala Leu Thr Ser Tyr Lys Leu Val Ile Lys Gly Ala Thr Phe Ser Gly
225                 230                 235                 240

Glu Thr Ala Thr Lys Ala Val Asp Ala Ala Val Ala Glu Gln Thr Phe
                245                 250                 255

Arg Asp Tyr Ala Asn Lys Asn Gly Val Asp Gly Val Trp Ala Tyr Asp
            260                 265                 270

Ala Ala Thr Lys Thr Phe Thr Val Thr Glu Gln Pro Val Ala Glu Thr
        275                 280                 285

Ile Glu Ala Ala Glu Leu Thr Pro Ala Leu Thr Thr Tyr Arg Leu Val
    290                 295                 300

Ile Lys Gly Val Thr Phe Ser Gly Glu Thr Ala Thr Lys Ala Val Asp
305                 310                 315                 320

Ala Ala Thr Ala Glu Gln Thr Phe Arg Gln Tyr Ala Asn Asp Asn Gly
                325                 330                 335

Val Thr Gly Glu Trp Ala Tyr Asp Ala Ala Thr Lys Thr Phe Thr Val
            340                 345                 350

Thr Glu Ala Leu Glu Glu Ser Pro Ala Asp Pro Glu Lys Pro Ser Ala
        355                 360                 365

Ser Leu Pro Leu Thr Pro Leu Thr Pro Ala Thr Lys Thr Ala Pro Ala
    370                 375                 380

Lys Gln Lys Asp Lys Gln Lys Ala Lys Thr Leu Pro Thr Thr Gly Glu
385                 390                 395                 400

Lys Ala Asn Pro Phe Phe Thr Ala Ala Leu Ala Ile Met Ala Ser
                405                 410                 415

Ala Gly Ala Leu Ala Val Thr Ser Lys Arg Gln Gln Asp
        420                 425

<210> SEQ ID NO 29
<211> LENGTH: 2004
<212> TYPE: DNA
<213> ORGANISM: Streptococcus equi

<400> SEQUENCE: 29
atgcaaatca ataatgtaaa aggaggattt tgtttgaaac aactgacaaa gatcgttagt      60
gtggtcttgt tgctggtctt tacccttagt gctagcctgc acaaggttcg ggcaactaat     120
cttagtgaca acatcacatc attgacggtt gcttcttcat cactccgaga tggagagaga     180
acgacggtaa aggttgcgtt tgatgacaaa aaacagaaaa tcaaggcagg ggatacgata     240 gaggtcaccct ggcctacaag tggtaatgtc tacattcagg ctttaataaa accataccg     300 cttaatatta gagggtagta tgttggtacc ttggaggtca cgctagcaaa ggctgttttc     360
acattcaatc aaaatattga acaatgcatg atgtctctg gttggggaga gtttgatatt     420

```
actgttagaa atgtgacaca aaccaccgct gaaacatcag gaacgaccac agtaaaggta      480
ggcaatcgca ctgctactat cactgttact aagcctgagg caggcactgg taccagctca      540
ttttattata agactggtga tatgcagccc aatgatactg agcgtgtgag atggttcctg      600
ctgattaaca acaacaagga tgggtggcc aatactgtta cagtcgaaga cgatattcaa       660
ggtggtcaaa ccttggatat gagcagcttt gacatcaccg tatctggtta tcgtaacgag      720
cgcttcgttg gggaaaacgc tctgacagag tttcatacaa catttccaaa ttctgtcatt      780
acggcaacag ataatcacat tagtgtgcgg ttagatcaat atgatgcctc acaaaacact      840
gtcaacattg cttataagac aaagataacg gactttgacc aaaaagaatt tgccaacaac      900
agtaaaatct ggtaccagat tttatacaag gatcaggtat cgggtcaaga gtcaaaccac      960
caagtagcca atatcaatgc taacggcggg gttgatggca gtcgctatac cagctttact      1020
gtcaagaaaa tttggaatga caaggaaaat caagacggta agcgtccaaa gactattact      1080
gttcagcttt acgccaatga tcagaaagtt aatgataaga ccattgaatt gagtgatact      1140
aatagctggc aagcaagttt tggtaagctg gataagtatg acagtcagaa ccaaaaaatt      1200
acctacagtg tcaaggaagt gatggttcct gttggctacc aatcgcaggt tgaggggat       1260 agtggagtag gatttaccat taccaacacc tatacaccag aggtcattag cattaccggt      1320
caaaaaactt gggacgacag ggaaaaccaa gacggtaaac gtcctaagga gattacggtt      1380
cgtttattgg caaatgacgc tgcaactgac aaggtagcaa ctgcttcaga gcaaaccggc      1440
tggaagtata catttaccaa tctaccgaaa tacaaagatg gtaaacagat cacctacacg      1500
atccaagagg accctgtggc agattacacc acaaccattc agggatttga tattaccaat      1560
catcatgagg tagccttgac cagcctaaag gtcatcaagg tttggaatga taggacgat       1620 tattaccata acgtcccaa ggagattacc attttgctaa aggcagatgg caaggtgatt       1680
cgtgaacatc agatgacacc ggatcagcaa ggaaaatggg aatacacctt tgaccagctg      1740
ccggtctatc agacaggcaa gaaaatcagc tacagcattg aggaaaaaca ggttgctggc      1800
tatcaagccc ctgtctatga ggttgatgaa ggcttgaagc aggtcactgt aaccaacacc      1860
cttaacccaa gctacaagct gcctgacacc ggaggacaag gagtgaaatg gtacctgtta      1920
atcggtggcg gtttatcat cgtcgcaatc cttgtactga tcagcctta tcaaaaacac        1980 aagcgccata acatgtcaaa acca                                              2004
```

<210> SEQ ID NO 30
<211> LENGTH: 668
<212> TYPE: PRT
<213> ORGANISM: Streptococcus equi

<400> SEQUENCE: 30

```
Met Gln Ile Asn Asn Val Lys Gly Gly Phe Cys Leu Lys Gln Leu Thr
1               5                   10                  15

Lys Ile Val Ser Val Val Leu Leu Val Phe Thr Leu Ser Ala Ser
            20                  25                  30

Leu His Lys Val Arg Ala Thr Asn Leu Ser Asp Asn Ile Thr Ser Leu
        35                  40                  45

Thr Val Ala Ser Ser Leu Arg Asp Gly Glu Arg Thr Thr Val Lys
    50                  55                  60

Val Ala Phe Asp Asp Lys Lys Gln Lys Ile Lys Ala Gly Asp Thr Ile
65                  70                  75                  80

Glu Val Thr Trp Pro Thr Ser Gly Asn Val Tyr Ile Gln Gly Phe Asn
```

-continued

```
                85                  90                  95
Lys Thr Ile Pro Leu Asn Ile Arg Gly Val Asp Val Gly Thr Leu Glu
                100                 105                 110

Val Thr Leu Asp Lys Ala Val Phe Thr Phe Asn Gln Asn Ile Glu Thr
            115                 120                 125

Met His Asp Val Ser Gly Trp Gly Glu Phe Asp Ile Thr Val Arg Asn
        130                 135                 140

Val Thr Gln Thr Thr Ala Glu Thr Ser Gly Thr Thr Val Lys Val
145                 150                 155                 160

Gly Asn Arg Thr Ala Thr Ile Thr Val Thr Lys Pro Glu Ala Gly Thr
                165                 170                 175

Gly Thr Ser Ser Phe Tyr Tyr Lys Thr Gly Asp Met Gln Pro Asn Asp
                180                 185                 190

Thr Glu Arg Val Arg Trp Phe Leu Leu Ile Asn Asn Asn Lys Glu Trp
            195                 200                 205

Val Ala Asn Thr Val Thr Val Glu Asp Asp Ile Gln Gly Gly Gln Thr
        210                 215                 220

Leu Asp Met Ser Ser Phe Asp Ile Thr Val Ser Gly Tyr Arg Asn Glu
225                 230                 235                 240

Arg Phe Val Gly Glu Asn Ala Leu Thr Glu Phe His Thr Thr Phe Pro
                245                 250                 255

Asn Ser Val Ile Thr Ala Thr Asp Asn His Ile Ser Val Arg Leu Asp
                260                 265                 270

Gln Tyr Asp Ala Ser Gln Asn Thr Val Asn Ile Ala Tyr Lys Thr Lys
            275                 280                 285

Ile Thr Asp Phe Asp Gln Lys Glu Phe Ala Asn Asn Ser Lys Ile Trp
        290                 295                 300

Tyr Gln Ile Leu Tyr Lys Asp Gln Val Ser Gly Gln Glu Ser Asn His
305                 310                 315                 320

Gln Val Ala Asn Ile Asn Ala Asn Gly Gly Val Asp Gly Ser Arg Tyr
                325                 330                 335

Thr Ser Phe Thr Val Lys Lys Ile Trp Asn Asp Lys Glu Asn Gln Asp
                340                 345                 350

Gly Lys Arg Pro Lys Thr Ile Thr Val Gln Leu Tyr Ala Asn Asp Gln
            355                 360                 365

Lys Val Asn Asp Lys Thr Ile Glu Leu Ser Asp Thr Asn Ser Trp Gln
        370                 375                 380

Ala Ser Phe Gly Lys Leu Asp Lys Tyr Asp Ser Gln Asn Gln Lys Ile
385                 390                 395                 400

Thr Tyr Ser Val Lys Glu Val Met Val Pro Val Gly Tyr Gln Ser Gln
                405                 410                 415

Val Glu Gly Asp Ser Gly Val Gly Phe Thr Ile Thr Asn Thr Tyr Thr
                420                 425                 430

Pro Glu Val Ile Ser Ile Thr Gly Gln Lys Thr Trp Asp Asp Arg Glu
            435                 440                 445

Asn Gln Asp Gly Lys Arg Pro Lys Glu Ile Thr Val Arg Leu Leu Ala
        450                 455                 460

Asn Asp Ala Ala Thr Asp Lys Val Ala Thr Ala Ser Glu Gln Thr Gly
465                 470                 475                 480

Trp Lys Tyr Thr Phe Thr Asn Leu Pro Lys Tyr Lys Asp Gly Lys Gln
                485                 490                 495

Ile Thr Tyr Thr Ile Gln Glu Asp Pro Val Ala Asp Tyr Thr Thr Thr
                500                 505                 510
```

```
Ile Gln Gly Phe Asp Ile Thr Asn His His Glu Val Ala Leu Thr Ser
        515                 520                 525

Leu Lys Val Ile Lys Val Trp Asn Asp Lys Asp Tyr Tyr His Lys
    530                 535                 540

Arg Pro Lys Glu Ile Thr Ile Leu Leu Lys Ala Asp Gly Lys Val Ile
545                 550                 555                 560

Arg Glu His Gln Met Thr Pro Asp Gln Gly Lys Trp Glu Tyr Thr
                565                 570                 575

Phe Asp Gln Leu Pro Val Tyr Gln Thr Gly Lys Lys Ile Ser Tyr Ser
            580                 585                 590

Ile Glu Glu Lys Gln Val Ala Gly Tyr Gln Ala Pro Val Tyr Glu Val
        595                 600                 605

Asp Glu Gly Leu Lys Gln Val Thr Val Thr Asn Thr Leu Asn Pro Ser
    610                 615                 620

Tyr Lys Leu Pro Asp Thr Gly Gln Gly Val Lys Trp Tyr Leu Leu
625                 630                 635                 640

Ile Gly Gly Gly Phe Ile Ile Val Ala Ile Leu Val Leu Ile Ser Leu
                645                 650                 655

Tyr Gln Lys His Lys Arg His Asn Met Ser Lys Pro
            660                 665

<210> SEQ ID NO 31
<211> LENGTH: 165
<212> TYPE: DNA
<213> ORGANISM: Streptococcus equi

<400> SEQUENCE: 31
cagccagcag cactaaaata tccagaacct agagactatt ttcttcatac tcgtgaaggt    60
gatgttattt atgatgagga tataaaaaga tattttgagg atttagaagc ctatttaaca   120
gctagacttg gtgggattga taaaaaagta gaagaagctg cccaa                   165

<210> SEQ ID NO 32
<211> LENGTH: 55
<212> TYPE: PRT
<213> ORGANISM: Streptococcus equi

<400> SEQUENCE: 32

Gln Pro Ala Ala Leu Lys Tyr Pro Glu Pro Arg Asp Tyr Phe Leu His
1               5                   10                  15

Thr Arg Glu Gly Asp Val Ile Tyr Asp Glu Asp Ile Lys Arg Tyr Phe
            20                  25                  30

Glu Asp Leu Glu Ala Tyr Leu Thr Ala Arg Leu Gly Gly Ile Asp Lys
        35                  40                  45

Lys Val Glu Glu Ala Ala Gln
    50                  55

<210> SEQ ID NO 33
<211> LENGTH: 135
<212> TYPE: DNA
<213> ORGANISM: Streptococcus equi

<400> SEQUENCE: 33
tcggaaccca atccatatcc agatgtgagg cgtttccttg atgagaagta cgatggagat    60
gtggataaat tatctaaaca acttcaaggt tattttggta gtttaagaga gtatatagag   120
tttgaactta aaaat                                                   135
```

<210> SEQ ID NO 34
<211> LENGTH: 45
<212> TYPE: PRT
<213> ORGANISM: Streptococcus equi

<400> SEQUENCE: 34

```
Ser Glu Pro Asn Pro Tyr Pro Asp Val Arg Arg Phe Leu Asp Glu Lys
1               5                   10                  15
Tyr Asp Gly Asp Val Asp Lys Leu Ser Lys Gln Leu Gln Gly Tyr Phe
            20                  25                  30
Gly Ser Leu Arg Glu Tyr Ile Glu Phe Glu Leu Lys Asn
        35                  40                  45
```

<210> SEQ ID NO 35
<211> LENGTH: 1827
<212> TYPE: DNA
<213> ORGANISM: Streptococcus equi

<400> SEQUENCE: 35

| | | | | | |
|---|---|---|---|---|---|
| gctaccctca | tcacaggaag | cctgatggga | acaggactac | ttggaaataa | agtcgtgtat | 60 |
| ggggatatga | aaagcgatgc | caaaaaggta | ttagcaacat | tgcaaaaagg | taatcataaa | 120 |
| caagagttaa | aaaagttcct | tagaactatt | ggtgatgata | gtttgctatt | attatggtta | 180 |
| cttgtatcgg | gtgattccaa | tttagatgaa | agtaataaaa | gttttgatta | tttatcaatt | 240 |
| tggaatactg | gatctagagt | tggtaaagtg | atatctccta | ctgaatactt | taaacaagaa | 300 |
| tcaaaaaaca | ctgaaaatag | gcaagctgtt | tatagtgaat | ttaaacaacg | cgtagaagaa | 360 |
| cgatctaaaa | aagccaagga | agccactgaa | gcactaaacc | aaaaagctca | attggaggct | 420 |
| acagttaaaa | atataaacga | agaacttgaa | aaaactagaa | aaggttttaa | agttgtgagt | 480 |
| gaaaactcaa | acaaattaga | aaaacaatta | atggctgaga | aaataaaaac | acgtacagct | 540 |
| gaagaaactg | ccaaacaagc | taaaaccgat | aaagaaagag | cagaggctga | agctaaaaaa | 600 |
| gcgaaagagg | aagctaagac | tgcggaagga | aaagttaaac | aagcagaaac | tgagaaaagg | 660 |
| aatgcggaag | ctaaggctag | aaccgctgaa | gaagaagcta | acaagctac | ggctgataaa | 720 |
| gaaaaggcag | agactgaagc | taaaaaagcg | aagaagaag | ctaagaccgc | taaagaagct | 780 |
| gctcatcaag | aacaagaaaa | agctaaacaa | ttagaacaag | ctaatcaaca | ggctaaccaa | 840 |
| agagctaatc | tggcagaaaa | atctaaaaaa | gatttagaaa | ctcaaaaaga | aaaacttgaa | 900 |
| caagagatta | agaagctac | agaagctaaa | aacaaagccg | agcaaaaatt | aaaagaccta | 960 |
| caagattcag | ctagtcaagg | cagtgaattg | tctaaacagc | tgttaaaaga | aaagaagaa | 1020 |
| ttaacaacaa | aacttcaaga | gcttcaaaaa | caagctgagg | aaaaaacaac | tgaaattgaa | 1080 |
| aagctaaaac | aagagcttga | agctaataaa | caaacagtg | gtcagctagg | tcaacaggaa | 1140 |
| caaaagcttc | aagagcaatt | gaataaggtt | caaaagagc | tgaaacaaaa | ggaaatggag | 1200 |
| ttaaaacaag | ctcaagaaca | gctgaaacaa | gaacaaaaac | ctcacgaagg | tggcggagat | 1260 |
| tctgacgctt | ccaaagcaag | aatcactgag | ctagaaaaac | aagttcaaac | actaaccaag | 1320 |
| gaaaaggcag | atctgtcatc | aaccccttgag | tcaacaaaag | ctcaattgtc | agagactcaa | 1380 |
| gcaagactat | cagaagctca | aaaacaattg | actgctgctc | aagaaaagtt | aacaacactt | 1440 |
| gaagccgaga | aaacagcgct | tcaacatcaa | gttgagacca | tttcaaaaca | gctatcagaa | 1500 |
| acacgtgacc | ttagcgaaaa | ggaaaaagca | gcactccaag | agcaaatcaa | taagctaaag | 1560 |
| gctgagattg | agcaaaagac | caaggaaatt | gaagccttaa | agcaaggcat | gcaatcacat | 1620 |

-continued

```
caaggtcaag aaaaaccaaa ggatccaaaa actccggaaa caccaaagga tccaaagact      1680
cctgagaaaa acgatcagcc acaagcgcct gaaaaacgta gtgtcccttg gactgctctt      1740
acaccagcta agccaattga cactaccaaa gctcctaaga gctcagcacc aagcccacag      1800
actggggcag caacacctaa aaaacaa                                          1827
```

<210> SEQ ID NO 36
<211> LENGTH: 609
<212> TYPE: PRT
<213> ORGANISM: Streptococcus equi

<400> SEQUENCE: 36

| | | | | | | | | | | | | | | |
|---|---|---|---|---|---|---|---|---|---|---|---|---|---|---|
| Ala | Thr | Leu | Ile | Thr | Gly | Ser | Leu | Met | Gly | Thr | Gly | Leu | Leu | Gly | Asn |
| 1 | | | | 5 | | | | | 10 | | | | | 15 | |
| Lys | Val | Val | Tyr | Gly | Asp | Met | Lys | Ser | Asp | Ala | Lys | Lys | Val | Leu | Ala |
| | | | 20 | | | | | 25 | | | | | 30 | | |
| Thr | Leu | Gln | Lys | Gly | Asn | His | Lys | Gln | Glu | Leu | Lys | Lys | Val | Leu | Arg |
| | | | | 35 | | | | | 40 | | | | 45 | | |
| Thr | Ile | Gly | Asp | Asp | Ser | Leu | Leu | Leu | Leu | Trp | Leu | Leu | Val | Ser | Gly |
| | 50 | | | | | 55 | | | | | 60 | | | | |
| Asp | Ser | Asn | Leu | Asp | Glu | Ser | Asn | Lys | Ser | Phe | Asp | Tyr | Leu | Ser | Ile |
| 65 | | | | | 70 | | | | | 75 | | | | | 80 |
| Trp | Asn | Thr | Gly | Ser | Arg | Val | Gly | Lys | Val | Ile | Ser | Pro | Thr | Glu | Tyr |
| | | | | 85 | | | | | 90 | | | | | 95 | |
| Phe | Lys | Gln | Glu | Ser | Lys | Asn | Thr | Glu | Asn | Arg | Gln | Ala | Val | Tyr | Ser |
| | | | | 100 | | | | | 105 | | | | | 110 | |
| Glu | Phe | Lys | Gln | Arg | Val | Glu | Glu | Arg | Ser | Lys | Ala | Lys | Glu | Ala |
| | | 115 | | | | | 120 | | | | | 125 | | | |
| Thr | Glu | Ala | Leu | Asn | Gln | Lys | Ala | Gln | Leu | Glu | Ala | Thr | Val | Lys | Asn |
| | 130 | | | | | 135 | | | | | 140 | | | | |
| Ile | Asn | Glu | Glu | Leu | Glu | Lys | Thr | Arg | Glu | Gly | Phe | Lys | Val | Val | Ser |
| 145 | | | | | 150 | | | | | 155 | | | | | 160 |
| Glu | Asn | Ser | Asn | Lys | Leu | Glu | Lys | Gln | Leu | Met | Ala | Glu | Lys | Ile | Lys |
| | | | | 165 | | | | | 170 | | | | | 175 | |
| Thr | Arg | Thr | Ala | Glu | Glu | Thr | Ala | Lys | Gln | Ala | Lys | Thr | Asp | Lys | Glu |
| | | | 180 | | | | | 185 | | | | | 190 | | |
| Arg | Ala | Glu | Ala | Glu | Ala | Lys | Lys | Ala | Lys | Glu | Ala | Lys | Thr | Ala |
| | | 195 | | | | | 200 | | | | | 205 | | | |
| Glu | Gly | Lys | Val | Lys | Gln | Ala | Glu | Thr | Glu | Lys | Arg | Asn | Ala | Glu | Ala |
| | 210 | | | | | 215 | | | | | 220 | | | | |
| Lys | Ala | Arg | Thr | Ala | Glu | Glu | Ala | Lys | Gln | Ala | Thr | Ala | Asp | Lys |
| 225 | | | | 230 | | | | | 235 | | | | | 240 | |
| Glu | Lys | Ala | Glu | Thr | Glu | Ala | Lys | Lys | Ala | Lys | Glu | Ala | Lys | Thr |
| | | | | 245 | | | | | 250 | | | | | 255 | |
| Ala | Lys | Glu | Ala | Ala | His | Gln | Glu | Gln | Glu | Lys | Ala | Lys | Gln | Leu | Glu |
| | | | 260 | | | | | 265 | | | | | 270 | | |
| Gln | Ala | Asn | Gln | Gln | Ala | Asn | Gln | Arg | Ala | Asn | Leu | Ala | Glu | Lys | Ser |
| | | 275 | | | | | 280 | | | | | 285 | | | |
| Lys | Lys | Asp | Leu | Glu | Thr | Gln | Lys | Glu | Lys | Leu | Glu | Gln | Glu | Ile | Lys |
| | 290 | | | | | 295 | | | | | 300 | | | | |
| Glu | Ala | Thr | Glu | Ala | Lys | Asn | Lys | Ala | Glu | Lys | Leu | Lys | Asp | Leu |
| 305 | | | | | 310 | | | | | 315 | | | | | 320 |
| Gln | Asp | Ser | Ala | Ser | Gln | Gly | Ser | Glu | Leu | Ser | Lys | Gln | Leu | Leu | Lys |
| | | | | 325 | | | | | 330 | | | | | 335 | |

```
Glu Lys Glu Glu Leu Thr Thr Lys Leu Gln Glu Leu Gln Lys Gln Ala
                340                 345                 350
Glu Glu Lys Thr Thr Glu Ile Glu Lys Leu Lys Gln Glu Leu Glu Ala
            355                 360                 365
Asn Lys Gln Asn Ser Gly Gln Leu Gly Gln Gln Glu Gln Lys Leu Gln
        370                 375                 380
Glu Gln Leu Asn Lys Val Gln Lys Glu Leu Lys Gln Lys Glu Met Glu
385                 390                 395                 400
Leu Lys Gln Ala Gln Glu Gln Leu Lys Gln Glu Gln Lys Pro His Glu
                405                 410                 415
Gly Gly Gly Asp Ser Asp Ala Ser Lys Ala Arg Ile Thr Glu Leu Glu
            420                 425                 430
Lys Gln Val Gln Thr Leu Thr Lys Glu Lys Ala Asp Leu Ser Ser Thr
        435                 440                 445
Leu Glu Ser Thr Lys Ala Gln Leu Ser Glu Thr Gln Ala Arg Leu Ser
    450                 455                 460
Glu Ala Gln Lys Gln Leu Thr Ala Ala Gln Glu Lys Leu Thr Thr Leu
465                 470                 475                 480
Glu Ala Glu Lys Thr Ala Leu Gln His Gln Val Glu Thr Ile Ser Lys
                485                 490                 495
Gln Leu Ser Glu Thr Arg Asp Leu Ser Glu Lys Glu Lys Ala Ala Leu
            500                 505                 510
Gln Glu Gln Ile Asn Lys Leu Lys Ala Glu Ile Glu Gln Lys Thr Lys
        515                 520                 525
Glu Ile Glu Ala Leu Lys Gln Gly Met Gln Ser His Gln Gly Gln Glu
    530                 535                 540
Lys Pro Lys Asp Pro Lys Thr Pro Glu Thr Pro Lys Asp Pro Lys Thr
545                 550                 555                 560
Pro Glu Lys Asn Asp Gln Pro Gln Ala Pro Glu Lys Arg Ser Val Pro
                565                 570                 575
Trp Thr Ala Leu Thr Pro Ala Lys Pro Ile Asp Thr Thr Lys Ala Pro
            580                 585                 590
Lys Ser Ser Ala Pro Ser Pro Gln Thr Gly Ala Ala Thr Pro Lys Lys
        595                 600                 605
Gln

<210> SEQ ID NO 37
<211> LENGTH: 1032
<212> TYPE: DNA
<213> ORGANISM: Streptococcus equi

<400> SEQUENCE: 37
gaggtagttg aagtttggcc taatgggcaa atcctaatg gtaaaataga aattctaagt      60
caaactgagc actctgagca tttacagaaa ttacgcgata ttgagatttt ccaagctcaa    120
aagcaagctg atcatgttcg ttacactaaa tggttagatg gggtaactgt tgatgagcat    180
gaattcagaa aaatcaagga atatgacaca gaatattatg taacacctct tttaagtggt    240
aaaggttact atgatatcaa taagatttc aatcaagata gtgataaatg tgctgccgct    300
gtagcggcta atatgttcca ttattggttt gatagaaata gagacagtat taatcgtttc    360
ttaagtcaaa gtccaggtga aatggtgtt attaaacttg aaaatgaaaa acaatagaa      420 gtatcaaaat tttagaaac ttaccgtagt gatggtgatt atcttgataa agtccgttt      480 tttgacctta tcagtaacag ctttaaaggt cctgtttggg caaataagct attggatgct    540
```

```
tacattaacg gctatggtta tatccataaa tttgctaaaa atactccaca ttctaaaaat    600
aataatagta aatttaattt ctttaaaaaa gtatttgatg gtaatctctt gacagatatt    660
caccaaattt ttgattataa cacttttca gataaattaa gtgaggctct ctatactggt    720
aaagccattg gattggccta cggacctgga gacttgcgtc gttcactagg tcatattatt    780
tctgtctggg gagctgatct tgacgatcag aatcgcgtgg tagctattta tgtaactgat    840
tctgatgata aaagttaac tataggaaat gagagagttg gtttgaagcg atataaagta    900
tctagcgatg atcaaggtcg tgctcgtctg acgactcgtg ataaagataa cacaggtggt    960
gaaattcgat ctattgaaac attagatatg ggtacacaag agtgggcaga ttacttcaac   1020
aagacagaaa aa                                                       1032
```

<210> SEQ ID NO 38
<211> LENGTH: 344
<212> TYPE: PRT
<213> ORGANISM: Streptococcus equi

<400> SEQUENCE: 38

```
Glu Val Val Glu Val Trp Pro Asn Gly Gln Asn Pro Asn Gly Lys Ile
1               5                   10                  15

Glu Ile Leu Ser Gln Thr Glu His Ser Glu His Leu Gln Lys Leu Arg
            20                  25                  30

Asp Ile Glu Asp Phe Gln Ala Gln Lys Gln Ala Asp His Val Arg Tyr
        35                  40                  45

Thr Lys Trp Leu Asp Gly Val Thr Val Asp Glu His Glu Phe Arg Lys
    50                  55                  60

Ile Lys Glu Tyr Asp Thr Glu Tyr Tyr Val Thr Pro Leu Leu Ser Gly
65                  70                  75                  80

Lys Gly Tyr Tyr Asp Ile Asn Lys Asp Phe Asn Gln Asp Ser Asp Lys
                85                  90                  95

Cys Ala Ala Val Ala Ala Asn Met Phe His Tyr Trp Phe Asp Arg
            100                 105                 110

Asn Arg Asp Ser Ile Asn Arg Phe Leu Ser Gln Ser Pro Gly Glu Asn
        115                 120                 125

Gly Val Ile Lys Leu Glu Asn Glu Lys Thr Ile Glu Val Ser Lys Phe
    130                 135                 140

Leu Glu Thr Tyr Arg Ser Asp Gly Asp Tyr Leu Asp Lys Ser Pro Phe
145                 150                 155                 160

Phe Asp Leu Ile Ser Asn Ser Phe Lys Gly Pro Val Trp Ala Asn Lys
                165                 170                 175

Leu Leu Asp Ala Tyr Ile Asn Gly Tyr Gly Tyr Ile His Lys Phe Ala
            180                 185                 190

Lys Asn Thr Pro His Ser Lys Asn Asn Ser Lys Phe Asn Phe Phe
        195                 200                 205

Lys Lys Val Phe Asp Gly Asn Leu Leu Thr Asp Ile His Gln Ile Phe
    210                 215                 220

Asp Tyr Asn Thr Phe Ser Asp Lys Leu Ser Glu Ala Leu Tyr Thr Gly
225                 230                 235                 240

Lys Ala Ile Gly Leu Ala Tyr Gly Pro Gly Asp Leu Arg Arg Ser Leu
                245                 250                 255

Gly His Ile Ile Ser Val Trp Gly Ala Asp Leu Asp Asp Gln Asn Arg
            260                 265                 270

Val Val Ala Ile Tyr Val Thr Asp Ser Asp Asp Lys Lys Leu Thr Ile
        275                 280                 285
```

Gly Asn Glu Arg Val Gly Leu Lys Arg Tyr Lys Val Ser Ser Asp Asp
            290                 295                 300

Gln Gly Arg Ala Arg Leu Thr Thr Arg Asp Lys Asp Asn Thr Gly Gly
305                 310                 315                 320

Glu Ile Arg Ser Ile Glu Thr Leu Asp Met Gly Thr Gln Glu Trp Ala
                325                 330                 335

Asp Tyr Phe Asn Lys Thr Glu Lys
            340

<210> SEQ ID NO 39
<211> LENGTH: 867
<212> TYPE: DNA
<213> ORGANISM: Streptococcus equi

<400> SEQUENCE: 39

| | | | | | |
|---|---|---|---|---|---|
| tctaatggtg | aaacaagga | agctaagagt | gacaagctca | aggttgtggt | taccaattcc | 60 |
| attattgctg | acatgactaa | aaatattgca | ggtgacaaga | ttgacttgca | cagcattgtg | 120 |
| ccgattggtc | aagatccgca | tgagtatgag | ccattgccag | aagacgttga | aagaccagc | 180 |
| aatgccgatc | ttattctcta | taacggtatt | aaccttgaag | acggcggaca | ggcttggttt | 240 |
| acaaagcttg | taaaaaatgc | taagaaggaa | aaggacaagg | actacttcgc | tgtatctgat | 300 |
| ggtattgatg | tgatttacct | agaaggtgaa | agtgaaaaag | gcaaggaaga | ccctcatgct | 360 |
| tggttgaatc | ttgaaaatgg | ggttatctat | tcaaaaaata | ttgcaaagca | attgatcgct | 420 |
| aaagacccta | aaacaaggga | aacctatgaa | acaaccctaa | aagcttacgt | tgagaagcta | 480 |
| gagaagcttg | ataaggaagc | aaaatcaaaa | tttgatgcta | ttgctgacaa | taaaaagcta | 540 |
| atcgtcacaa | gtgaaggctg | cttcaaatac | ttctcaaaag | cttacggtgt | cccatcagcc | 600 |
| tacatctggg | aaatcaacac | tgaagaagaa | ggaactccgg | atcaaatttc | atcattgatc | 660 |
| gaaaaattga | agacgttaa | gccatcagcg | ctttttgttg | agtcaagtgt | tgacagacgt | 720 |
| ccaatggaga | ctgtttctaa | ggacagtggt | attccgatct | atgcagaaat | ctttactgac | 780 |
| tctgtagcca | aaaaaggcca | agatggagac | agctactatg | ccatgatgaa | atggaacctt | 840 |
| gataaaattt | ctgaaggctt | agcaaaa | | | | 867 |

<210> SEQ ID NO 40
<211> LENGTH: 289
<212> TYPE: PRT
<213> ORGANISM: Streptococcus equi

<400> SEQUENCE: 40

Ser Asn Gly Gly Asn Lys Glu Ala Lys Ser Asp Lys Leu Lys Val Val
1               5                   10                  15

Val Thr Asn Ser Ile Ile Ala Asp Met Thr Lys Asn Ile Ala Gly Asp
                20                  25                  30

Lys Ile Asp Leu His Ser Ile Val Pro Ile Gly Gln Asp Pro His Glu
            35                  40                  45

Tyr Glu Pro Leu Pro Glu Asp Val Glu Lys Thr Ser Asn Ala Asp Leu
        50                  55                  60

Ile Leu Tyr Asn Gly Ile Asn Leu Glu Asp Gly Gln Ala Trp Phe
65                  70                  75                  80

Thr Lys Leu Val Lys Asn Ala Lys Lys Glu Lys Asp Lys Asp Tyr Phe
                85                  90                  95

Ala Val Ser Asp Gly Ile Asp Val Ile Tyr Leu Glu Gly Glu Ser Glu
            100                 105                 110

```
Lys Gly Lys Glu Asp Pro His Ala Trp Leu Asn Leu Glu Asn Gly Val
        115                 120                 125

Ile Tyr Ser Lys Asn Ile Ala Lys Gln Leu Ile Ala Lys Asp Pro Lys
130                 135                 140

Asn Lys Glu Thr Tyr Glu Asn Asn Leu Lys Ala Tyr Val Glu Lys Leu
145                 150                 155                 160

Glu Lys Leu Asp Lys Glu Ala Lys Ser Lys Phe Asp Ala Ile Ala Asp
                165                 170                 175

Asn Lys Lys Leu Ile Val Thr Ser Glu Gly Cys Phe Lys Tyr Phe Ser
            180                 185                 190

Lys Ala Tyr Gly Val Pro Ser Ala Tyr Ile Trp Glu Ile Asn Thr Glu
        195                 200                 205

Glu Glu Gly Thr Pro Asp Gln Ile Ser Ser Leu Ile Glu Lys Leu Lys
    210                 215                 220

Asp Val Lys Pro Ser Ala Leu Phe Val Glu Ser Ser Val Asp Arg Arg
225                 230                 235                 240

Pro Met Glu Thr Val Ser Lys Asp Ser Gly Ile Pro Ile Tyr Ala Glu
                245                 250                 255

Ile Phe Thr Asp Ser Val Ala Lys Lys Gly Gln Asp Gly Asp Ser Tyr
            260                 265                 270

Tyr Ala Met Met Lys Trp Asn Leu Asp Lys Ile Ser Glu Gly Leu Ala
        275                 280                 285

Lys
```

<210> SEQ ID NO 41
<211> LENGTH: 31
<212> TYPE: DNA
<213> ORGANISM: Artificial
<220> FEATURE:
<223> OTHER INFORMATION: Oligonucleotides as PCR primer

<400> SEQUENCE: 41
aaaggatcct gcagtctaca aatgacaata c                                    31

<210> SEQ ID NO 42
<211> LENGTH: 35
<212> TYPE: DNA
<213> ORGANISM: Artificial
<220> FEATURE:
<223> OTHER INFORMATION: Oligonucleotides as PCR primer

<400> SEQUENCE: 42
aaagaattct tattttctg acttagattt agaag                                 35

<210> SEQ ID NO 43
<211> LENGTH: 34
<212> TYPE: DNA
<213> ORGANISM: Artificial
<220> FEATURE:
<223> OTHER INFORMATION: Oligonucleotides as PCR primer

<400> SEQUENCE: 43
aaaggatcct ggcgactacc ctagcaggac aaac                                 34

<210> SEQ ID NO 44
<211> LENGTH: 33
<212> TYPE: DNA
<213> ORGANISM: Artificial
<220> FEATURE:
<223> OTHER INFORMATION: Oligonucleotides as PCR primer

<400> SEQUENCE: 44
aaagaattct tatgtatctt gacagtgctt aag		33

<210> SEQ ID NO 45
<211> LENGTH: 33
<212> TYPE: DNA
<213> ORGANISM: Artificial
<220> FEATURE:
<223> OTHER INFORMATION: Oligonucleotides as PCR primer

<400> SEQUENCE: 45
cccggatcct agaagggata atgataaaa tag		33

<210> SEQ ID NO 46
<211> LENGTH: 34
<212> TYPE: DNA
<213> ORGANISM: Artificial
<220> FEATURE:
<223> OTHER INFORMATION: Oligonucleotides as PCR primer

<400> SEQUENCE: 46
tttgaattct tacaaaacat ctactactgg caac		34

<210> SEQ ID NO 47
<211> LENGTH: 1002
<212> TYPE: DNA
<213> ORGANISM: Streptococcus equi

<400> SEQUENCE: 47
atgaaaaaat caactaaatt acttgctggt atcgtaaccc tagcatcagc aatgaccta		60
gcagcctgtc agtctacaaa tgacaataca agtgtcatta cgatgaaggg cgacactatc		120
agtgttagtg atttttacaa tgaaacaaaa aatacagaga tttctcaaag agcaatgcta		180
aaccttgtgg ttagtcgtgt ttttgaggac caatacggta aaaaggtttc taagaaaaga		240
acggaagaag cttacaataa atcagctgag caatacggtg cgtcattctc tgcagccctt		300
gcgcagtctg gcttgacaac agatacctac aagcgtcaaa ttcgctcagc catgctggtt		360
gaatatgctg ttaagaagc agctaaaaaa gagctgacag atgctgatta caaaaaagcc		420
tatgagtcat acacaccaga aatgactact caggtcacta ctctagacaa tgaagaaaca		480
gcaaaggctg ttttaggtga ggttaaggct gagggtgctg actttgctgc tattgctaag		540
gaaaagacaa cagcagcaga caagaaggta gactataagt ttgactcagg agacactaag		600
ttaccagcag atgtgatcaa ggccgcctca ggattaaaag agggtgatat ttcagaggtg		660
gtttctgtct tagatccggc tacttatcaa acaagttct atattgttaa ggtaaccaaa		720
aaagccgaaa aggcttctga ttggaagaaa tataagaaac gtctaaaaga aattgtcttg		780
gctgaaaaga cacaaaacat tgatttccaa aataaggtca ttgcaaaggc cttagacaag		840
gcaaatgtta agatcaaaga ccaagcattt gctaatatct tggcacagta tgccaatact		900
gataaaaaag caagcaaggc gaacacaagc aagtcagatc agaaatcatc ttcagactca		960
agcaaggata gtcaatcttc taaatctaag tcagaaaaat ag		1002

<210> SEQ ID NO 48
<211> LENGTH: 333
<212> TYPE: PRT
<213> ORGANISM: Streptococcus equi

<400> SEQUENCE: 48

```
Met Lys Lys Ser Thr Lys Leu Leu Ala Gly Ile Val Thr Leu Ala Ser
1               5                   10                  15

Ala Met Thr Leu Ala Ala Cys Gln Ser Thr Asn Asp Asn Thr Ser Val
            20                  25                  30

Ile Thr Met Lys Gly Asp Thr Ile Ser Val Ser Asp Phe Tyr Asn Glu
        35                  40                  45

Thr Lys Asn Thr Glu Ile Ser Gln Arg Ala Met Leu Asn Leu Val Val
50                  55                  60

Ser Arg Val Phe Glu Asp Gln Tyr Gly Lys Lys Val Ser Lys Lys Arg
65                  70                  75                  80

Thr Glu Glu Ala Tyr Asn Lys Ser Ala Glu Gln Tyr Gly Ala Ser Phe
                85                  90                  95

Ser Ala Ala Leu Ala Gln Ser Gly Leu Thr Thr Asp Thr Tyr Lys Arg
                100                 105                 110

Gln Ile Arg Ser Ala Met Leu Val Glu Tyr Ala Val Lys Glu Ala Ala
            115                 120                 125

Lys Lys Glu Leu Thr Asp Ala Asp Tyr Lys Lys Ala Tyr Glu Ser Tyr
130                 135                 140

Thr Pro Glu Met Thr Thr Gln Val Thr Thr Leu Asp Asn Glu Glu Thr
145                 150                 155                 160

Ala Lys Ala Val Leu Gly Glu Val Lys Ala Glu Gly Ala Asp Phe Ala
                165                 170                 175

Ala Ile Ala Lys Glu Lys Thr Thr Ala Ala Asp Lys Lys Val Asp Tyr
            180                 185                 190

Lys Phe Asp Ser Gly Asp Thr Lys Leu Pro Ala Asp Val Ile Lys Ala
        195                 200                 205

Ala Ser Gly Leu Lys Glu Gly Asp Ile Ser Glu Val Val Ser Val Leu
210                 215                 220

Asp Pro Ala Thr Tyr Gln Asn Lys Phe Tyr Ile Val Lys Val Thr Lys
225                 230                 235                 240

Lys Ala Glu Lys Ala Ser Asp Trp Lys Lys Tyr Lys Lys Arg Leu Lys
                245                 250                 255

Glu Ile Val Leu Ala Glu Lys Thr Gln Asn Ile Asp Phe Gln Asn Lys
            260                 265                 270

Val Ile Ala Lys Ala Leu Asp Lys Ala Asn Val Lys Ile Lys Asp Gln
        275                 280                 285

Ala Phe Ala Asn Ile Leu Ala Gln Tyr Ala Asn Thr Asp Lys Lys Ala
    290                 295                 300

Ser Lys Ala Asn Thr Ser Lys Ser Asp Gln Lys Ser Ser Ser Asp Ser
305                 310                 315                 320

Ser Lys Asp Ser Gln Ser Ser Lys Ser Glu Lys
                325                 330
```

<210> SEQ ID NO 49
<211> LENGTH: 1179
<212> TYPE: DNA
<213> ORGANISM: Streptococcus equi

<400> SEQUENCE: 49

```
atgactgtgt taaatatctt tcagtcaaaa ttaatatgtc tatcattaaa ggagagagaa        60
atgaacaaaa aatcagcaag acgcaggcgt aagaatctta ttacgaagct tgcgatgaca       120
agtgccttaa ccctgggtgt aggcgcgact accctagcag acaaacagag agtacgggct       180
gataatatct tacgcttaga tatgacagat aaagaagcag ttgaaaaatt cgctaacgag       240
```

```
cttaaaaatg aagtccataa aaactatcgt ggtagtaata cttggcaaaa gcttacccct      300
atacttaatg gttatcaaaa ccttagagaa caaatagaga ccgagctaaa aaatagtgaa      360
caaaaagtaa aagagcttaa tgataaggtt aatagtgaaa ctcaaggaaa acaagagtta      420
cagaatcagc ttgagaaaga aaagaagag ttagaaacac taaaaaaaga gcttgaagct       480
gagaaggcta aaggaactgg agaaacagag aagcttcaaa aggaaattga agcaaaaaat      540
gcaatgattt ctgacctaca aaacagctt gaggaaacta agcaagggt tcaagagttt        600 gaagctgaag taggtaaatt aatggccgaa aaggcagacc tacaaacaaa attaaatgaa      660
caagagcagc ttaacgctaa gcttcaaaaa gaaattgaag acttaaaggc tcagattgaa      720
aagcttaagc actgtcaaga tacacctaag ccagagccta agccagagcc taagccagag      780
cctaagccag agcctaagcc agagcctaag ccagagccta agccagagcc taagccagag      840
cctaagccag ggcctaagcc agagcctaag ccagagccta gccagggcc taagccagag       900 cctaagccag agcctaagcc agggcctaag ccagggccta agcagagcc taagccaggg        960 cctaagccag agcctaagcc agagcctaag ccagagccta agcctgaagc taagaagcct     1020
gaacaaccta aaccaatgac taaaccagga gctaagaagc ctgagcaatc acttccatca     1080
actggtgaca tcagaaatcc attcttcacg cctgcagcta ttgctattat gatcgcagca     1140
ggtaccattg ccattccaaa acgcaaggaa gaagattaa                              1179
```

<210> SEQ ID NO 50
<211> LENGTH: 393
<212> TYPE: PRT
<213> ORGANISM: Streptococcus equi
<400> SEQUENCE: 50

```
Met Thr Val Leu Lys Tyr Leu Gln Ser Lys Leu Ile Cys Leu Ser Leu
1               5                   10                  15

Lys Glu Arg Glu Met Asn Lys Lys Ser Ala Arg Arg Arg Lys Asn
            20                  25                  30

Leu Ile Thr Lys Leu Ala Met Thr Ser Ala Leu Thr Leu Gly Val Gly
        35                  40                  45

Ala Ala Thr Leu Ala Gly Gln Thr Glu Val Arg Ala Asp Asn Ile
    50                  55                  60

Leu Arg Leu Asp Met Thr Asp Lys Glu Ala Val Glu Lys Phe Ala Asn
65                  70                  75                  80

Glu Leu Lys Asn Glu Val His Lys Asn Tyr Arg Gly Ser Asn Thr Trp
                85                  90                  95

Gln Lys Leu Thr Leu Ile Leu Asn Gly Tyr Gln Asn Leu Arg Glu Gln
            100                 105                 110

Ile Glu Thr Glu Leu Lys Asn Ser Glu Gln Lys Val Lys Glu Leu Asn
        115                 120                 125

Asp Lys Val Asn Ser Glu Thr Gln Gly Lys Gln Glu Leu Gln Asn Gln
    130                 135                 140

Leu Glu Lys Glu Lys Glu Glu Leu Glu Thr Leu Lys Lys Glu Leu Glu
145                 150                 155                 160

Ala Glu Lys Ala Lys Gly Thr Gly Glu Thr Glu Lys Leu Gln Lys Glu
                165                 170                 175

Ile Glu Ala Lys Asn Ala Met Ile Ser Asp Leu Gln Lys Gln Leu Glu
            180                 185                 190

Glu Thr Lys Gln Arg Val Gln Glu Phe Glu Ala Glu Val Gly Lys Leu
        195                 200                 205
```

-continued

Met Ala Glu Lys Ala Asp Leu Gln Thr Lys Leu Asn Glu Gln Glu Gln
    210                 215                 220

Leu Asn Ala Lys Leu Gln Lys Glu Ile Glu Asp Leu Lys Ala Gln Ile
225                 230                 235                 240

Glu Lys Leu Lys His Cys Gln Asp Thr Pro Lys Pro Glu Pro Lys Pro
                245                 250                 255

Glu Pro Lys Pro Glu Pro Lys Pro Glu Pro Lys Pro Glu Pro Lys Pro
            260                 265                 270

Glu Pro Lys Pro Glu Pro Lys Pro Glu Pro Lys Pro Gly Pro Lys Pro
        275                 280                 285

Glu Pro Lys Pro Glu Pro Lys Pro Gly Pro Lys Pro Glu Pro Lys Pro
    290                 295                 300

Glu Pro Lys Pro Gly Pro Lys Pro Gly Pro Lys Pro Glu Pro Lys Pro
305                 310                 315                 320

Gly Pro Lys Pro Glu Pro Lys Pro Glu Pro Lys Pro Glu Pro Lys Pro
                325                 330                 335

Glu Ala Lys Lys Pro Glu Gln Pro Lys Pro Met Thr Lys Pro Gly Ala
            340                 345                 350

Lys Lys Pro Glu Gln Ser Leu Pro Ser Thr Gly Asp Ile Arg Asn Pro
        355                 360                 365

Phe Phe Thr Pro Ala Ala Ile Ala Ile Met Ile Ala Ala Gly Thr Ile
    370                 375                 380

Ala Ile Pro Lys Arg Lys Glu Glu Asp
385                 390

<210> SEQ ID NO 51
<211> LENGTH: 573
<212> TYPE: DNA
<213> ORGANISM: Streptococcus equi

<400> SEQUENCE: 51
atgaaaaaag taataaatac tattctatta gctgcttgtt ttttattctt tttaggtaat    60
tttactacaa atgtattagc tgaagggata aatgataaaa tagaaaatgg cactgaaagc   120
gatattagct tccaaaatgg tgaactccta aaaaattatc ttatcctaga aggtgaacga   180
gtatactttg attatgatag agcaactcaa gataaagtat cagatgatgt tctagagatg   240
ggaatgttag ttgaagctat aagtaaggat tattctgaga agacattcac cccagataaa   300 tatttttaaag ctagttggcc tatccatggt aactattgtg gaccaggtca taatgggaat   360
aactttacgt tgccagtagt agatgttttg gatcaaggtt gccaaaacca cgatagttgc   420
tataagtggg gtgccggtat tggtgctaat tgtgaatgta accgtcagct cgttaattac   480
ataaaagttt atagacgatg gatgccagcg aatgtccttg gcgtagccga tgctattaga   540
gtatattttg agacagtagg ttctatagga tgt                                573

<210> SEQ ID NO 52
<211> LENGTH: 191
<212> TYPE: PRT
<213> ORGANISM: Streptococcus equi

<400> SEQUENCE: 52

Met Lys Lys Val Ile Asn Thr Ile Leu Leu Ala Ala Cys Phe Leu Phe
1               5                   10                  15

Phe Leu Gly Asn Phe Thr Thr Asn Val Leu Ala Glu Gly Ile Asn Asp
            20                  25                  30

Lys Ile Glu Asn Gly Thr Glu Ser Asp Ile Ser Phe Gln Asn Gly Glu

```
                  35                  40                  45
Leu Leu Lys Asn Tyr Leu Ile Leu Glu Gly Glu Arg Val Tyr Phe Asp
    50                  55                  60

Tyr Asp Arg Ala Thr Gln Asp Lys Val Ser Asp Val Leu Glu Met
65                  70                  75                  80

Gly Met Leu Val Glu Ala Ile Ser Lys Asp Tyr Ser Glu Lys Thr Phe
                85                  90                  95

Thr Pro Asp Lys Tyr Phe Lys Ala Ser Trp Pro Ile His Gly Asn Tyr
                100                 105                 110

Cys Gly Pro Gly His Asn Gly Asn Asn Phe Thr Leu Pro Val Val Asp
                115                 120                 125

Val Leu Asp Gln Gly Cys Gln Asn His Asp Ser Cys Tyr Lys Trp Gly
            130                 135                 140

Ala Gly Ile Gly Ala Asn Cys Glu Cys Asn Arg Gln Leu Val Asn Tyr
145                 150                 155                 160

Ile Lys Val Tyr Arg Arg Trp Met Pro Ala Asn Val Leu Gly Val Ala
                165                 170                 175

Asp Ala Ile Arg Val Tyr Phe Glu Thr Val Gly Ser Ile Gly Cys
                180                 185                 190

<210> SEQ ID NO 53
<211> LENGTH: 930
<212> TYPE: DNA
<213> ORGANISM: Streptococcus equi

<400> SEQUENCE: 53
cagtctacaa atgacaatac aagtgtcatt acgatgaagg gcgacactat cagtgttagt      60
gatttttaca atgaaacaaa aaatacagag atttctcaaa gagcaatgct aaaccttgtg     120
gttagtcgtg tttttgagga ccaatacggt aaaaaggttt ctaagaaaag aacggaagaa     180
gcttacaata aatcagctga gcaatacggt gcgtcattct ctgcagccct tgcgcagtct     240
ggcttgacaa cagataccta caagcgtcaa attcgctcag ccatgctggt tgaatatgct     300
gttaaagaag cagctaaaaa agagctgaca gatgctgatt acaaaaaagc ctatgagtca     360
tacacaccag aaatgactac tcaggtcact actctagaca tgaagaaac agcaaaggct     420 gttttaggtg aggttaaggc tgagggtgct gactttgctg ctattgctaa ggaaaagaca     480
acagcagcag acaagaaggt agactataag tttgactcag agacactaa gttaccagca     540 gatgtgatca aggccgcctc aggattaaaa gagggtgata tttcagaggt ggtttctgtc     600
ttagatccgg ctacttatca aaacaagttc tatattgtta aggtaaccaa aaaagccgaa     660
aaggcttctg attggaagaa atataagaaa cgtctaaaag aaattgtctt ggctgaaaag     720
acacaaaaca ttgatttcca aaataaggtc attgcaaagg ccttagacaa ggcaaatgtt     780
aagatcaaag accaagcatt tgctaatatc ttggcacagt atgccaatac tgataaaaaa     840
gcaagcaagg cgaacacaag caagtcagat cagaaatcat cttcagactc aagcaaggat     900
agtcaatctt ctaaatctaa gtcagaaaaa                                     930

<210> SEQ ID NO 54
<211> LENGTH: 310
<212> TYPE: PRT
<213> ORGANISM: Streptococcus equi

<400> SEQUENCE: 54

Gln Ser Thr Asn Asp Asn Thr Ser Val Ile Thr Met Lys Gly Asp Thr
1               5                   10                  15
```

```
Ile Ser Val Ser Asp Phe Tyr Asn Glu Thr Lys Asn Thr Glu Ile Ser
             20                  25                  30

Gln Arg Ala Met Leu Asn Leu Val Val Ser Arg Val Phe Glu Asp Gln
         35                  40                  45

Tyr Gly Lys Lys Val Ser Lys Lys Arg Thr Glu Glu Ala Tyr Asn Lys
     50                  55                  60

Ser Ala Glu Gln Tyr Gly Ala Ser Phe Ser Ala Ala Leu Ala Gln Ser
 65                  70                  75                  80

Gly Leu Thr Thr Asp Thr Tyr Lys Arg Gln Ile Arg Ser Ala Met Leu
                 85                  90                  95

Val Glu Tyr Ala Val Lys Glu Ala Ala Lys Lys Glu Leu Thr Asp Ala
            100                 105                 110

Asp Tyr Lys Lys Ala Tyr Glu Ser Tyr Thr Pro Glu Met Thr Thr Gln
        115                 120                 125

Val Thr Thr Leu Asp Asn Glu Glu Thr Ala Lys Ala Val Leu Gly Glu
    130                 135                 140

Val Lys Ala Glu Gly Ala Asp Phe Ala Ala Ile Ala Lys Glu Lys Thr
145                 150                 155                 160

Thr Ala Ala Asp Lys Lys Val Asp Tyr Lys Phe Asp Ser Gly Asp Thr
                165                 170                 175

Lys Leu Pro Ala Asp Val Ile Lys Ala Ala Ser Gly Leu Lys Glu Gly
            180                 185                 190

Asp Ile Ser Glu Val Val Ser Val Leu Asp Pro Ala Thr Tyr Gln Asn
        195                 200                 205

Lys Phe Tyr Ile Val Lys Val Thr Lys Lys Ala Glu Lys Ala Ser Asp
    210                 215                 220

Trp Lys Lys Tyr Lys Lys Arg Leu Lys Glu Ile Val Leu Ala Glu Lys
225                 230                 235                 240

Thr Gln Asn Ile Asp Phe Gln Asn Lys Val Ile Ala Lys Ala Leu Asp
                245                 250                 255

Lys Ala Asn Val Lys Ile Lys Asp Gln Ala Phe Ala Asn Ile Leu Ala
            260                 265                 270

Gln Tyr Ala Asn Thr Asp Lys Lys Ala Ser Lys Ala Asn Thr Ser Lys
        275                 280                 285

Ser Asp Gln Lys Ser Ser Asp Ser Ser Lys Asp Ser Gln Ser Ser
    290                 295                 300

Lys Ser Lys Ser Glu Lys
305                 310

<210> SEQ ID NO 55
<211> LENGTH: 600
<212> TYPE: DNA
<213> ORGANISM: Streptococcus equi

<400> SEQUENCE: 55
gcgactaccc tagcaggaca aacagaagta cgggctgata atatcttacg cttagatatg      60
acagataaag aagcagttga aaaattcgct aacgagctta aaaatgaagt ccataaaaac     120
tatcgtggta gtaatacttg caaaagctt acccttatac ttaatggtta tcaaaacctt     180
agagaacaaa tagagaccga gctaaaaaat agtgaacaaa aagtaaaaga gcttaatgat     240
aaggttaata gtgaaactca aggaaaacaa gagttacaga atcagcttga aaagaaaaa     300 gaagagttag aaacactaaa aaaagagctt gaagctgaga aggctaaagg aactggagaa     360
acagagaagc ttcaaaagga aattgaagca aaaaatgcaa tgatttctga cctacaaaaa     420
```

```
cagcttgagg aaactaagca aagggttcaa gagtttgaag ctgaagtagg taaattaatg      480
gccgaaaagg cagacctaca aacaaaatta aatgaacaag agcagcttaa cgctaagctt      540
caaaaagaaa ttgaagactt aaaggctcag attgaaaagc ttaagcactg tcaagataca      600
```

<210> SEQ ID NO 56
<211> LENGTH: 200
<212> TYPE: PRT
<213> ORGANISM: Streptococcus equi

<400> SEQUENCE: 56

```
Ala Thr Thr Leu Ala Gly Gln Thr Glu Val Arg Ala Asp Asn Ile Leu
 1               5                  10                  15

Arg Leu Asp Met Thr Asp Lys Glu Ala Val Glu Lys Phe Ala Asn Glu
            20                  25                  30

Leu Lys Asn Glu Val His Lys Asn Tyr Arg Gly Ser Asn Thr Trp Gln
        35                  40                  45

Lys Leu Thr Leu Ile Leu Asn Gly Tyr Gln Asn Leu Arg Glu Gln Ile
    50                  55                  60

Glu Thr Glu Leu Lys Asn Ser Glu Gln Lys Val Lys Glu Leu Asn Asp
65                  70                  75                  80

Lys Val Asn Ser Glu Thr Gln Gly Lys Gln Glu Leu Gln Asn Gln Leu
                85                  90                  95

Glu Lys Glu Lys Glu Glu Leu Glu Thr Leu Lys Lys Glu Leu Glu Ala
            100                 105                 110

Glu Lys Ala Lys Gly Thr Gly Glu Thr Glu Lys Leu Gln Lys Glu Ile
        115                 120                 125

Glu Ala Lys Asn Ala Met Ile Ser Asp Leu Gln Lys Gln Leu Glu Glu
    130                 135                 140

Thr Lys Gln Arg Val Gln Glu Phe Glu Ala Glu Val Gly Lys Leu Met
145                 150                 155                 160

Ala Glu Lys Ala Asp Leu Gln Thr Lys Leu Asn Glu Gln Glu Gln Leu
                165                 170                 175

Asn Ala Lys Leu Gln Lys Glu Ile Glu Asp Leu Lys Ala Gln Ile Glu
            180                 185                 190

Lys Leu Lys His Cys Gln Asp Thr
        195                 200
```

<210> SEQ ID NO 57
<211> LENGTH: 309
<212> TYPE: DNA
<213> ORGANISM: Streptococcus equi

<400> SEQUENCE: 57

```
gaagggataa atgataaaat agaaaatggc actgaaagcg atattagctt ccaaaatggt       60
gaactcctaa aaaattatct tatcctagaa ggtgaacgag tatactttga ttatgataga      120
gcaactcaag ataaagtatc agatgatgtt ctagagatgg aatgttagt tgaagctata       180 agtaaggatt attctgagaa gacattcacc ccagataaat attttaaagc tagttggcct      240
atccatggta actattgtgg accaggtcat aatgggaata actttacgtt gccagtagta      300
gatgttttg                                                              309
```

<210> SEQ ID NO 58
<211> LENGTH: 103
<212> TYPE: PRT
<213> ORGANISM: Streptococcus equi

```
<400> SEQUENCE: 58

Glu Gly Ile Asn Asp Lys Ile Glu Asn Gly Thr Glu Ser Asp Ile Ser
1               5                   10                  15

Phe Gln Asn Gly Glu Leu Leu Lys Asn Tyr Leu Ile Leu Glu Gly Glu
            20                  25                  30

Arg Val Tyr Phe Asp Tyr Asp Arg Ala Thr Gln Asp Lys Val Ser Asp
            35                  40                  45

Asp Val Leu Glu Met Gly Met Leu Val Glu Ala Ile Ser Lys Asp Tyr
        50                  55                  60

Ser Glu Lys Thr Phe Thr Pro Asp Lys Tyr Phe Lys Ala Ser Trp Pro
65                  70                  75                  80

Ile His Gly Asn Tyr Cys Gly Pro Gly His Asn Gly Asn Asn Phe Thr
                85                  90                  95

Leu Pro Val Val Asp Val Leu
                100
```